US008178347B2

(12) United States Patent
Davidson

(10) Patent No.: US 8,178,347 B2
(45) Date of Patent: May 15, 2012

(54) GENE REGULATORY NETWORKS AND METHODS OF INTERDICTION FOR CONTROLLING THE DIFFERENTIATION STATE OF A CELL

(75) Inventor: Eric H. Davidson, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 1156 days.

(21) Appl. No.: 11/894,804

(22) Filed: Aug. 20, 2007

(65) Prior Publication Data

US 2008/0206759 A1 Aug. 28, 2008

Related U.S. Application Data

(63) Continuation of application No. 10/452,766, filed on May 30, 2003, now abandoned.

(60) Provisional application No. 60/384,962, filed on May 30, 2002.

(51) Int. Cl.
*C12N 5/00* (2006.01)
*C12N 5/02* (2006.01)
*C07H 21/02* (2006.01)

(52) U.S. Cl. ...................................... 435/325; 536/23.1

(58) Field of Classification Search .......................... None
See application file for complete search history.

(56) References Cited

U.S. PATENT DOCUMENTS 5,580,859 A 12/1996 Felgner et al.
5,712,379 A 1/1998 Davidson

OTHER PUBLICATIONS

Angerer et al., "Animal-Vegetal Axis Patterning Mechanisms in the Early Sea Urchin Embryo," Developmental Biology, 218:1-12, (2000).
Arnone et al., "The hardwiring of development: organization and function of genomic regulatory systems," Development, 124:1851-1864, (1997).
Berman et al., "Exploiting transcription factor binding site clustering to identify cis-regulatory modules involved in pattern formation in the Drosophila genome," PNAS, 99(2):757-762, (2002).
Bolouri et al., "Modeling DNA Sequence-Based cis-Regulatory Gene Networks," Developmental Biology, 246:2-13, (2002).
Bottino et al., Gene Therapy, 10:875-889, (2003).
Britten et al., "Repetitive and Non-Repetitive DNA Sequences and a Speculation on the Origins of Evolutionary Novelty" The Quarterly Review of Biology, 46(2):111-138, (1971).
Brown et al., "New Computational Approaches for Analysis of cis-Regulatory Networks," Developmental Biology, 246:86-102 (2002).
Byrd et al., Development, 129:361-372, (2002).
Burlingame et al., PharmaGenomics, 25-29, (2003).
Cameron et al., "A sea urchin genome project: Sequence scan, virtual map, and additional resources," PNAS, 97(17):9514-9518, (2000).
Choi-Lundberg et al., Science, 275:838-842, (1997).
Chuang et al., "Transient Appearance of Strongylocentrotus purpuratus Otx in Micromere Nuclei: Cytoplasmic Retention of SpOtx Possibly Mediated Through an α-Actinin Interaction," Developmental Genetics, 19(3):231-237, (1996).
Davidson et al., "A Genomic Regulatory Network for Development," Science, 295:1669-1678, (2002).
Davidson et al., "A Provisional Regulatory Gene Network for Specification of Endomesoderm in the Sea Urchin Embryo," Developmental Biology, 246:162-190, (2002).
Davidson et al., "Genomic cis-regulatory logic: experimental and computational analysis of a sea urchin gene," Science, 279(5358):1896, (1998).
Davidson et al., "Regulatory gene networks and the properties of the developmental process," PNAS, 100(4):1475-1480, (2003).
Davidson et al., "Specification of cell fate in the sea urchin embryo: summary and some proposed mechanisms," Development, 125:3269-3290, (1998).
Davidson, E.H., Genomic Regulatory Systems: Development and Evolution Academic, San Diego (2001) Chapters 2 & 3.
Davidson, Eric, "Spatial mechanisms of gene regulation in metazoan embryos," Development, 113:1-26, (1991).
Flytzanis et al., "Ontogenic activation of a fusion gene introduced into sea urchin eggs," Proc. Natl. Acad. Sci, 84:151-155, (1987).
Gonzales and Lessios, Mol. Biol. Evol., 16:938, (1999).
Horstadius, Biol. Res. Camb. Phiols Soc., 14:132, (1939).
Howard et al., "SpKrl: a direct target of β-catenin regulation required for endoderm differentiation in sea urchin embryos," Development, 128:365-375, (2001).
Jones, HHMI Bulletin, Mar. 10-16, 2002, Stem Cells: Scientific Progress and Future Directions, Appendix C, NIH (2001).
Kenny et al., Development, 126:5473, (1999).
Kim et al., Nature, 418:50-56, (2002).

(Continued)

*Primary Examiner* — Joanne Hama
(74) *Attorney, Agent, or Firm* — McCarter & English, LLP; Elizabeth A. Hanley, Esq.; Yu Lu

(57) ABSTRACT

The invention provides a method of modulating a regulatory state of a cell. The method consists of: (a) identifying a point of interdiction within a cis regulatory network specifying a genetic regulatory architecture of a cell, and (b) introducing into a progenitor cell two or more network elements within said network to induce a predetermined series of cis regulatory network interactions resulting in a specified regulatory state of said progenitor cell. Also provided is a method of modulating a regulatory state of a cell. The method consists of: (a) identifying a point of interdiction within a cis regulatory network specifying a genetic regulatory architecture of a cellular state, and (b) introducing into a progenitor cell two or more network elements within said network to induce a predetermined series of cis regulatory network interactions resulting in a specified regulatory state of said progenitor cell. A cell having a specified regulatory state consisting of a modified genetic regulatory architecture is further provided. Methods of diagnosing and methods of treating an individual suffering from a cellular defect also are provided. The invention additionally provides a method of identifying a compound having differentiation or cell fate inducing activity.

4 Claims, 12 Drawing Sheets

OTHER PUBLICATIONS

Kirchhamer et al., "Spatial and temporal information processing in the sea urchin embryo: modular and intramodular organization of the CyIIIa gene cis-regulatory system," Development, 122:333-348, (1996).

Kurokawa et al., "HpEts, an ets-related transcription factor implicated in primary mesenchyme cell differentiation in the sea urchin embryo," Mechanisms of Development, 80:41-52, (1999).

Li et al., "Requirement of SpOtx in Cell Fate Decisions in the Sea Urchin Embryo and Possible Role as a Mediator of β-Catenin Signaling," Developmental Biology, 212:425-439, (1999).

Li et al., "Two Otx Proteins Generated from Multiple Transcripts of a Single Gene in *Strongylocentrotus purpuratus*," Developmental Biology, 187:253-266, (1997).

Logan et al., "Nuclear β-catenin is required to specify vegetal cell fates in the sea urchin embryo," Development, 126:345-357, (1999).

Logan et al., "The allocation of early blastomeres to the ectoderm and endoderm is variable in the sea urchin embryo," Development, 124:2213-2223, (1997).

Luke et al., Dev. Growth Difference, 39:285, (1997).

Maier et al., J. Biotechnol., 35:191-203, 1994.

McClay and Gross, Dev. Biol., 239:132, (2001).

McMahon et al., "Introduction of Cloned DNA into Sea Urchin Egg Cytoplasm: Replication and Persistence during Embryogenesis," Developmental Biology, 108:420-430, (1985).

Nocente-McGrath et al., "Endo16, a Lineage-Specific Protein of the Sea Urchin Embryo, Is First Expressed Just prior to Gastrulation," Developmental Biology, 136:264-272, (1989).

Oliveri et al., "A Regulatory Gene Network That Directs Micromere Specification in the Sea Urchin Embryo," Developmental Biology, 246:209-228, (2002).

Paul and Smith, Biol. Rev. 59:443, (1984).

Pellegrineschi et al., JIRCAS Working Report, 55-60, (2002).

Poustka et al., "Toward the Gene Catalogue of Sea Urchin Development: The Construction and Analysis of an Unfertilized Egg cDNA Library Highly Normalized by Oligonucleotide Fingerprinting," Genomics, 59:122-133, (1999).

Ransick and Davidson, Development, 121:3215-3222, (1995).

Ransick et al., "A Complete Second Gut Induced by Transplanted Micromeres in the Sea Urchin Embryo," Science, 259:1134-1138, (1993).

Ransick et al., "Late Specification of Veg1, Lineages to Endodermal Fate in the Sea Urchin Embryo," Developmental Biology, 195(1):38-48, (1998).

Ransick et al., "New Early Zygotic Regulators Expressed in Endomesoderm of Sea Urchin Embryos Discovered by Differential Array Hybridization," Developmental Biology, 246:132-147, (2002).

Ransick et al., "Whole mount in situ hybridization shows Endo 16 to be a marker for the vegetal plate territory in sea urchin embryos," Mech. of Development, 42:117-124, (1993).

Rast et al., "Brachyury Target Genes in the Early Sea Urchin Embryo Isolated by Differential Macroarray Screening," Developmental Biology, 246:191-208, (2002).

Rast et al., Dev. Biol., 228:270, (2000).

Rothenburg et al., "Elements of Transcription Factor Network Design for T-Lineage Specification," Developmental Biology, 246:29-44, (2002).

Ruffins et al., "A Clonal Analysis of Secondary Mesenchyme Cell Fates in the Sea Urchin Embryo," Developmental Biology, 160:285-288, (1993).

Ruffins et al., "A fate map of the vegetal plate of the sea urchin (*Lytechinus variegates*) mesenchyme blastula," Development, 122:253-263, (1996).

Scully and Rosenfeld, Science, 295:2231-2235, (2002).

Sherwood et al., "LvNotch signaling mediates secondary mesenchyme specification in the sea urchin embryo," Development, 126:1703-1713, (1999).

Sherwood et al., "LvNotch signaling plays a dual role in regulating the position of the ectoderm-endoderm boundary in the sea urchin embryo," Development, 128:2221-2232, (2001).

Soltysik-Espanola et al., "Endo16, a Large Multidomain Protein Found on the Surface and ECM of Endodermal Cells during Sea Urchin Gastrulation, Binds Calcium," Developmental Biology, 165:73-85, (1994).

Sonnhammer and Durbin, Gene, 176:GC1-GC10, (1995).

Sucov et al., Genes Dev. 2:1238, (1988).

Sweet et al., "The role of micromere signaling in Notch activation and mesoderm specification during sea urchin embryogenesis," Development, 126:5255-5265, (1999).

Wang et al., Mech. Dev., 60:185, (1996).

Wasserman et al., Nat. Genet., 26:225-228, (2000).

Yamada et al., Stem Cells, 20:146-154, (2002).

Wang et al., Molecular and Cellular Biology, 1996, vol. 16. No. 11, pp. 6313-6324.

Webster's Online Dictionary, "Interdiction" www.webster-dictionary.org/definition/interdiction accessed Jan. 17, 2005.

Yeh et al., "Neuralized functions as an E3 ubiquitin ligase during Drosophila development," Current Biology, 11:1675-1679, (2001).

Yeh et al., "Neuralized functions cell autonomously to regulate Drosophila sense organ development," The EMBO Journal, 19(17):4827-4837, (2000).

Yuh et al., "Modular cis-regulatory organization of Endo16, a gut-specific gene of the sea urchin embryo," Development, 122:1069-1082, (1996).

Yuh et al., Patchy Interspecific Sequence Similarities Efficiently Identify Positive cis-Regulatory Elements in the Sea Urchin, Developmental Biology, 246:148-161, (2002).

Yuh et al., Development, 128:617-629, 2001.

Yuh et al., Science, 279:1896, (1998).

Zhu et al., "A large-scale analysis of mRNAs expressed by primary mesenchyme cells of the sea urchin embryo," Development, 128:2615-2627, (2001).

Figure 6
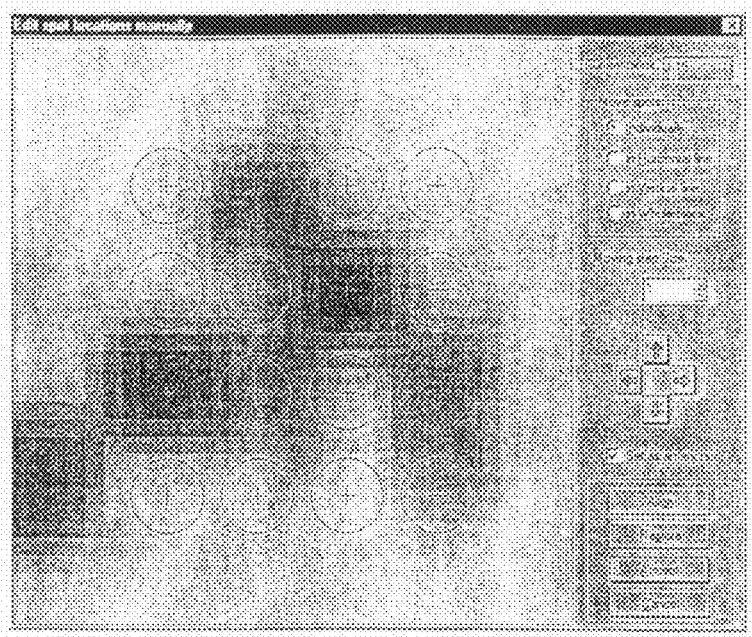
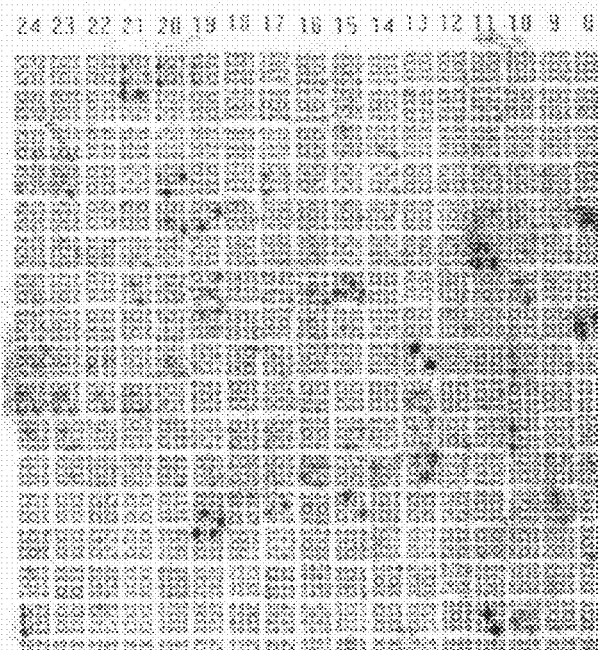
Figure 7

Figure 11
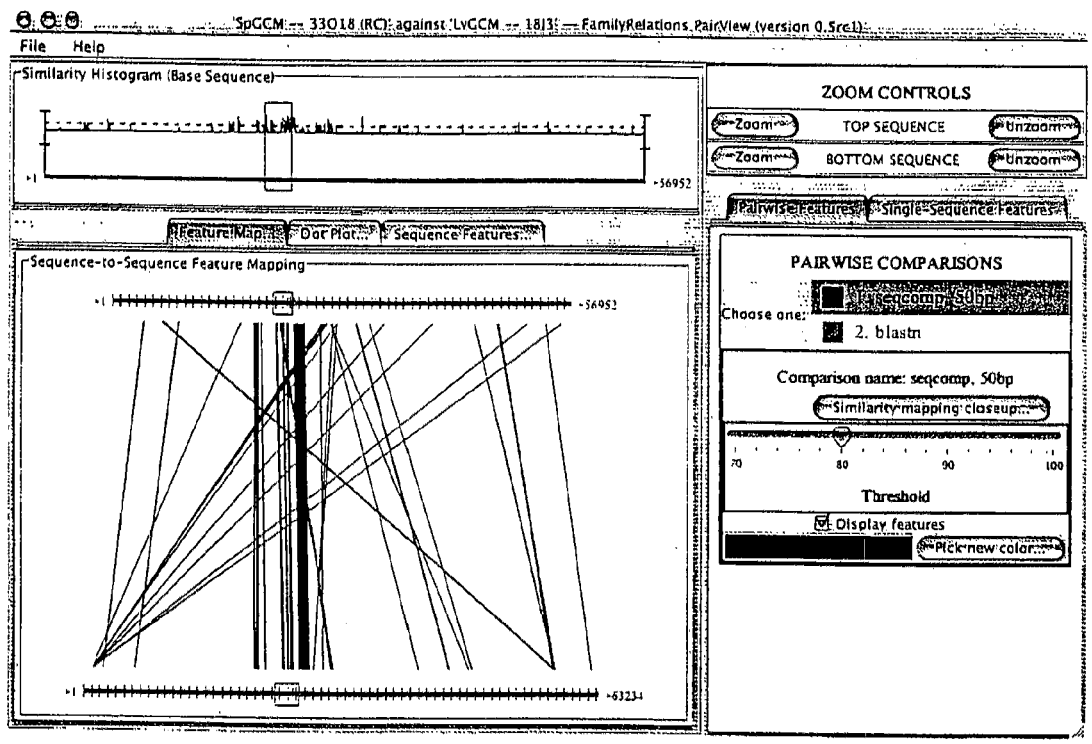
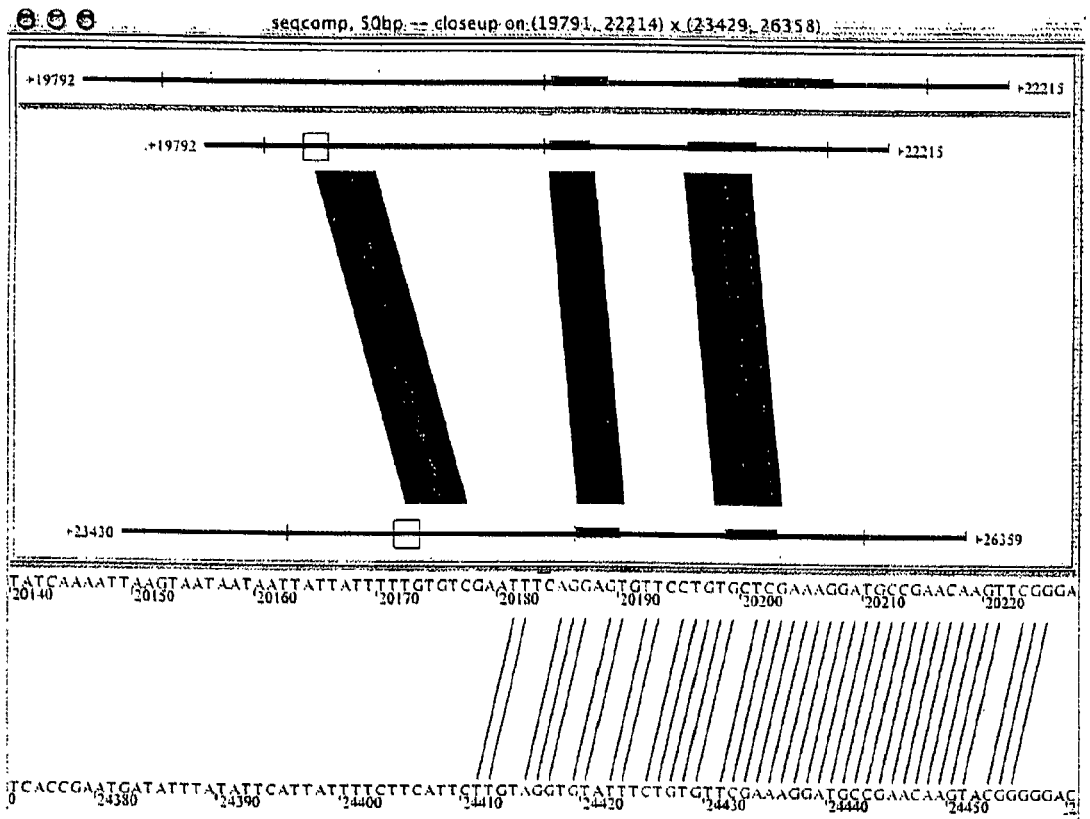
Figure 12

Figure 14A
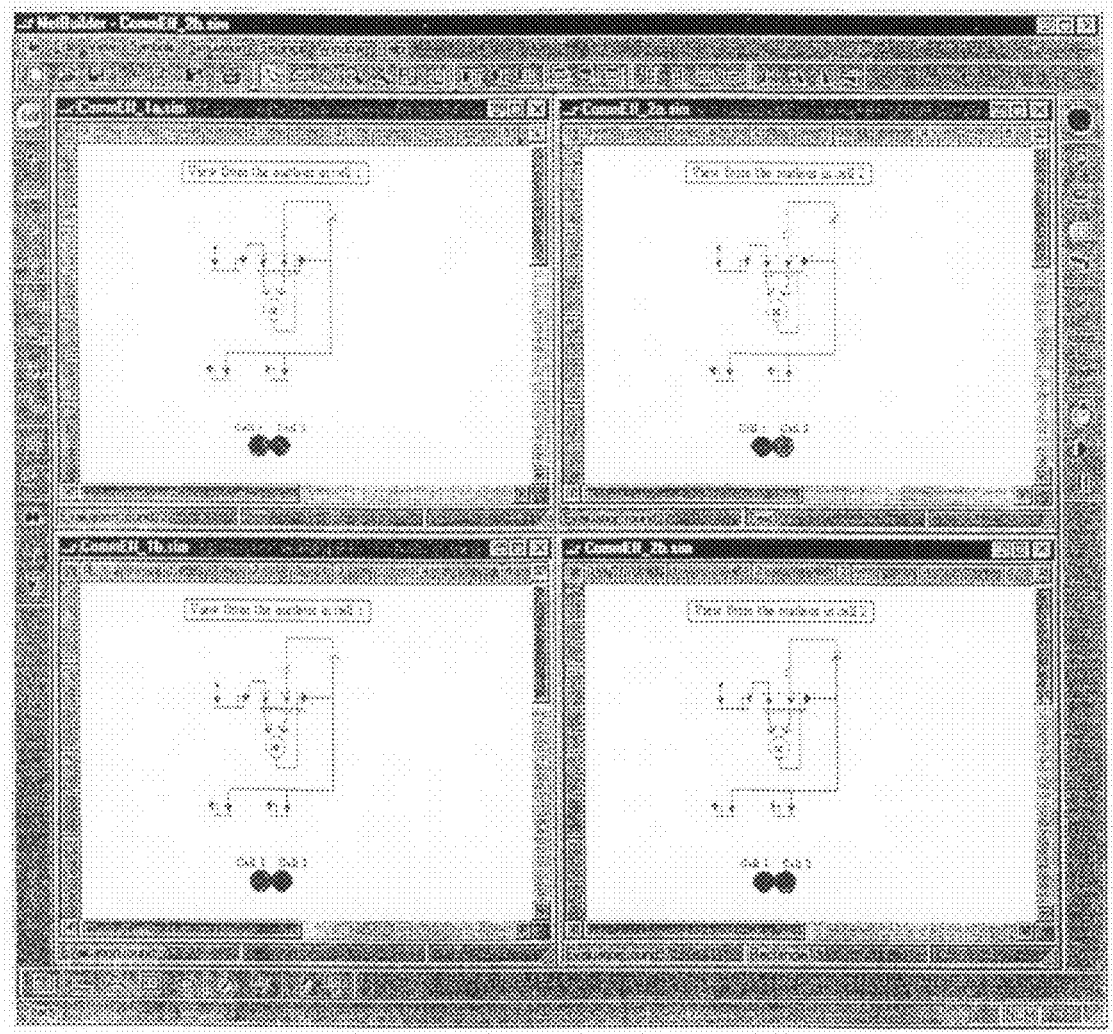
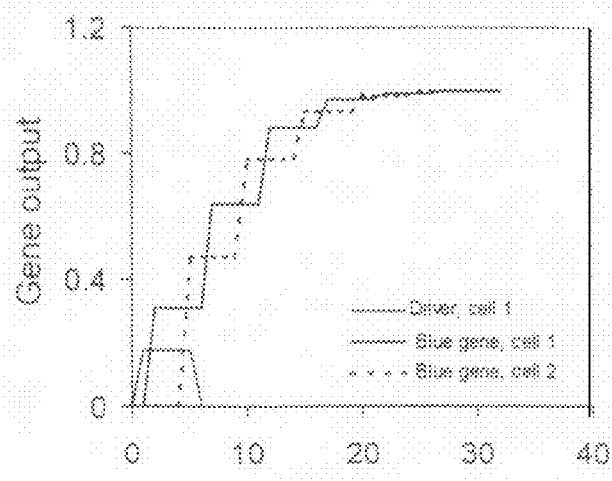
Figure 14B

US 8,178,347 B2

GENE REGULATORY NETWORKS AND METHODS OF INTERDICTION FOR CONTROLLING THE DIFFERENTIATION STATE OF A CELL

This application is a continuation application of U.S. Ser. No. 10/452,766, filed on May 30, 2003, which claims benefit of the filing date of U.S. Provisional Application No. 60/384,962, filed May 30, 2002 and which is explicitly incorporated herein by reference in its entirety.

This invention was made with government support under grant numbers HD-37105 and RR-06591 awarded by the National Institutes of Health. The United States Government has certain rights in this invention.

BACKGROUND OF THE INVENTION

This invention relates generally to cell fate decisions that underlie cell differentiation and tissue development repair, remodeling and renewal and, more specifically, to the modulation of the genetic regulatory architecture that determines cell fate for diagnostic and therapeutic interdiction.

Cell fate determination constitutes a complex series of intracellular and intercellular interactions. Within a cell, decisions must be made that turn on and off regulatory molecules and signals must be coordinated to achieve a concerted effect of the batteries of regulatory molecules in order for cells to appropriately differentiate. The genetic programming of cell fate requires both spatial and temporal coordination of the regulatory molecules within the nucleus of the cell in order to achieve a single, concerted outcome at any particular stage during cellular differentiation.

The complexity of regulatory signals and the coordination of such signals increase substantially in the context of the development of an organism or the development, repair, renewal or remodeling of a tissue. Intercellular regulatory interactions that regulate the spatial coordination of groups of cells and tissues additionally have to be included in the genetic program. Such a higher order level of complexity is immense when it is understood that the regulation necessarily requires spatial coordination in a three dimensional space and simultaneous temporal coordination of many different and diverse populations of cells within the organism or tissue over long periods of time. The ability to control the fate of a cell or population of cells at each stage of the differentiation and development process, and later during repair, renewal or remodeling, would have a significant impact on the diagnosis and therapeutic intervention of diseases.

Various efforts have been made to control the fates of uncommitted cells such as embryonic stem cells, stem cells in mature tissues and other progenitor cells. However, such approaches have shed only minimal light on the intricate genetic program and regulatory circuitry involved in the adoption of cell fate decisions. For example, pluripotent and progenitor stem cells have been studied for their ability to adopt the fade of, and differentiate into various terminally differentiated lineages. Factors and culture conditions have been identified by laborious trial and error that induce such cells adopt a certain fate and to preferentially move down a particular differentiation path. However, differentiation into pure populations of a desired cell type has yet to be obtained. Moreover, because confirmation of differentiation state is determined through phenotypic observation or by monitoring only a selective number of known markers, the other cellular activities not apparent by these measures remain unknown. Therefore, the exact regulatory or differentiation state will similarly be unknown and of limited value for harnessing the full diagnostic or therapeutic potential modulation of controlling cell fate.

Regulatory factors also have been identified that induce various aspects of cell differentiation, tissue or organism development or tissue repair, remodeling or renewal. Functional determination of such regulatory factors has occurred by the step-wise study of each factor and its target gene or genes. However, because of the amount of time and labor involved in such efforts, the completeness and intricacy of the overall regulatory program and circuitry at the cellular or organismic level is necessarily limited. The study of individual molecules and isolated regulatory loops is therefore inefficient and also leaves open the undesirable potential effect of undetermined aspects of these processes if used for purposes of diagnosis or therapeutic intervention.

Accordingly, absent characterization of the genetic regulatory system as a whole for the spatial and temporal complexity of cell fate decision and the resulting differentiation, development, repair, remodeling and renewal processes, the authenticity and reliability of any regulatory map will be insufficiently complete for confident use in the diagnosis and treatment of diseases.

Thus, there exists a need for the identification and compilation of the genetic regulatory architecture of a cell and for different cellular states in the differentiation, developmental, repair, remodeling and renewal processes which will allow for accurate interdiction and modulation of these cellular processes. The present invention satisfies this need and provides related advantages as well.

SUMMARY OF THE INVENTION

The invention provides a method of modulating a regulatory state of a cell. The method consists of: (a) identifying a point of interdiction within a cis regulatory network specifying a genetic regulatory architecture of a cell, and (b) introducing into a progenitor cell two or more network elements within said network to induce a predetermined series of cis regulatory network interactions resulting in a specified regulatory state of said progenitor cell. Also provided is a method of modulating a regulatory state of a cell. The method consists of: (a) identifying a point of interdiction within a cis regulatory network specifying a genetic regulatory architecture of a cellular state, and (b) introducing into a progenitor cell two or more network elements within said network to induce a predetermined series of cis regulatory network interactions resulting in a specified regulatory state of said progenitor cell. A cell having a specified regulatory state consisting of a modified genetic regulatory architecture is further provided. Methods of diagnosing and methods of treating an individual suffering from a cellular defect also are provided. The invention additionally provides a method of identifying a compound having differentiation or cell fate inducing activity.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 2A shows the genetic regulatory architecture for the $veg_2$ endomesoderm and micromere nuclei from about the fourth to seventh cleavage regulatory state. FIG. 2B-G show whole-mount in situ hybridization displays of various markers and developmental cell types.

FIG. 6 shows a view of the fine tuning spot evaluation masks in BioArray.

FIG. 7 shows a view of a filter image before (left) and after (right) fully automatic evaluation by BioAray.

FIG. 11 shows a comparison of BAC sequences surrounding the gcm gene in S. purpuratus and L. variegatus as displayed in FamilyRelatiions.

FIG. 12 shows a close-up view of the region enclosed by the blue boxes in FIG. 13.

FIG. 14A shows a "view from the nuclei" of cells during simulation with NetBuilder and FIG. 14B shows a time-course activities plot for the circuit in FIGS. 13 and 14A with NetBuilder.

DETAILED DESCRIPTION OF THE INVENTION

Figure 1:
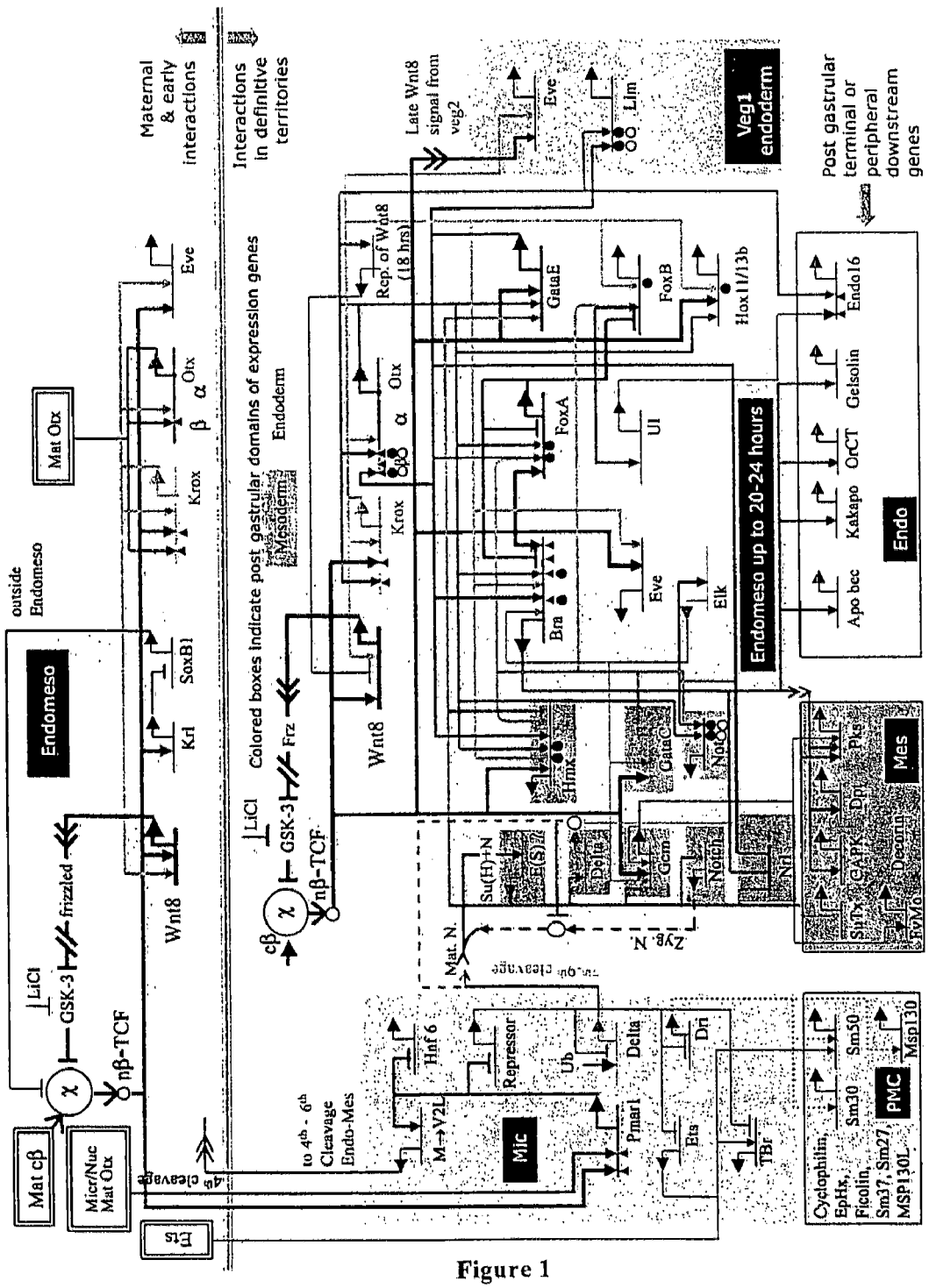
FIG. 1 shows the genetic regulatory architecture for endomesoderm specification.

This invention is directed to the identification and construction of the genetic regulatory architecture of a cell. The regulatory architecture consists of a cis regulatory network which describes the temporal and spatial connections between transcription factors and signaling elements and a system of target cis sequences that regulate other transcription factors controlling differentiation and development. A description of the genetic regulatory architecture constitutes a roadmap of the diverse number of connections between cis regulatory elements signaling components and trans acting factors that allows for the identification of controlling points in the spatial or temporal arrangement of cell fate decisions leading to cellular differentiation, organismal development, tissue repairing, remodeling or renewal. One advantage of such a roadmap is that it allows for the precise interdiction at the genetic or polypeptide level for modulation of the genetic programming. The genetic regulatory architecture can be used as a blueprint for assessing a regulatory or differentiation state of a cell, organism or tissue. Alternatively, the architecture can be used as a blueprint for targeting controlling points or branch junctures in differentiation, developmental, tissue repair, remodeling or renewal processes so as to direct a cell or population of cells into a predetermined lineage, tissue or organismal developmental state, or to prevent them from entering such lineage, tissue, or development states.

The invention is related to the identification of transcriptional and signaling elements for embryonic development. Development of the body plan is controlled by large networks of regulatory genes. A gene regulatory network that controls the specification of endoderm and mesoderm was deciphered using large-scale perturbation analyses of the developmental system, in combination with computational methodologies, genomic data, cis-regulatory analysis, and molecular embryology. The network contains over 40 genes and each node can be directly verified at the DNA sequence level by cis-regulatory analysis. The network's architecture reveals specific and general aspects of development, such as how given cells generate their ordained fates in the embryo and why the process moves forward in developmental time.

The invention is related to modulating the cell fate decisions that are controlled by gene regulatory networks in which genes encoding transcription factors or signaling elements interact with one another to determine spatial and temporal regulatory states of a cell. These networks are encoded in the genomic DNA as the signaling elements or trans-acting transcription factors and as the cis regulatory target sites that direct expression of each relevant regulatory gene. Controlling points or branch junctures leading to cell lineage commitment can be employed as points of interdiction to direct a cell or population of cells into, or away from, a predetermined path of differentiation, development, tissue repair, remodeling or renewal of a cell, tissue or organism.

In another embodiment, a cis regulatory network specifying the genetic architecture of a cell or cellular state is employed as a diagram of the genetic circuitry from which to determine the regulatory genes encoding a central portion of a targeted network. Expression of the identified regulatory genes are modulated to generate cells of the desired regulatory state from either eudogenouse, in site populations, or isolated populations of uncommitted cells. Modulation can be accomplished by, for example, using nucleic acid constructs expressing the transcription factor or factors that activate determinative controlling points or branch junctures. The nucleic acid constructs can be controlled by, for example, inducible expression systems, constitutively active expression systems or expression systems that respond to regulatory inputs already present in the initially uncommitted cells or to regulatory inputs that become activated during development or differentiation. Alternatively, the modulation can be achieved by, for example, using upstream regulators of the identified regulatory genes such as hormones, growth factors and other cell signaling molecules or functional equivalents thereof. Modulatory nucleic acid constructs can be introduced into the uncommitted cells for expression of the encoded regulatory factors with concomitant steering of the cell down the intended developmental or differentiation pathway. Modulation of regulatory genes and cis elements also can be accomplished using, for example, various effector molecules known in the art such as RNAi, small molecule compounds and antisense nuclear acids.

As used herein, the term "regulatory state" is intended to refer to active set of genetic connections of cis regulatory nucleic acid sequences or modules and transcription and signaling factors in a cell. A regulatory state therefore describes the relationship of genetic regulatory elements in a cell at a given cellular state and thus delineates a genetic regulatory architecture of a cell at a point in time. The term also can describe a genetic regulatory architecture of a cell or group of cells over a period of time and can include, for example, changes or relative differences between elements or cell states. Therefore, the term as it is used herein can include temporal order as well as spatial order of active connections within a genetic regulatory architecture. Active connections can correspond to, for example, the expression level or rate of synthesis of a transcription factor, the binding activity of a transcription factor to a cis regulatory sequence or module, or a combination of such measurements. Other measurements or attributes of active genetic connections well known to those skilled in the art can similarly be used to indicate connectivity between elements of a regulatory state. Transcription factor and signaling elements of a regulatory state can include, for example, exogenous factors, such as those derived from an external signal or source, or endogenous factors, such as those that result from a genetic connection which activates or represses production of a transcription factor element. Specific examples of a regulatory state include the genetic regulatory events specifying endomesoderm specification shown in FIG. 2, and the institution of regulatory lock-down activities specifying the complete activation of the endomesodermal regulatory system shown in FIG. 3.

The term "differentiation state" is intended to refer to the active set of genes within a given regulatory state. Such genes operate, for example, to control one or more function of a cell or group of cells in a particular regulatory state. A differentiation state therefore describes the relationship of genetic regulatory elements and the products they control in a cell at a given cellular state. Similarly, the term also can describe an active set of genes within regulatory states over a period of time including, for example, changes or relative differences between gene levels, activities or both. Therefore, the term can include, for example, temporal order as well as spatial order of gene set activity. Active genes can correspond to, and be determined by, for example, gene expression levels or rates; gene product levels, activity, or synthesis rates; or a combination of such measurements. Other measurements or attributes of gene activity or function well known to those skilled in the art can similarly be used to indicate an active gene set or relationship within a given regulatory state. Active genes of a regulatory state can include, for example, those genes or batteries of genes that control a particular cell function. Specific examples of gene sets specifying a function within a regulatory state include are described in Example I below and the references cited therein and in U.S. Ser. No. 60/384,962.

Other examples of gene sets specifying a function within a regulatory state include the gene sets specifying the differentiation state of mammalian brain dopamine neurons, the differentiation state of mammalian hepatocytes and the differentiation state of mammalian pituitary somatotropes. Briefly, the differentiation state of mammalian brain dopamine neurons includes, for example, an increase in the transcription of the genes encoding tyrosine hydroxylase (TH), L-amino acid decarboxylase (AADC), and dopamine transporter (DAT), and in the expression of the encoded proteins (Kim et al., *Nature* 418, 50-56, 2002). The differentiation state of mammalian hepatocytes includes, for example, increased transcription of the genes for albumin, transthyretin (TTR), hepatocyte nuclear factor 3 beta (HNF3β), alpha-1-antitrypsin (a-1-AT), tryptophan-2,3-dioxygenase (TDO), urea cycle enzyme, gluconeogenic enzyme, and liver-specific anion transporter-1 (LST-1), and an increase in expression of the encoded proteins (Yamada et al., *Stem Cells* 20, 146-154, 2002). Further, the differentiation state of mammalian pituitary somatotropes includes, for example, an increase in the transcription of the growth hormone (GH) gene, and in the expression of GH (Scully and Rosenfeld, *Science* 295 2231-2235, 2002).

Figure 2:
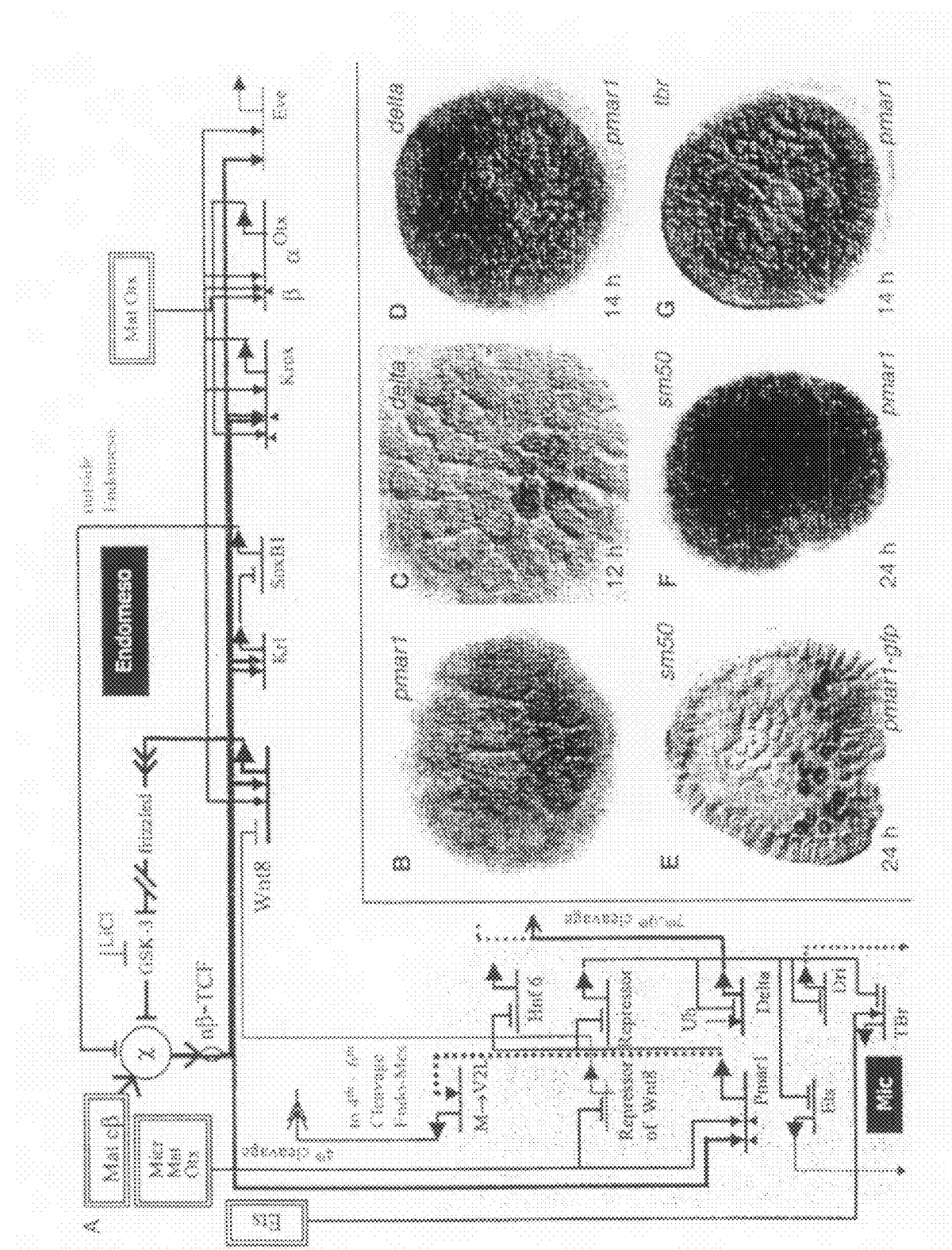
FIG. 2 shows the initial genetic regulatory events in endomesoderm specification.
Figure 3:
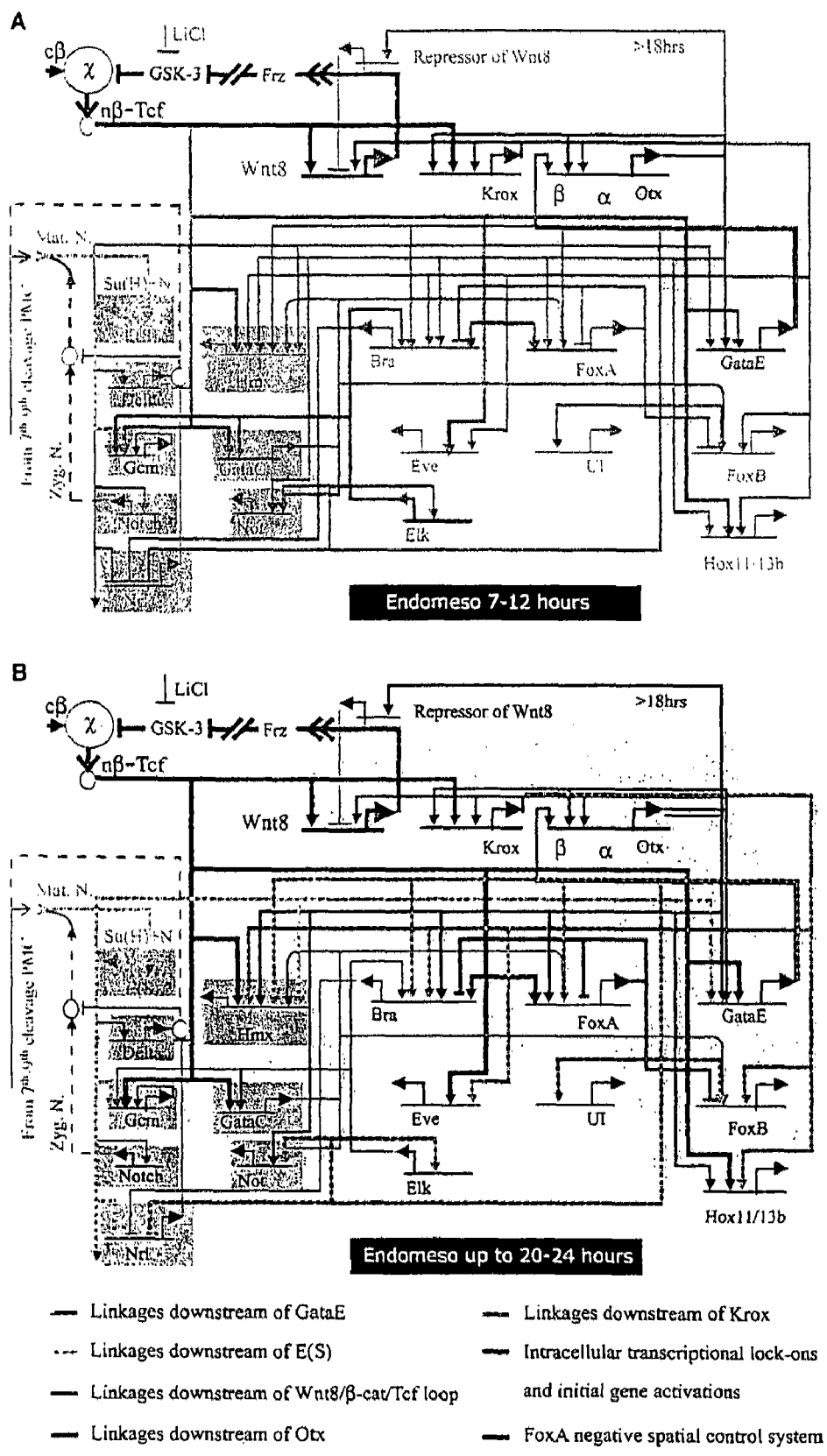
FIG. 3 shows the genetic regulatory architecture for the regulatory state instituting regulatory lock-down activities (FIG. 3A) and for the complete activation of the endomesodermal regulatory system (FIG. 3B).

As used herein, the term "cis regulatory network" is intended to mean a collection of cis regulatory nucleic acid sequences or modules and transcription or signaling factors that are interrelated by binding activity and perform a common function. Binding interrelations of cis regulatory network elements or components include transcription factors and their cognate cis regulatory nucleic acid sequences or modules. A cis regulatory network can include, for example, cis regulatory binding connections for a particular cellular function, or related cellular functions, or for an entire cell, population of cells, tissue or organism or a subcomponent thereof. The term as used herein can refer to, for example, the total number of connections of cis regulatory modules and transcription or signaling factor elements or to subsets of connections such as those active cis regulatory connections so long as the grouping of network elements maintains a relationship of common function. The term similarly can include temporal or spatial order of cis regulatory connections or both. Accordingly, a cis regulatory network can be represented as a static view or a dynamic view. Specific examples of a cis regulatory networks are shown in FIGS. 1-3.

As used herein, the term "genetic regulatory architecture" is intended to mean the organizational structure of elements and the connections between them within a cis regulatory network. A genetic regulatory architecture represents, for example, an arrangement or map of the binding activities, connections and resultant functions or gene products of a collection of interrelated transcription factors and their cognate cis regulatory nucleic acid sequences or modules that perform a common function. The organizational structure can contain a single or multiple cis regulatory networks as well as contain networks within or between regulatory territories. Therefore, a genetic regulatory architecture can represent any cis regulatory network including, for example, a cis regulatory network of a cell, tissue or organism, a cellular state, or a differentiation state. The organizational structure can be represented in a variety of different formats such as by nodes and edges or by other graphic or analytical methods well know to those skilled in the art. Specific examples of useful representations of genetic regulatory architectures are shown in FIGS. 1-3.

As used herein, the term "network element" is intended to mean a molecular constituent of a cis regulatory network. Such molecular constituents include, for example, polypeptides, such as transcription factors, signaling elements and nucleic acids, such as cis regulatory sequences and modules as well as other macromolecules or biochemical molecules that are constituents of a biochemical system such as a cis regulatory network. Such network elements can be represented by, for example, a node or edge or other graphical representation that conveys the identity of the component, binding connectivity, directionality and activity of the element. Other functions, characteristics and attributes of the network element can additionally be incorporated into the representation of the element depending of the desired need or use of the cis regulatory network.

As used herein, the term "cis regulatory network interaction" is intended to mean a binding event between network elements of a cis regulatory network. Binding events can be between, for example, a transcription factor and a cis regulatory sequence or module as well as between signal transduction molecules or messengers and transcription factors, cis regulatory sequences, cis regulatory modules and any combinations thereof. The binding event can result, for example, in activation, deactivation, augmentation, or repression of the bound target network element or gene controlled by the bound target network element. Network interactions can be directional, reversible or essentially irreversible, for example, depending on the thermodynamics and biochemical properties of the interacting species.

Accordingly, a "series" of cis regulatory network interactions is intended to mean a directional flow of two or more binding events between network elements. Such binding events can occur, for example, in contiguous or sequential spatial or temporal order within a cis regulatory network or subnetwork. Alternatively, element binding interactions can occur spatially or temporally non-contiguous or non-sequential within a network or subnetwork. Specific examples of cis regulatory network interactions include each of the binding interactions shown in FIGS. 1-3. Specific examples of series of network interactions include, for example, those interactions in FIGS. 1-3 where there is an input edge to a node and a resultant output edge or activity.

As used herein, the term "cis regulatory module" is intended to mean a collection of cis regulatory nucleic acid sequences elements that form a cis regulatory domain of a gene. Core nucleotide sequences of cis elements that confer binding activity for a transcription factor or signaling element constitute a cis regulatory nucleic acid sequence element. Combinations of such elements strung together constitute cis regulatory modules. Such higher order combinations impart additional regulatory complexity and specificity onto their associated gene allowing diverse combinations of input signals to differentially control either the spatial or temporal expression or both of the associated gene. Cis regulatory sequence elements and modules are well known to those skilled in the art and can be found described in, for example, Kirchhamer and Davidson, *Development* 122:333-346 (1996); Yuh and Davidson, *Development* 122:1069-1082 (1996) and Davidson, E. H., *Genomic Regulatory Systems: Development and Evolution* Academic, San Diego (2001).

As used herein, the term "predetermined" when used in reference to a series of cis regulatory network interactions is intended to mean that the order and events constituting the series of interactions are determined, resolved or settled in advance of a referenced action. Therefore, the term is intended to impose knowledge of a direction or tendency on a series of cis regulatory network interactions before instituting an initiating action.

As used herein, the term "progenitor" or "progenitor cell" is intended to mean a cell that can give rise to a different cell type or to a cell having a different regulatory state or differentiation state. A progenitor or progenitor cell therefore references a cell that is an originator or precursor of a different cell type or of a cell having a different regulatory or differentiation state. Because development, differentiation and cis regulatory systems can be modulated in both forward and reverse directions using the methods of the invention, the term as it is used herein, is intended to include both non-terminally differentiated and terminally differentiated cells. For example, a progenitor cell of a terminally differentiated cell can be an embryonic cell, a stem cell, an uncommitted progenitor cell, a lineage specific stem or progenitor cell or a lineage specific committed progenitor cell. Conversely, the progenitor cell of any of these non-terminally differentiated cells can be, for example, a terminally differentiated cell or a cell having a less differentiated state. In the former example, the non-terminally differentiated progenitor cells can be induced to differentiate in the forward direction into a terminally differentiated cell. In the latter example, an already terminally differentiated progenitor cell can be induced to dedifferentiate into a non-terminally differentiated cell.

As used herein, the term "regulatory territory" is intended to mean a spatial, temporal or functional category of a cis regulatory network. A regulatory territory can be, for example, either intracellular or intercellular. Such intracellular regulatory territories can include, for example, different cis regulatory networks or subnetworks within a cell or population of cells, distinguishable by a spatial, temporal or functional nexus. Specific examples of intracellular regulatory territories include the different regulatory states of a cell as it progresses from one differentiation state to another. Similarly, intercellular regulatory territories can include, for example, different cis regulatory networks or subnetworks different between cells of a population, tissue or region of an organism that are distinguishable by a spatial, temporal or functional nexus. Specific examples of intercellular regulatory territories include the different regulatory states of different tissues or presumptive tissues at a given point during differentiation or at different points during differentiation. Such presumptive or actual tissues include, for example, a zygote, a primary germ layer, endoderm, mesoderm, ectoderm and a terminally differentiated cell.

As used herein, the term "exogenous" used in relation to a transcription or signaling factor is intended to mean that the referenced cis regulatory network element or encoding nucleic acid originates or is derived from outside of the existing cis regulatory network, genetic regulatory architecture, cell, tissue or organism. The exogenous network element or encoding nucleic acid thereof can be either heterologous or homologous, in relation to the cell tissue or organism of the network element, to the referenced cis regulatory network, genetic regulatory architecture, cell, tissue or organism. The term includes the introduction of a heterologous element to confer a new component activity onto a referenced environment such as a cis regulatory network, genetic regulatory architecture, cell, tissue or organism as well as the introduction of a homologous element. The introduction of a homologous element can be used to confer, for example, either a new component activity which is not currently present in the referenced environment or to confer an increased amount or activity of an already present endogenous element onto a referenced environment. In contradistinction to an exogenous network element or encoding nucleic acid an endogenous network element or encoding nucleic acid will already be present in the reference environment.

As used herein, the term "non-naturally occurring" when used in reference to a regulatory state is intended to mean that the regulatory state differs by at least one component or activity from a regulatory state which is found to occur in one or more organisms found in the natural world. Naturally occurring regulatory states consist of those that occur in or are determined by nature and which are based upon the physiological or developmental operations of a cell, tissue or organism found in nature.

In one embodiment, the invention provides a method of modulating a regulatory state of a cell. The method consists of: (a) identifying a point of interdiction within a cis regulatory network specifying a genetic regulatory architecture of a cell, and (b) introducing into a progenitor cell two or more network elements within said network to induce a predetermined series of cis regulatory network interactions resulting in a specified regulatory state of said progenitor cell.

The genetic programming for organismal development and cellular differentiation is hardwired in genomic DNA because the specificity of the body plan is the cardinal heritable property of the organism. As large regulatory control systems organized as genetic networks, the lines of causality can be mapped from the genomic sequence to major processes of development and cellular differentiation including that of bilateral organismal. The heart of such cis regulatory networks consists of genes encoding transcription or signaling factors and the cis regulatory elements that control the expression of those genes. Each of the cis regulatory elements receives multiple inputs from other genes in the network, the inputs being transcription factors which bind to a specific element that contains a specific target site cis nucleic acid sequences. Functional linkages of which the network is composed are those between the outputs of regulatory genes and the sets of genomic target sites to which their products bind. These functional linkages which orchestrate in both a spatial and temporal fashion the differentiation fate and development plan of a cell or organism can be analogized to electronic circuitry, its associated switches, capacitors and resistors.

A cis regulatory network specifying the genetic architecture of a cell or cellular state can be employed as a wiring diagram of the genetic circuitry which identifies and sets forth the important regulatory genes encoded within a network. Methods for determining the genetic regulatory architecture and deciphering the cis regulatory network for a cellular or regulatory state are described in detail below in the Examples. Briefly, the methods involve a system analysis of perturbation of the cis regulatory elements and the transcription factors involved in the cis regulatory network. Conformation of functional regulatory linkages between the transcription or signaling factors and the cis regulatory elements can be performed by, for example, cis regulatory analysis. Such an approach proceeds by identifying the control elements and their target sites and then determining the functional significance of the linkage by any of a variety of methods well known to those skilled in the art.

Essentially, cis regulatory analysis is a "reverse-engineering" approach to functional determination of developmental and differentiation processes by analysis of the underlying regulatory inputs and outputs of the system. Cis regulatory analysis involves identifying the regulatory inputs and outputs throughout the genomic regulatory system that control the a developmental or differentiation process as it unfolds. Identification of such functional connections inherently describes the hierarchical functionality of the development and differentiation processes at each spatial or temporal stage. Once described, the inputs and outputs can be manipulated to achieve essentially any desired practical outcome.

Functional linkages of regulatory inputs and outputs can be assimilated or compiled into a written description of a cis regulatory network that diagrams the genetic circuitry. A diagram specifying cis regulatory connections irrespective of spatial or temporal activity describes the genetic architecture of functional linkages that are available to a cell or organism at any given point in differentiation or development. The genetic programming, through its cis regulatory network, turns on and off various circuits within this architecture throughout the development, differentiation and repair, remodeling or renewal processes to achieve precise biological outcomes. A specific example of a cis regulatory network specifying the genetic regulatory architecture of a cell for endomesoderm specification is shown in FIG. 1 and described below in the Examples.

In contrast, a diagram or other compilation specifying those cis regulatory connections occurring at a particular time or place will describe the precise genetic architecture of functional linkages that are active during that point of the development, differentiation, repair, remodeling or renewal processes. In short, these are the genetic circuits that are temporally and spatially active within the organism or cell at the time of the monitored event. The composite of spatial and temporal connections active during a particular developmental, differentiation, repair, remodeling or renewal processes is one characteristic of the genetic regulatory architecture that specifies the regulatory state of the cell. In turn, a regulatory state is a regulatory fingerprint that characterizes or can be correlated with its corresponding phenotypic cellular state. Specific examples of cis regulatory networks specifying the genetic regulatory architecture of several cellular states during endomesoderm specification are shown in FIGS. 2 and 3 and are described below in the Examples.

The interconnections specified in a cis regulatory network of the invention will consist of the binding interactions between the various network elements that are related by a common function. As described previously, these cis regulatory network elements will consist of transcription factors, cis regulatory elements and cis regulatory modules. The binding interactions can represent any activity of the included network elements and include, for example, one or more transcription factors binding to one or more cis elements or modules to effect activation or repression of the bound cis sequence. Similarly, binding activities can be interconnected by sequential or parallel interconnections induced by one or more initial binding activities to represent a consequential series of binding interactions that have been induced or repressed by a referenced binding activity.

Similarly, binding interactions of a cis regulatory network of the invention also can be specified in relation to one or more cis regulatory sequence binding activities or in relation to both the transcription factor elements and the cis sequence elements of cis regulatory network. The information conveyed and the binding activity of a particular element within a cis regulatory network is the same whether a particular element within a cis regulatory network is viewed as a binder or as a bindee because either viewpoint will show the constituent binding entities and the binding activity between them. Additionally, either viewpoint can be utilized to convey the resultant activity induced by the binder or bindee, whether it consists of, for example, activation, repression or attenuation of a gene or transcription factor.

A cis regulatory network compilation also can include interrelationships within a common function other than those binding activities between transcription factors and cis elements or modules. For example, a cis regulatory network of the invention can further specify activities of inducers, inhibitors or other types of regulators that initiate from external origins relative to the cis regulatory network. Similarly, activities of inducers, inhibitors or other types of regulators exported from a cis regulatory network following production also can be specified in a cis regulatory network of the invention. Such inducers, activators or regulators can include, for example, hormones, growth factors, second messengers, signaling ligands, ligands, and cofactors. Further, gene products of other than transcription factors also can be included in a cis regulatory network of the invention as well as all types of macromolecules, and molecules when desired to impart information on the function or activity of a cis regulatory network.

A cis regulatory network as well as a genetic regulatory architecture of the invention can specify interconnections of binding activity within or between two or more regulatory territories. Because a cis regulatory network of the invention specifies the activities and connections between regulatory elements involved in differentiation and development, it will consequently specify the binding activities of transcription factors and their cognate cis regulatory elements and modules between regulatory territories of a cell, population of cells, tissue or organism. Shown in FIG. 1, for example, are the interconnections of binding activity for endomesoderm specification. The top panel describes the binding activities of transcription factors and cis elements for maternal and early embryotic regulatory interaction. The bottom panel describes binding activities within and between regulatory territories.

The regulatory territories shown in FIG. 1 are delineated according to definitive territories of an embryo. Binding interactions are shown between, for example, early endomesoderm and the skeletogenic micromere and primary mesenchyme (PMC). Other binding interactions between regulatories shown in FIG. 1 include interactions between skeletogenic micromere and endomesoderm that is less than 24 hours of development (24 hour endomesoderm), 24 hour endomesoderm and skeletogenic micromere, 24 hour endomesoderm and mesoderm and vice versa, 24 hour endomesoderm and endoderm, and 24 hour endomesoderm and Veg$_1$ endoderm. Binding interactions between 24 hour endomesoderm and post-gastrula domains of mesoderm or endoderm also are shown. Other regulatory territories can include, for example, a zygote, a primary germ layer or a cell, tissue or organ. Interactions between regulatory territories include both spatial and temporal binding activities whereas interactions within a regulatory territory includes spatial binding activities between elements of the cis regulatory network. Details of the above and other binding interactions are described further below in the Examples.

Regulatory territories can be delineated by criteria other than developmentally defined territories. Those skilled in the art will know, or can determine, which constituents of a cis regulatory network define a regulatory territory. The categorization criterial can depend on the structure or function of a cis regulatory network and can include territories based on, for example, regulatory inputs or outputs, sets of genes that are regulated in concert, temporal occurrences, functional occurrences as well as based on differentiation or development functions. Moreover, given the teachings and guidance provided herein, it is not necessary to specify in advance, or categorize elements as belonging to, one or more regulatory territories for a cis regulatory network to be useful because the act of specifying the interconnections of transcription factors and cis regulatory elements will inherently describe regulatory territories of the cell, population of cells, tissue or organism. However, conceptualization or even categorization based on a user's objective of regulatory territories can facilitate the user of a cis regulatory network because such manipulations additional to specifying the underlying binding connections confer flexibility in the range of applications of a cis regulatory network.

Cis regulatory networks which specify a genetic regulatory architecture of a cell or cellular state can be utilized to modulate a regulatory state of a cell. Cis regulatory networks can be compiled into any of a variety of formats of data assemblies that are capable of describing interrelationships of component activities in time and space as would be well understood to those skilled in the art. Forms available for such representations include, for example, graphical, electronic, mathematical descriptions or composites that specify the inputs, outputs, spatial locations, temporal order of events, directionality and other attributes of the system and system components. Examples of graphical electronic representations are shown in FIGS. 1-3 where the components are represented by nodes, directionality by lines and activity by arrows, bars or other symbols. Other representations for such genetic architectures of cis regulatory network composites are well known in the art and can similarly be used describe the functional linkages of the genetic circuitry.

Once mapped in a diagram or other descriptive form, circuits controlling various functions of the network as a whole or of subnetwork are readily identifiable by following the inputs and outputs at any given state of development, differentiation, repair, remodeling or renewal. Transcription factors and their corresponding cis regulatory elements or modules initiating a particular circuit correspond to controlling points for that process. Such controlling points generally entail from one to a few network components to initiate the process. Branch junctures are controlling points within a network or subnetwork that initiate further downstream activity. The activities they effect can be located within their initiating network or can be within a spatially or temporally distinct network. As such, outputs of branch junctures can be an initiating signal or a controlling point for a distinct network.

In FIGS. 1-3, the controlling and branch points as well as all other interactions between transcription factors and cis regulatory elements are represented by nodes and edges. These graphical representations correspond to the transcription factor inputs, transcription factor-cis regulatory sequence binding activity and transcription factor or signaling element outputs that dictate the regulatory state of a cell. Modulation of a regulatory state of a cell involves, for example, disruption or forced activation of these interactions to prevent further signal production or to create entirely new signals. Depending on the point or points chosen for disruption or forced activation, one or many signals can be prohibited or enhanced, thus resulting in inhibition of from one to many different processes of the network. A differentiation, developmental, repair, remodeling or renewal process can therefore be enhanced, slowed or even stopped, depending on the disruption or enhancement.

Similarly, re-directing a few connections can result in augmentation or suspension of a particular function, whereas re-direction of many different circuits can result in a substantially new program leading to an entirely novel cell fate. Re-direction can involve, for example, turning on or off existing circuits or sets of circuits, bypassing existing circuits or adding new circuits to the cis regulatory network. Therefore, differentiation, developmental, repair, remodeling or renewal can be controlled, fine-tuned or substantially modified to direct the process down a predetermined outcome or path.

Any of the nodes or edges within a cis regulatory network can be utilized as points of interdiction for disrupting activating or re-directing the network. Depending on the desired outcome, one skilled in the art can determine nodes or edges from a cis regulatory network that correspond to controlling points or branch junctures sought to be modified to achieve a particular result. Viability of the disruption or rewiring can be determined, for example, by ensuring that the unaffected functional linkages are sufficient to carry out their functional load in light of the intended modification. Therefore, given a cis regulatory network, both the viability and utility of any modification of the network to achieve a desired and predetermined result can be assessed and determined at the design level. For example, the network can simply be re-directed as assessed and desired given the knowledge of the functions and connections for whether the signals sufficient to achieve a particular function will be maintained so as to confer to modified function onto the system.

Points of interdiction can be designed, for example, to intervene early or late in a developmental, differentiation, repair, remodeling or renewal process. Unless the point of interdiction is the penultimate step in a terminal differential pathway, the design will impart a series of network interactions within the cis regulatory network. Such multiple interactions can occur within a spatially or temporally similar network or subnetwork or within a spatially or temporally distinct network. The magnitude of altered interactions will depend on, for example, the predetermined result to be obtained and whether the chosen point of interdiction is proximal or remote to the desired outcome. The more distal to the desired outcome, the more circuits will have to be assessed at the design level to ensure unmodulated functions are maintained. The converse is true for when a more proximal intervention point is chosen.

Those skilled in the art will understand that it is not necessary to design or implement perfect interventions to achieve a desired and predetermined outcome. Given the complexity of a cis regulatory system, it should be appreciated that there will be many instances where intervention at a controlling point or branch juncture will, in addition to achieving a desired modification, also impart undesirable effects within other circuits of the network or within related subnetworks. Those skilled in the art also will understand that, given a regulatory flow diagram such as a cis regulatory network, it is a routine matter to implement corrective interventions that substitute for, or neutralize, the undesirable effects incurred in the primary intervention. Therefore, compensatory alterations can be made that either replace, substitute or supplement the primary intervention in a cis regulatory network in order to achieve the specifically designed regulatory state.

Exemplary points of interdiction to achieve a predetermined change in regulatory state include, for example, Krox, Otx, GataE, Tcf, and enhancer of split-like factor. Interdiction can occur at these points or downstream from these points, for example, to circumvent their regulation. Other points of interdiction include, for example, Nkx2.5, GATA family members, including GATA6, Mef2, αHAND and Tbx5, which control cardiac cell fate. Other exemplary points of interdiction include, for example, introduction of the mRNA for Pmar1 into non-committed embryo cells to produce mesomere (skeletal) cells (Davison, et al., *Science* 295, 1669-1678, 2002). Transfection of nurr-1 into mammalian stem cells, and subsequent treatment exposure to exogenous fibroblast growth factor 8 (FGF8) to produce dopamine neurons (Kim et al., supra) or the knockout of the Indian hedgehog (Ihh) and smoothened (Smo) genes to prevent the formation of blood islands (blood vessel precursors) in mammalian embryos (Byrd et al., *Development* 129, 361-372, 2002). Further, points of interdiction can be readily determined by, for example, constructing a cis regulatory network and identifying controlling or branch points given the teachings and guidance provided herein. Moreover, cis regulatory networks and points of interdiction exemplified in the species described herein can be extrapolated to, and implemented in other species, including human.

Once the network modifications have been determined with respect to the cis regulatory network compilation, they can be implemented in a cell, tissue or organism using a variety of methods well know to those skilled in the art. Because the cis regulatory network is based on encoded nucleic acid transcription factors and cis elements or modules, any method that allows the expression of a polypeptide or the introduction of a nucleic acid carrying a target cis element or module can be employed to impart the new regulatory design. For example, modulation can be accomplished by using nucleic acid constructs expressing the transcription factor or factors that activate or repress determinative controlling points or branch junctures. Nucleic acid constructs that introduce cis regulatory sequences as inhibitors themselves or as effectors when utilized to regulate the expression of a desired transcription factor can also be used.

The nucleic acid constructs can be controlled by, for example, inducible expression systems, constitutively active expression systems or expression systems that respond to regulatory inputs already present in the initially uncommitted cells or to regulatory inputs that become activated during development or differentiation. Alternatively, the modulation can be achieved by, for example, using upstream regulators of the identified regulatory genes such as hormones, growth factors and other cell signaling molecules or functional equivalents thereof. Combinations and permutations of these and other methods for implementing the design modifications also can be employed given the teachings and guidance provided herein. Modulatory nucleic acid constructs can be introduced into the target cell for expression of the encoded regulatory factors with concomitant steering of the cell down the intended developmental or differentiation pathway.

Modulating a regulatory state of a cell will generally constitute introducing two or more network elements into a cell to induce a predetermined change in the cis regulatory circuitry. However, in some designs a desired regulatory state can be achieved through introduction of only one network element such as a transcription factor or cis element or module. In other designs, achieving a desired regulatory state will require from several to many network element changes. As described previously, the number of interdictions and alterations in the cis regulatory network necessary to impart a particular function will be determined, in part, by the network proximity to the end result, the complexity of the network or subnetwork being interdicted and by the amount of replacement or supplemental interdictions required to maintain other desired functions of the system. Once modified, the newly introduce network elements will perform their transcription regulatory functions by binding to or being bound by their cognate cis elements or transcription factors to initiate a series of cis regulatory network interactions that were predetermined at the design stage. The series of interactions can be activation, repression or both activation and repression of two or more network elements. The result of such interactions will be to produce a cell having the specified regulatory state of the underlying modified cis regulatory network.

Points and elements of interdiction include any component contained within the cis regulatory network. For example, the points of interdiction can be a cis regulatory element or module which can be bound by a transcription factor or set of transcription factors. The cis regulatory element or module can be chosen to control expression of a transcription activator or transcription repressor. Similarly, the activators or repressors can function to lock down and commit a regulatory state, to prohibit commitment or to invoke a new direction of differentiation or development. Directionality can be altered either by moving toward lineage and terminally differentiated states or by dedifferentiating a progenitor cell.

Alternatively, the point or points of interdiction within a cis regulatory network also can involve, for example, a transcription factor. The transcription factor can be an activator or repressor. The transcription factors can be chosen, for example, to bind to a cognate cis element or module and modulate the expression of a linked regulatory gene. Similarly, the transcription factors themselves can function to lock down, prohibit or invoke a specified regulatory state. Various combinations of cis regulatory elements or modules and transcription factors also can be selected as sets of interdiction points to achieve a specified result. Depending on the design modifications, the network elements chosen as points of interdiction can be invoked upstream of control points or branch junctures to activate or inhibit downstream elements or invoked downstream of a control points or branch junctures to circumvent a particular regulatory node. Given the teachings and guidance provided herein, those skilled in the art will known or can determine an appropriate point or points of interdiction and the complimentary network elements which can be used to effect a desired modification in the cis regulatory network to achieve a specified cell regulatory state.

The orchestrated series of gene activations and repressions that implement a particular interdiction will constitute different regulatory states of the cis regulatory network. A resting point in such an induced series of cis regulatory network interaction changes will correspond to the progenitor cell regulatory state specified by the interdiction design. Because a regulatory state also delineates a genetic regulatory architecture of a cell at a given point in time, a resting point also will characterize the cellular state of a progenitor cell induced by the interdiction. The resting point can be, for example, transient, stable or permanent depending on the initial progenitor cell used and the predetermined series of interactions designed to be induced. Similarly, those genes that are active at the resting point represent the new differentiation state of the cis regulatory network. Various differentiation states corresponding to particular stages of endomesoderm specification are shown in FIGS. 1-3 and described further below in the Examples.

Interdictions within a cis regulatory network to modify a regulatory state of a cell can be performed in essentially any desired type of cell, tissue or organism. In essence, any cell or group of cells can be reprogrammed to generate a different cell of a desired regulatory state. By choosing an interdiction point or points as described above, a progenitor cell can be induced to move forward or backwards along a differentiation or developmental pathway. A progenitor cell also can be induced to change regulatory states without altering its physiological differentiation or developmental characteristics. For example, an undifferentiated or less differentiated cell can be reprogrammed by introduction of cis regulatory network elements to differentiate. Conversely, a differentiated or more differentiated cell can be modified by introduction of cis regulatory elements to dedifferentiate.

Various types of cells that can be reprogrammed into a specified regulatory state include, for example, a zygote, a pluripotent stem cell, a pluripotent lineage specific progenitor cell, a progenitor cell or a terminally differentiated cell. Progenitor cells used in the methods of the invention can be derived from any tissue harboring such cells. Further, given the available methods well known to those skilled in the art, a progenitor cell can be reprogrammed by either ex vivo, in vivo, or in situ. Cis regulatory network elements can be introduced, for example, into a single progenitor cell, a population of progenitor cells, progenitor cells within tissues, organs or organisms or whole populations of progenitor cells constituting a tissue, organ or organism. Those skilled in the art will known what format of element introduction is appropriate for a given application. For example, where a reprogrammed progenitor cell can be implanted or transplanted method for ex vivo modification can be used effectively. In contrast, in vivo or in situ modification can be effectively used where vectors and targeting moieties are available for the progenitor cell.

Therefore, the invention provides a method of modulating a regulatory state of a cell. The method consists of: (a) identifying a point of interdiction within a cis regulatory network specifying a genetic regulatory architecture of a cellular state, and (b) introducing into a progenitor cell two or more network elements within said network to induce a predetermined series of cis regulatory network interactions resulting in a specified regulatory state of said progenitor cell.

Also provided is a cell having a specified regulatory state, comprising a cis regulatory network having a modified genetic regulatory architecture, said modification comprising two or more exogenous transcription factors activating a predetermined series of cis regulatory network interactions, said series of cis regulatory network interactions resulting in a specified non-naturally occurring regulatory state of said cell.

Progenitor cells can be reprogrammed by design and interdiction, for example, to generate a newly specified genetic regulatory architecture or to generate a newly specified regulatory state within an existing genetic regulatory architecture. The desired end point will determine whether a new binding interactions between transcription factors and their cognate cis regulatory elements are required or whether activation, repression or both activation and repression will suffice to generate a desired regulatory state from the progenitor cell. For example, if the interconnections specified in a genetic regulatory architecture of the progenitor exist, but are naturally regulated to prevent occurrence of a desired regulatory state, interdictions can be performed to spatially or temporally change the sequence of binding connections to achieve the necessary binding events for the required outcome. In this instance, an existing cis regulatory architecture is reprogrammed to achieve a different and specified regulatory state.

In contrast, if interconnections do not exist which can be utilized to achieve a desired regulatory state, interdictions can be performed that introduce the desired binding connections. Once introduced, the newly derived interactions will specify a different cis regulatory architecture. In this alternative, a cis regulatory architecture is modified or reprogrammed to yield a different architecture as well as a different and specified regulatory state.

The methods of the invention can be used for controlled induction of a particular regulatory state to implement and achieve a predetermined design corresponding to a specified regulatory state. The regulatory state can include, for example, known regulatory states of a cell, tissue or organism. Such know regulatory states include for, example, committed progenitor cells, lineage specific progenitor cells and any of the various cell types constituting known tissues or organs. Therefore, the methods of the invention can be used to generate uncommitted, committed or terminally differentiated cells corresponding to endothelial, ectoderm, mesenchymal, neuronal, muscle (smooth, skeletal or cardiac), hematopoietic, lever, heart, bone, pancreas, kidney, stomach, bladder, spleen, fibroblast, fat, epithelial, endothelial, endocrine, exocrine, stem, progenitor and germ cell types as well as all other cell types within a tissue or organism. The methods of the invention also can be used to generate specific cell types within these or other categories of cell types including, for example, β islet cell of the kidney, tyrosine hydroxylase positive cells of the substantia nigra, cells with the characteristics of pancreatic islet cells (insulin-producing) skin, hematopoietic cells, cardiac myocytes, neurons, glial cells (Jones, *HHMI Bulletin,* 10-16, March 2002, *Stem Cells: Scientific Progress and Future Directions*, Appendix C, NIH, 2001).

Using the methods of the invention, controlled induction also can be used to implement and achieve a predetermined design corresponding to an entirely new regulatory state not found in any natural cell type or organism. For example, the cis regulatory architecture can be designed to combine, delete or augment characteristics from different cell types to obtain a cell exhibiting hybrid cis regulatory characteristics. Alternatively, an entirely new regulatory state can be designed and implemented de novo to construct a regulatory state exhibiting desired characteristics not previously found in other cell types. All that is necessary to generate such non-naturally occurring regulatory states is to determine the desired regulatory state of the cell type to be produced and to design an alternative genetic regulatory architecture or cis regulatory network that will implement the induction of such functions. Interdiction at controlling points within the genetic regulatory architecture of a selected progenitor cell by the introduction of two or more exogenous network elements will cause the activation of the designed, or predetermined, series of cis regulatory network interactions to yield the non-naturally occurring regulatory state of the cell. Moreover, the interdiction can be, for example, stepwise from one adjacent regulatory state to the next or substantially continuous progression through one or more regulatory states until a final resting state is achieved. Thus, precursor cells of the desired cis regulatory state can be produced as intermediates as well as cells having the ultimate cis regulate state can be generated using the methods of the invention.

The methods of the invention can be implemented in genetic regulatory architectures derived from either procaryotic or eucaryotic cells alike. Thus, cells having non-naturally occurring regulatory states can be produced for industrial and agricultural purposes or for diagnostic and therapeutic purposes. Diagnosis and therapy can included both veterinary and human applications. For example, pancreatic cells can be produced that produce hormones other than, or in addition to insulin, for the production of specific hormones or the general production of additional hormones. Additionally, cells can be produced that circumvent ligand-receptor activation so that the cell instead produces a gene product that activates the target gene of the ligand-receptor signal. Exemplary precursor cells include, for example, primary cells of any type, HPa and PDX1. Intervention can be after, for example, a point when endogenous signals from other cells take affect and can be implemented by, for example, direct engineering of a precursor cell or by cross-regulation and feedback loops within a population of precursor cells.

Cells other than those described above or below that can be produced include, for example, yeast cells induced to overexpress endogenous genes for the production of enzymes for industrial purposes (Burlingame et al., *PharmaGenomics* (March/April), 25-29, 2003). Mammalian ovarian cells (CHO) engineered to express therapeutic human antibody drugs such as Herceptin, Rituxan, Repro and others (Ginsberg et al., The Road ahead for Biologics Manufacturing, U.S. Bancorp Piper Jaffray Equity Research, 2002; Morrow, *Genetic Engineering News* 22, 8-9, 11, 71). Non-pancreatic cell strains are engineered to produce insulin in situ for the treatment of diabetes (Bottino et al., *Gene Therapy* 10, 875-889, 2003). Mammalian brain cells modified to produce GDNF in situ for the treatment of Parkinson's disease (Choi-Lundberg et al., *Science* 275, 838-842, 1997). Wheat cells modified to overexpress, or ectopically express genes that confer improved stress tolerance, for example, to drought (Pellegrineschi et al., *JIRCAS Working Report*, 55-60, 2002).

Those skilled in the art will understand that developmental regulatory molecules are conserved from species to species and given the teachings and guidance provided herein, that cis regulatory networks can be constructed, applied or utilized to any species, across species or within species. For example, a description of conserved network elements in mouse rhombomere specification can be found in Davidson et al. *Proc. Natl. Acad. Sci. USA* 100, 1475-1480, (2003) and for human T cell lineage specification in Rothenberg and Anderson, *Developmental Biology* 246, 29-44, (2002). Therefore, cis regulatory networks of the invention are applicable for use in a variety of areas in the health and life sciences as well as in a large range of industrial, agricultural and research settings.

Cells having a specified regulatory state produced by modification of a genetic regulatory architecture can be isolated, propagated, stored and manipulated by any of various methods well known to those skilled in the art. For example, following interdiction and production of a modified genetic regulatory architecture or cis regulatory network, cells can be isolated by culture, selection, fluorescent activated cell sorting (FACS) or other methods well known to those skilled in the art. The cells can be further propagated under appropriate culture conditions for the particular cell type generated or stored, such as by cryopreservation, for future use. Further, cells produced having a specified regulatory state can additionally be manipulated by genetic or biochemical methods well known to those skilled in the art. For example, the produced cells can be additionally modified by the introduction of nucleic acids encoding desired gene products for expression and polypeptide production either in vitro or in vivo. Essentially, all methods available to the skilled person in the fields of cell, molecular or developmental biology as well as biochemistry and physical chemistry are similarly applicable to cells produced by the methods of the invention. Similarly, methods of therapy, including cell therapy and transplantation, and diagnosis also are applicable to the cells produced by the methods of the invention. Accordingly, the cells produced by the methods of the invention are substitutable in methods well known to those skilled in the art.

The invention further provides a method of diagnosing an individual suffering from a cellular defect. The method consists of: (a) measuring an activity or amount of a plurality of cis regulatory network elements in a sample from an individual suspected of having a cellular defect, and (b) comparing a genetic regulatory architecture of said plurality of cis regulatory network elements in said sample to a reference genetic regulatory architecture indicative of a cell or cellular state, wherein a change or similarity in pattern of said activity or amount of said plurality of elements compared to said reference genetic regulatory architecture indicates that said individual has a cellular defect.

In one application, cis regulatory networks or cells produced therefrom, can be used for the diagnosis of defects within a cell or individual. In this aspect, genetic regulatory architecture representing one or more cis regulatory networks can be determined from a cell suspected of having a defect and from a normal counterpart cell and compared to identify differences in genetic regulatory architecture or cis regulatory networks. Differences in cis regulatory elements, the genetic architecture or in the abundance or activity of cis regulatory elements compared to a normal cell will be indicative of a defect in the cell, tissue or organism suspected of harboring a defect.

Methods for diagnosis can be performed by, for example, constructing a genetic regulatory architecture or cis regulatory network from a sample suspected of containing the defect. It is to be understood that where an existing genetic regulatory architecture is available that it can be used directly in the methods of the invention without having to generate an architecture or network de novo. As with all other methods of the invention, the methods for diagnosis can be performed using a genetic regulatory architecture or cis regulatory network alike. For example, sufficient information can be available from knowing or determining the constituent components that are interrelated by binding activity irrespective of their organizational relationship. However, the explicit descriptions of binding organization available in a genetic regulatory architecture can be advantageous in some applications and result in greater accuracy and reliability of the result. Those skilled in the art will know, or can determine, given the teachings and guidance provided herein whether a genetic regulatory architecture or a cis regulatory network is amenable to a particular diagnostic, therapeutic or other application. Accordingly, the methods for diagnosis as well as other methods of the invention will be described below with reference to a genetic regulatory architecture although it is understood that one or more included cis regulatory network can be utilized in substitution or in addition to a genetic regulatory architecture.

A genetic regulatory architecture or representative compilation thereof can be constructed for the cellular state to be diagnosed or for an indicative cis regulatory network thereof. Diagnosis can be performed with a complete genetic regulatory architecture or with less than all components represented within a compilation. Moreover, it is sufficient to determine the attributes of a representative set of cis regulatory elements within the architecture for accurate diagnosis. The representative set of elements can be selected arbitrarily so long as a sufficient number of statistically meaningful elements are chosen that reflect the regulatory state of the regulatory architecture or network. A representative set of elements alternatively can be chosen based on prior knowledge of one or more cis regulatory network elements or cis regulatory networks being involved or associated with the suspected defect. Those skilled in the art will known, or can determine, which elements, sets of elements, cis regulatory networks or complete genetic regulatory architectures are sufficient to analyze for a particular diagnostic application given the teachings and guidance provided herein.

A sample for diagnosis of a suspected cellular defect can include, for example, purified cells, heterogenous mixtures, tissues, organs or components thereof so long as there is sufficient material to measure the presence, abundance, expression or activity of transcription factor and cis elements of an indicative cis regulatory element. For example, an unpure or heterogeneous mixture of starting material can be used where an element to be measured is unique to the cell type harboring a suspected defect because the identification of an attribute of the element will be indicative of its presence or activity regardless of other components within the mixture.

In contrast, where an element to be measured is present in one or more cell types or tissues it is beneficial to fractionate or purify the cell type harboring the suspected defect from the other components within the mixture that also contain that same element. Separation of the analyzed starting material will specificity associate the measured element's attribute with the cell type harboring the suspected defect. However, various other methods well known to those skilled in the art are available that can correlate network element abundance, activity or other attributes when measured within a purified or heterogeneous mixture of starting material. Such methods include, for example, affinity binding, affinity probes, hybridization, nucleic acid sequencing, polymerase chain reaction and the like. Detection methods can include, for example, measurements of flourescent, luminescent, radioactive, enzymatic products, dyes, mass as well as others detection moieties well known in the art. All of such methods as well as others well known in the art are applicable for use in the methods of the invention.

Diagnosis of a known or suspected cellular defect can be accomplished by, for example, measuring an attribute of a plurality of cis regulatory elements in a sample suspected of carrying the cellular defect and comparing such measurements to reference elements obtained from a cell known to lack the defect. Attributes of cis regulatory elements can include, for example, binding activity of a transcription factor or its cognate cis sequence element, binding activity of transcription factors or cis sequence elements irrespective of their cognate binding partners, amount of such elements or spatial or temporal expression patterns or activity.

Once measured, or obtained by reference to preexisting measurements, the plurality of cis regulatory elements selected for determination of a cellular defect can be assimilated into a genetic regulatory architecture describing the regulatory state of the suspect cell, tissue or organ. As described previously, diagnosis of a cellular defect can be accomplished using either a complete genetic regulatory architecture or less than a complete genetic regulatory architecture. The methods for compiling a genetic regulatory architecture have been described previously and are equally applicable for diagnosis. So long as the number of cis network elements are sufficiently representative of the network or an indicative subnetwork thereof, a genetic regulatory architecture using the measured component plurality can be generated for the suspect cell sample and be sufficient for diagnosis of the suspect cellular defect.

A plurality of cis regulatory network elements from a sample suspected of having a cellular defect can include all of the cis regulatory interactions constituting the genetic architecture of a cellular state suspected of having a defect. Alternatively, because the cis regulatory architecture inherently describes the spatial and temporal interrelationships of cis regulatory elements, a genetic regulatory architecture can be constructed from a cellular state prior to the occurrence or after the occurrence of the aberrant connection or connections leading to the defective cellular state. When a genetic regulatory architecture is constructed from a plurality of elements derived from the defective cellular state, the resultant architecture will identify both a defective cellular state as well as one or more cellular defects. Similarly, when construction is derived from a cellular state before or after the occurrence of the cellular defective the resultant genetic regulatory architecture also will identify both a defective cellular state and one or more cellular defects. However, in the later situations, the identified defective state or cellular defect will characterize, for example, either defective genetic regulatory architectures leading to, or resulting from, the manifested cellular defect. Accordingly, the point at which a plurality of cis regulatory elements is measured is unliked from the diagnostic capabilities of a genetic regulatory architecture of the invention.

Alternatively, a plurality of cis regulatory network elements from a sample suspected of having a cellular defect can include less than all of the cis regulatory interactions constituting the genetic architecture of the measured cellular state. As described previously, cis regulatory elements can be chosen arbitrarily or with bias based on prior knowledge. Additionally, the elements to be measured or assimilated into a diagnostic genetic regulatory architecture can be chosen based on a preference for a particular cis regulatory network or subnetwork. For example, a plurality of cis regulatory network elements constituting a controlling points, branch points or constituting one or more specific regulatory loops can be chosen and utilized as effectively as a complete genetic regulatory architecture or as effectively as representative elements selected throughout the network to approximate the activity of the whole network. Following measurement of the activity, amount or other indicative attribute of a plurality of cis regulatory network elements in a sample suspected of having a cellular defect, the elements can be complied into a representation or other compilation of transcription factor and cis sequence element binding connections to yield a genetic architecture of the cellular state suspected of having a cellular defect.

In one aspect, a complete or substantially complete genetic regulatory architecture is constructed from the elements obtained from the suspect sample and compared to a reference genetic regulatory architecture. Construction of a complete or substantially complete genetic regulatory architecture is as described above. Completeness of an architecture can include, for example, mapping the organizational structure of all of the binding connections of one or more cis regulatory networks within a cell or constituting a cellular state. Therefore, when a genetic regulatory architecture constitutes more than one cis regulatory network it is sufficient to compile a single cis regulatory network to when a substantially complete architecture is preferred. However, those skilled in the art can prefer to compile more than one or all cis regulatory networks to obtain a true or totally complete genetic regulatory architecture of the cell or cellular state.

In another aspect, a less than complete genetic regulatory architecture is constructed or obtained from the elements corresponding to the suspect sample and compared to a reference genetic regulatory architecture. Construction of a less than complete architecture can include, for example, mapping the organizational structure of the controlling points, branch points, one or more regulatory loops or a combination thereof. Further, additional elements can be included as desired such as transcription factors and cis sequence elements that are within or outside definitive loops or those that function as minor regulators of network. Additionally, where the diagnostic architecture is less than complete, it is sufficient, for example, to extrapolate the binding activity of the missing elements by grouping them as a unit to fill unmeasured links.

In FIG. 1, for example, where the network elements within the skeletogenic micromere regulatory territory has not been measured in a suspect sample, it is sufficient to designate the micromere inputs and outputs from a box generically denoted as a micromere. In like fashion, other unmeasured links can be specified in generic form with only the measured binding activities specified in a compilation. Thus, a less than complete genetic regulatory architecture is essentially a map of a genetic regulatory architecture in outline form. However, a less than complete architecture can include, for example, mapping the organizational structure of the included binding connections within one or more cis regulatory networks or included binding connections constituting a partial cis regulatory network within a cell or constituting a cellular state. Measurement or representation of less than all elements within a genetic regulatory architecture has as one advantage efficiency in production and simplicity in use.

Identification of a cellular defect within a suspected sample is determined by comparing a genetic regulatory architecture representing a plurality of cis regulatory elements of the suspected sample with a reference genetic regulatory architecture. The reference genetic regulatory architecture can be indicative of a normal cellular state, known or predicted to lack the cellular defect, or it can be indicative of the defective cellular state. In the former instance, a comparison of the diagnostic genetic regulatory architecture with the reference architecture, a comparison between the suspect and reference architectures will result in differences in the cis regulatory binding connections. Such differences will include and correlate with the defective cellular state. Substantial identity between the two genetic regulatory architectures indicates that the sample does not harbor the suspected defect. In the later instance, a comparison will result in identity between the suspect and reference genetic regulatory architectures where the suspect sample actually contains a defect. Differences will be observed where the diagnostic architecture lacks the suspected defect. Therefore, a reference genetic regulatory architecture can correspond to a normal or defective cellular state, or to a variety of other cellular states so long as the relationship between the reference and the diagnostic architectures is understood. Those skilled in the will know, or can routinely determine, such relationships and the appropriate comparison for the diagnosis of a cellular defect given the teachings and guidance provided herein.

Essentially, any cellular defect can be diagnosed by the methods of the invention. In this regard, it is not necessary to have prior knowledge of the functional attributes of the defective features because a comparison of the suspect and reference genetic regulatory architecture will identify differences in the cis regulatory binding connections and such differences include the defect giving rise to the aberrant cellular state. A comparison can be performed using, for example, genetic regulatory architecture representations such as those exemplified herein as well as a variety of methods well known to those skilled in the art. For example, a comparison can be performed visually, graphically or electronically by overlaying the diagnostic and reference genetic regulatory architectures. Differences in the binding interconnections will be readily apparent using such a direct approach. Alternatively, comparisons can be performed at the computational level by comparing, for example, the relative values and attributes network elements represented within the architectures. Moreover, standardization of genetic regulatory architectures can be performed to ensure that similar scales, formats or schematic designs are compared between architectures. All of such methods as well as others are well known to those skilled in the art and can be utilized in the methods of the invention.

A method of treating an individual suffering from a cellular defect is additionally provided. The method consists of: (a) identifying a point of interdiction within a cis regulatory network specifying a genetic regulatory architecture of a cell or cellular state; (b) introducing into a progenitor cell two or more network elements within said network to induce a predetermined series of cis regulatory network interactions resulting in a specified regulatory state of said progenitor cell, and (c) implanting said progenitor cell having said specified regulatory state into an individual suffering from a cellular defect under conditions sufficient for viability in an effective amount sufficient to renew a deficient cellular component.

Cis regulatory networks or cells produced therefrom also can be used in the therapeutic treatment of an individual suffering from a cellular defect. In this aspect, a genetic regulatory architecture representing one or more cis regulatory networks can be generated or obtained from a cell derived from an individual suspected of having a cellular defect. The genetic regulatory architecture can be redesigned by supplying omitted or nonfunctional binding connections or by rerouting existing or aberrant connections to cure, treat or ameliorate an underlying cause or aggravation of the defect. The underlying cause or aggravation of the defect can be previously known or suspected. Alternatively, the underlying cause or aggravation can be unknown and first diagnosed as described previously, for example, to identify differences in binding elements or connections between the sample and a reference architecture.

Methods for redesigning a genetic regulatory architecture have been described previously and are similarly applicable for therapeutically altering an architecture. In this aspect, a genetic regulatory architecture of the defective cell is reengineered with the purpose of returning the defective cell or its progeny to an architecture specifying a normal cellular state. Similarly, when an initial diagnosis is performed, a determination is be made to identify those differences in architecture between the sample and a normal cell, tissue or organ. The differences will identify one or more underlying causes or aggravations of the defective cellular condition. Reengineering the architecture to correspond to the normal cellular state is sufficient to treat the cellular defect once implemented in a progenitor cell, tissue or organ. Accordingly, reengineering a genetic regulatory architecture to a normal cellular state is achieved by correcting omitted, defective, aberrant or unwanted transcription factor binding connections to cis sequence elements within a cis regulatory network specifying a genetic regulatory architecture of the defective cell or cellular state.

Returning omitted or unwanted binding connections to a normal cellular state is implemented by introducing into a progenitor cell two or more cis regulatory network elements that correct the defect. As described previously, network elements can be chosen as points of interdiction corresponding to control points, branch points or other regulatory points within a cis regulatory network. The points of interdiction also can be., for example, upstream or downstream of a defect to correct or circumvent one or more omitted or aberrant binding connections. Further, the point of interdiction also can include direct replacement of one or more omitted or aberrant binding connections. Introduction of the two or more cis regulatory network elements can be performed, for example, by recombinant, genetic or biochemical means as described previously. Once introduced, the network elements will induce a series of cis regulatory network interactions that are predetermined by the architectural design and which direct the progenitor cell to perform normal cellular functions.

Cells modified with two or more network elements or descendants therefrom will contain the corrected cis regulatory network and corresponding genetic regulatory architecture. Such cells will be normal or otherwise lack the cellular defect and can be used to cure, treat or prevent a condition mediated by the defect. Additionally, progenitor cells containing a cis regulatory network that has been generated to supply a missing function irrespective of the its relationship to a normal cis regulatory network also can be used for the therapeutic treatment of a pathology mediated by a cellular defect. For example, a cellular defect can be corrected using a variety of genetic regulatory architectures that will circumvent a defect or substitute an alternative function for the defective binding connections. Given the teachings and guidance provided herein, those skilled in the art will known, or can determine what alternative network elements or connections will suffice that substitute for the defective elements or their functions.

Cells having modified cis regulatory networks and corresponding genetic regulatory architectures can be used in a variety of methods for the therapeutic treatment of pathology mediated by a cellular defect. For example, cells with corrected cis regulatory networks can be employed in methods well known in the art such as cell implantation, transplantation and the like.

The cells of the invention can originate from essentially any tissue or organ. For primary cells, a tissue should be selected that is easily accessible and contains cells that exhibit desirable growth and expression characteristics such as those described above. Additional considerations when selecting a tissue source include choice of a tissue that contains cells that can be isolated, cultured and modified to express a network element. Examples of sources of tissues include muscle, liver, or skin tissue, as well as venous and hematopoietic tissue in addition to those cells or tissues described previously. Other source or cell types are similarly known in the art that are capable of being modified with two or more network elements and can similarly be obtained or isolated using methods well known to those skilled in the art. Although human tissue sources are advantageous for therapeutic purposes, the species of origin of the cells can be derived from essentially any mammal, so long as the cells exhibit the characteristics that allow for expression of cis network elements.

Methods for isolating cell populations are well known in the art as described below. Alternatively, cells which have been previously characterized and isolated can be obtained from a commercial source, such as a tissue or cell bank (American Type Culture Collection, Rockville, Md.) and used directly for modification. The isolated cells should contain a sufficient or effective number of cells of the desired type which can be modified to express two or more cis regulatory network elements. Moreover, the population of cells can comprise one or more cell types so long as an effective number can be modified to express the desired network elements.

Therefore, populations of modified progenitor cells of the invention can be composed of a single cell type, all of which are modified with expressible network elements, or multiple cell types, where some or all cell types are modified. Heterogeneous populations can provide advantages in therapeutic applications where cell viability of implanted cells is augmented by the presence of accessory cells. A specific example of such heterogenous cell populations would be those derived from fetal tissue sources. Methods for the isolation of primary cells from a tissue source are well known in the art (see, for example, Freshney, *Animal Cell Culture: A Practical Approach*, 2nd ed., IRL Press at Oxford University Press, New York (1992). Maintenance of the cells prior to modification and implantation can be as a cell suspension, adherent cell culture or as organ culture. Conditions for the maintenance and culture of primary and clonal cells are well known in the art.

Once a cell type has been selected as described above, cells expressing exogenous networks are generated by introducing a vector expressing nucleic acid sequences encoding transcription factors or cis sequence elements corresponding to the designed interdiction points into an appropriate cell. Methods for introducing such vectors into a cell are well known in the art. One method of introducing a vector into a cell is by transfection of plasmid or DNA vectors. Transfection methods are well known in the art and include, for example, calcium phosphate precipitation, electroporation, liposome-mediated transfection, and microinjection as described, for example, in Sambrook et al., *Molecular Cloning: A Laboratory Manual*, Third Ed., Cold Spring Harbor Laboratory, New York (2001), and Ansubel et al., *Current Protocols in Molecular Biology*, John Wiley and Sons, Baltimore, Md. (1999). Alternatively, a retroviral or DNA vector can be transduced into a cell. Methods for transduction of retroviral and DNA vectors are also well known in the art.

Following transfection or transduction of cells with vectors of the invention, the cells are selected using a selectable marker that is either on the same vector as the exogenous element of interest or is co-transfected on a separate vector. Methods of selecting cells for expression of a selectable marker encoded by a transfected vector are well known to those skilled in the art (see, for example, Ausubel et al. supra (1998)). Following selection, an isolated population of cells expressing the cis element polypeptide or nucleic acid products of interest is obtained.

Verification that a population of cells expresses the exogenously introduced network elements can be determined using methods well known in the art. For example, a modified population of cells can be verified for the ability to express the network elements by assaying the amount of the transcription factor produced or presence of the cis sequence element in the progenitor cell genome. Transcription factor levels can be measured by, for example, immunoassay or by a functional assay for a known binding activity. Cis sequence element incorporation can be measured by, for example, hybridization or by measuring the activity of the gene regulated by the exogenous cis element. Additional methods of selecting cells expressing or containing exogenous network elements include Northern analysis and solution hybridization of mRNA obtained from the cells, in situ hybridization, immunohistology, and immunofluorescence using antibodies specific for the exogenous transcription factor or factors or for the exogenous cis sequence elements. Further selection of a population of cells suitable for use in the invention can be performed using in vitro or in vivo models. For example, the population of cells of the invention useful for treating a cellular defect can be verified for their ability to carry out the defective function in vitro or for their ability to ameliorate a phenotype or symptom of the defective condition in vivo.

Once a population of cells has been obtained, the cells can be implanted directly into a patient, processed as prosthetic grafts, frozen for long-term storage, or maintained in culture prior to implantation into an individual suffering from the defective cellular condition. It is understood that even a single cell expressing the exogenous network elements is useful in the invention. A single cell can be useful, for example, where it is a stem or progenitor cell that can be implanted and allowed to propagate and differentiate into its cis regulatory network programmed cellular state in vivo or in situ.

Modified progenitor cell populations can additionally be chosen to be implantable in an individual and remain viable in vivo without being substantially rejected by the host immune system. Those skilled in the art know what characteristics should be exhibited by cells to remain viable following implantation. Moreover, methods well known in the art are available to augment the viability of cells following implantation into a recipient individual.

One characteristic that can be exhibited by the cell or cell population to be implanted is that they are substantially immunologically compatible with the recipient individual. A cell is immunologically compatible if it is either histocompatible with recipient host antigens or if it exhibits sufficient similarity in cell surface antigens so as not to elicit an effective host anti-graft immune response. Specific examples of immunologically compatible cells include autologous cells isolated from the individual to be treated and allogeneic cells which have substantially matched major histocompatibility (MHC) or transplantation antigens with the recipient individual. Immunological compatibility can be determined by antigen typing using methods well known in the art. Using such antigen typing methods, those skilled in the art will know or can determine what level of antigen similarity is necessary for a cell or cell population to be immunologically compatible with a recipient individual. The tolerable differences between a donor cell and a recipient can vary with different tissues and can be readily determined by those skilled in the art.

In addition to selecting cells which exhibit characteristics that maintain viability following implantation into a recipient individual, methods well known in the art can be used to reduce the severity of an anti-graft immune response. Such methods can therefore be used to further increase the in vivo viability of immunologically compatible cells or to allow the in vivo viability of less than perfectly matched cells or of non-immunologically compatible cells. Therefore, for therapeutic applications, it is not necessary to select a cell type from the diabetic individual to achieve viability of the modified cell following implantation. Instead, and as described further below, alternative methods can be employed which can be used in conjunction with essentially any donor cell to confer sufficient viability of the modified cells to achieve a particular therapeutic effect.

For example, in the case of partially matched or non-matched cells, immunosuppressive agents can be used to render the host immune system tolerable to engraftment of the implanted cells. The regimen and type of immunosuppressive agent to be administered will depend on the degree of MHC similarity between the modified donor cell and the recipient. Those skilled in the art know, or can determine, what level of histocompatibility between donor and recipient antigens is applicable for use with one or more immunosuppressive agents. Following standard clinical protocols, administration and dosing of such immunosuppressive agents can be adjusted to improve efficiency of engraftment and the viability of the cells of the invention. Specific examples of immunosuppressive agents useful for reducing a host anti-graft immune response include, for example, cyclosporin, corticosteroids, and the immunosuppressive antibody known in the art as OKT3.

Another method which can be used to confer sufficient viability on partially-matched or non-matched cells is through the masking of the cells or of one or more MHC antigen(s) to protect the cells from host immune surveillance. Such methods allow the use of non-autologous cells in an individual. Methods for masking cells or MHC molecules are well known in the art and include, for example, physically protecting or concealing the cells, as well as disguising them, from host immune surveillance. Physically protecting the cells can be achieved, for example, by encapsulating the cells within a semi-permeable barrier that allows exchange of nutrients and macro molecules. The encapsulated cells can be permanently implanted or periodically replaced depending on the cell type used and the location where the device is implanted. Alternatively, antigens can be disguised by treating them with binding molecules such as antibodies that mask surface antigens and prevent recognition by the immune system.

Immunologically naive cells can also be used for constructing modified progenitor cells for use in therapeutic applications. One source of immunologically naive cells includes stem cells and lineage-specific progenitor cells. These cells are capable of further differentiation to give rise to multiple different cell types. Stem cells can be obtained from embryonic, fetal and adult tissues using methods well known to those skilled in the art. Such cells can be used directly or modified further to enhance their donor spectrum of activity.

Methods for determining immunogenicity and criteria for compatibility are well known in the art and include, for example, a mixed lymphocyte reaction, a chromium release assay or a natural killer cell assay. Immunogenicity can be assessed by culturing donor cells together with lymphocyte effector cells obtained from an individual suffering with a cellular defect and measuring the survival of the donor cell targets. The extent of survival of the donor cells is indicative of, and correlates with, the viability of the cells following implantation.

A population of cells having a modified cis regulatory network can be administered to an individual that has been determined by one skilled in the art to require treatment for amelioration of a symptom mediated by a cellular defect. The cells can be administered for amelioration of one or more phynotypes or symptoms of the cellular defect. For example, a individual suffering from a cellular defect can be implanted with the cells following diagnosis of the condition. The implanted cells will express the normal regulatory state of in response to the modified cis regulatory network so that cellular homeostasis is at least partially restored. An individual that has been effectively treated for the cellular defect will exhibit a reduction in severity of at least one of the symptoms indicative of the defect following implantation of the modified progenitor cells. The reduction in severity of a symptom can be determined and would be apparent to one skilled in the art.

The methods of the invention can also be used to improve the efficacy of other therapies for a pathological condition or other cellular defect. The methods of the invention can be used in combination with pre-existing or other methods of treatment to improve the efficacy or ease of use of the other methods. For example, modified progenitor cells can be implanted in a patient receiving regulator doses of medication for treatment of a condition. Implantation of the modified cells corrected for the deficiency can reduce the frequency or dose of medication in such a patient. An individual receiving behavioral modification therapy, for example, diet or exercise to increase the quality of life, can also be implanted with the modified progenitor cells that confer a deficient cellular function in the patient receiving behavioral modification therapy. Implantation of the modified progenitor cells in combination with such additional therapies can decrease the likelihood of disease relapse or can ameliorate signs or symptoms of the disease. The modified progenitor cells of the invention can also be used to treat a immunological or complete cellular deficiencies such as an autoimmune or degenerative disease where cells are lost by destruction. Individuals having such diseases can be additionally treated with the population of cells modified progenitor cells that replace the destroyed or defective cell population.

The modified progenitor cell populations of the invention can be administered to the individual to supply the defective function of the treated individual. Engraftment of the cells allows prolonged cellular homeostasis due to proper functioning of the modified cis regulatory network. Additionally, modified progenitor cells can be further altered to supply one or more additional gene products that are beneficial to the treatment of the individual.

A population of cells suitable for implantation consists of a size or cell number that is within a range that can be obtained, modified to transcription factor elements or cis sequence elements linked to an effector gene, and introduced into an individual. The size of the population of cells is sufficient to supply normal cellular function in substitution of the defective cellular function. Alternatively, the size of the population should be sufficient to generate by proliferation a resultant cell population that can supply the defective cellular function. The population can be, for example, differentiated or committed to a particular cell fate and be grafted into the target tissue or organ. Alternatively, the population can be undifferentiated, such as a stem cell, and become grafted upon differentiation in vivo. Such differentiation can be directed in vivo by augmentation with growth factors and signaling molecules or it can be allowed to differentiate spontaneously due to local environmental factors at the site of implantation or engraftment, for example.

The size of a population of modified progenitor cells is about $10^8$ cells, and can be between about $10^6$ to $10^3$ cells, for example, about $10^6$ or about $10^7$ cells, and can be less than about $10^6$ cells. Choice of cell number will depend on the source of the cells, the viability of the cells following implantation, and the level of cellular function to be supplied. One skilled in the art will know, using methods well known in the art, how to determine the appropriate number of cells that produce a therapeutic effect.

Implantation of cells of the invention having a modified cis regulatory network can be by a variety of routes. In addition to implantation to effect a cellular graft, a population of cells can also be administered into an individual directly, such as by direct injection intravenously, intramuscularly, subcutaneously, intraperitoneally, or into a tissue or organ site. Cells or compositions to be used for direct administration are obtained and prepared by methods well known in the art and suspended in the appropriate carrier, which can be determined by one skilled in the art. For example, the isolated population of cells can be infused either directly through a catheter connected to a device containing the cells and the catheter inserted into a vein, or can be injected directly into a tissue. The cells can be injected in a pharmaceutically acceptable carrier and also can be administered with other components such as matrix components, fragments or other molecules which facilitate adhesion of the cells. The cells can be administered in single or multiple administrations as necessary to achieve sufficient number of modified cells and functional activity to be supplied.

Alternatively, the cells can be grown on solid matrices or prosthetics, or encapsulated in semi-permeable membranes or barriers prior to insertion into an individual. The individual treated with the cells can then be monitored for efficacy of the treatment by measuring the activity levels of cellular defect. Additionally, the alleviation of at least one of the symptoms associated with the cellular defect also can be used to determine efficacy of the treatment. One skilled in the art would know the appropriate means of evaluating and diagnosing efficacy of the treatment.

The invention also can be used for the prevention of a cellular defect. For example, a population of modified progenitor cells can be implanted as a prophylactic into individuals at risk of developing a cellular defect. Genetic predisposition for a cellular defect is one example of such a risk of developing a cellular defect. These individuals can be implanted with cells having a cis regulatory network modified to perform the function of the predisposed condition.

As described previously, progenitor cells for therapeutic treatment can be modified, for example, ex vivo, in vivo or in situ. For ex vivo modification, the progenitor cells are first modified and then implanted into the individual. For in vivo or in situ, vectors containing the interdicting network elements of the invention also can be directly administered to an individual for genetic modification. The characteristics of a vector useful for ex vivo and in vivo therapy is generally similar to the characteristics of vectors useful for targeting cells to generate a population of modified progenitor cells as described above. Viral vectors are particularly advantageous for ex vivo and in vivo therapy.

The use of a viral vector is particularly advantageous for ex vivo and in vivo therapy because viruses typically infect and propagate in specific cell types. Moreover, the natural specificity of viruses for specific tissues or cell types can be used to target one or more nucleic acid molecules encoding network elements in vivo to a particular tissue or to a limited number of tissues. Furthermore, both viral and non-viral vectors can be modified with specific receptors or ligands to alter target specificity through receptor mediated events. Methods of ex vivo therapy and construction of appropriate vectors are well known in the art, for example, as described by Kay et al., *Proc. Natl. Acad. Sci. USA* 89:89-93 (1992); Chowdhury et al., *Science* 254:1802-1805 (1991); and Grossman et al., *Nature Genetics* 6:335-341 (1994); Stratford-Perricaudet et al., *J. Clin. Invest.*, 90:626-630 (1992); and Barr et al., *Gene Therapy*, 2:151-155 (1995). Methods of in vivo or in situ therapy and vector construction also are well known in the art.

Vectors for cis regulatory network modifications of the invention encoding network elements can be introduced directly into an individual. The vector to be administered to an individual can be formulated as a pharmaceutical composition comprising the network element encoding nucleic acid sequences and a pharmaceutically acceptable carrier. Pharmaceutically acceptable carriers are well known in the art and include aqueous solutions such as water, physiologically buffered saline, or other solvents or vehicles such as glycols, glycerol, oils such as olive oil or injectable organic esters.

A pharmaceutically acceptable carrier can contain physiologically acceptable compounds that act for example, to stabilize or increase the absorption of the expressible nucleic acid sequences. One skilled in the art would know that the choice of a pharmaceutically acceptable carrier, including a physiologically acceptable compound, depends, for example, on the route of administration and on the particular characteristic of the expression vector, for example, whether the vector is a viral or plasmid vector. The pharmaceutical composition also can be incorporated, if desired, into oil-in-water emulsions, microemulsions, micelles, mixed micelles, liposomes, microspheres or other polymer matrices (Gregoriadis, *Liposome Technology*, Vols. I to III, 2nd ed., CRC Press, Boca Raton, Fla. (1993); Fraley et al., *Trends Biochem Sci.*, 6:77 (1981). Liposomes, for example, which consist of phospholipids or other lipids, are nontoxic, physiologically acceptable and metabolizable carriers that are relatively simple to make and administer. (see Mannino et al., *Biotechniques* 6:682 (1988)).

A vector of the invention encoding network elements is administered in an amount and regimen that will be effective to the individual. Generally, the dosage will be about that typical for administration of nucleic acids and can be determined by one skilled in the art. An effective amount will depend on the degree of severity of the cellular defect in the individual and the level of repair desired. Such dosages and schedules of administrations are well to those skilled in the art. For example, administration of a vector harboring interdicting network elements can be as a single treatment or as multiple treatments depending on the level of transcription factor expression or of cis sequence element targeted recombination desired or on the number of cells to be modified. Methods for the delivery of nucleic acid sequences are known in the art as described, for example, by Felgner et al., U.S. Pat. No. 5,580,859, issued Dec. 3, 1996. Efficacy of the in vivo treatment is achieved if at least one of the symptoms of the cellular defect is alleviated or reduced.

A method of identifying compounds having cell fate inducing activity is further provided. The method consists of: (a) contacting a progenitor cell with a test compound under conditions sufficient for inducing a cis regulatory network interaction, and (b) measuring an activity or amount of a plurality of indicators within a cis regulatory network, wherein a specific pattern of said plurality of indicators corresponding to a specified regulatory state indicates that said test compound has cell fate inducing activity.

Compounds can be identified that alter cell fate for all types of progenitor cells described previously as well as others known in the art. The progenitor cells can be, for example, undifferentiated, committed or terminally differentiated and the compounds can be selected, for example, that induce differentiation, cell fate commitment or dedifferentiation. Progenitor cells are contacted with a test compounds under suitable assay conditions. Multiple test compounds can be measured either sequentially or simultaneously for cell fate inducing activity or a procedure employing a combination of both simultaneous and sequential addition of test compounds to a progenitor cell can be used.

A condition sufficient for inducing a cis regulatory network interaction is intended to mean a condition under which a particular method or assay, such as those described above and below, will identify, select or delineate a compound that alters a predetermined cis regulatory network property of a progenitor cell. Identification of the altered property will correlate with the presence of a test compound and indicate that the test compound has cell fate inducing activity.

Suitable conditions sufficient for inducing a cis regulatory network interaction take into account factors such as the concentration of the test compound, the duration of contact with the test compound, the temperature and buffer conditions, the method of contact, whether or not cell viability is required to be maintained, and the detection format. Generally, suitable conditions consist of culturing a progenitor cell, tissue or organ in a media that supports cell viability, proliferation, differentiation, cell fate commitment or development. Such media will contain nutrients, carbon or alternative energy source, growth factors, hormones, cytokines, metabolites and minerals to support such physiological functions. Suitable conditions can also include, for example, cell-free assays, in vitro, in situ and in vivo analysis that indicate changes in cis regulatory interactions.

Further, suitable conditions can be modified to accommodate a particular progenitor cell type, the predetermined cis regulatory network property to be detected, the desired cell fate to be achieved and the number of test compounds being screened. Suitable conditions sufficient for inducing a cis regulatory network interaction are known in the art or can be readily determined for a particular application of the method given the teachings and guidance provided herein. These conditions have been described previously and are described further below in the Examples as well as in U.S. application Ser. No. 60/384,962 are applicable for identifying a cell fate inducing compound of a progenitor cell.

A compound having cell fate inducing activity is identified following contact with a test compound for a sufficient time to allow induction of cis regulatory network interactions by measuring an activity or amount of a plurality of indicators within a cis regulatory network. The plurality of indicators can be, for example, cis network elements corresponding to substantially complete regulatory networks or corresponding to a representative sample of cis network elements. The plurality also can include gene expression, biochemical, physiological or phenotypic markers indicative of a specified cis regulatory network. Such methods have been described previously in reference to diagnostic applications of the methods of the invention and are equally applicable for the determination of a compound that induces a desired cis regulatory network interaction.

Briefly, following the addition of a test compound a plurality of cis regulatory network indicators sufficient to indicate the activity or changes in activity of cis regulatory network interactions are measured. The resultant cis regulatory network is determined or its corresponding genetic regulatory architecture is compiled to identify if there has been an alteration in a predetermined network property. The alteration can be determined by, for example, comparison to a known network or architecture, comparison to a reference network or architecture exhibiting the desired characteristic or by comparison to a wholly or partially designed network or architecture. Such reference cis regulatory networks or genetic regulatory architectures are selected or designed to specify a desired regulatory state of a cell, tissue or organ. Test compounds that induce changes in network element binding activity or amount that correspond to the specified regulatory state are identified as compounds that have cell fate inducing activity. Accordingly, when a progenitor cell is treated with the selected compound, the treated cells, tissues or organs will exhibit the specified regulatory state.

The activity or amount of a plurality of indicators can be determined, for example, by measuring binding activity of cis network elements, gene expression activity, polypeptide activity, metabolic or physiological activity or phenotypic characteristics of the contacted progenitor cell. These methods have been described previously and are described further below in the Examples as well as in U.S. application Ser. No. 60/384,962. Other methods well known to those skilled in the art are similarly applicable for measuring the alteration of cis regulatory network property of a progenitor cell.

Briefly, methods suitable for detecting various binding interactions have been described previously and are described further below in the Examples and in U.S. application Ser. No. 60/384,962. Other methods known in the art can similarly be used and include, for example, fluorescence correlation spectroscopy (FCS) and scintillation proximity assays (SPA), which are reviewed, for example, in Major, *J. Receptor and Signal Transduction Res.*, 15:595-607 (1995); and in Sterrer et al., *J. Receptor and Signal Transduction Res.*, 17:511-520 (1997). Other assays for detecting binding interactions include, for example, ELISA assays, FACS analysis, and affinity separation methods which are described, for example, in Harlow and Lane, Eds., *Antibodies: A Laboratory Manual*, Cold Spring Harbor Laboratory (1988). Such assays can often be performed with either viable or non-viable cells.

If desired, a method of the invention can be practiced using an assay wherein one or several steps, such as cell manipulation, culture plate manipulation, contacting the cells with the compounds, detection of the predetermined property, or statistical analysis of the data, are automated. Such automation advantageously provides for high throughput screening of candidate therapeutic compounds, often using smaller numbers of cells and smaller amounts of compounds and reagents than manual assays. Those skilled in the art can determine for a particular application of the method whether it would be advantageous to automate one or more steps of the screening assays. Methods of automating the assays described herein are well known in the art.

When the invention is practiced with a large number of compounds or with a large number of progenitor cells, or both, such as in a high-throughput screening format, the efficacy of test compounds in inducing a cis regulatory network interaction also can be rank ordered and analyzed using known statistical or computational methods. For example, when the invention is practiced with regard to a progenitor cells obtained from different sources or from different individuals exhibiting genetic variations or variations in cis regulatory network connections, the effect of a test compound in inducing a network interaction altering a network property can be correlated with the genetic or cis network variations using, for example, statistical methods known within the art. Therefore, the method provides a means of rapidly identifying compounds that are effective in inducing cis regulatory network interactions in progenitor cells derived from all sources or individuals. Statistical or computational methods for analyzing the data obtained using the methods of the invention are well known in the art.

The method of identifying a compound having cell fate inducing activity from a plurality of test compounds will depend on the number of compounds being tested and the particular assay employed. For example, the method of the invention can be repeated by subdividing pools of test compounds into smaller pools, until a single compound that reproducibly induces a cis regulatory network interaction of a progenitor cell is identified. Alternatively, a test compound that induces a cis regulatory network interaction of a progenitor cell can be isolated away from the cell it affects and its identity determined. Additionally, a test compound that induces a cis regulatory network interaction of a progenitor cell can be identified by virtue of an inherent characteristic structural or functional property, or by virtue of a distinguishing label. These and other methods of identifying a cell fate inducing compound resulting from practice of the method of the invention are known in the art.

Additionally, the efficacy of the test compound can be further validated by repeating the method using assays that detect alterations in one or more different cis regulatory network connections or properties associated with the induced regulatory state. Moreover, the method can be repeated using varying concentrations of a test compound to determine the minimally effective and least toxic concentration. Therefore, the method can be used to identify those test compounds that are most likely to be safe, effective and practical as therapeutics or research reagents to induce a desired cell fate having a specified regulatory state.

A test compound identified by a method of the invention that induces a cis regulatory network interaction altering a predetermined cis regulatory network property of a progenitor cell is effective in diagnostic, therapeutic, industrial, veterinary and agricultural applications to the same extent as is a modified progenitor cell or a reference cell when used in a method of the invention. For example, the identified compound inducing a desired cis regulatory network interaction can be directly administered to an individual to induce in vivo differentiation, development or cell fate commitment in substitution modified cell implantation. Such direct administering of an identified compound can be in lieu of implantation, in conjunction with implantation or it can be used to compliment the functions supplied by the modified progenitor cells. For diagnostic applications as well as for other applications, such as the identification and construction of an initial cis regulatory network, identified compounds can be used to induce a predetermined cis regulatory network property of a progenitor cell and used as a reference cell indicative of the reference cellular state.

Given the teachings and guidance provided herein, it is understood that any and all applications described previously for modifying a progenitor cell can instead be implemented in a non-permanent fashion through treatment of a progenitor cell with an compound identified to induce the desired cis regulatory network interactions. The use of identified compounds offer the advantage of forgoing genetic modification of the progenitor cell by introduction of exogenous cis network elements.

It is understood that modifications which do not substantially affect the activity of the various embodiments of this invention are also included within the definition of the invention provided herein. Accordingly, the following examples are intended to illustrate but not limit the present invention.

EXAMPLE I

Construction of a Cis-Regulatory Network

This Example shows the construction and characterization of cis-regulatory networks that describe the genetic regulatory architecture of a cell and of various cellular states.

Development of the body plan is controlled by large networks of regulatory genes. A gene regulatory network that controls the specification of endoderm and mesoderm in the sea urchin embryo is described. The network was derived from large-scale perturbation analyses, in combination with computational methodologies, genomic data, cis-regulatory analysis, and molecular embryology. The network contains over 40 genes and each node can be directly verified at the DNA sequence level by cis-regulatory analysis. Its architecture reveals specific and general aspects of development, such as how given cells generate their ordained fates in the embryo and why the process moves inexorably forward in developmental time.

The genetic programming mechanism for organism development and cellular differentiation is hardwired in the genomic DNA because the species specificity of the body plan is a cardinal heritable property. But despite all the examples of how individual genes affect the developmental process, there is yet no case where the lines of causality can be mapped from the genomic sequence to a major process of bilaterian development. One reason for this is that most of the developmental systems that have been intensively studied produce adult body parts, such as the third instar *Drosophila* wing disc, or the vertebrate hindbrain during rhombomere specification, or the heart anlagen of flies and mice (Davidson, *Academic Press*, San Diego, Calif. (2001)). These systems present challenges because they go through successive stages of pattern formation in order to generate complex morphologies and their development is initiated from states that are already complex. Furthermore, traditional molecular, genetic, and developmental biological approaches have focused on determining the functions of one or a few genes at a time, an approach that is insufficient for analysis of large regulatory control systems organized as networks.

The heart of such networks consists of genes encoding transcription factors and the cis-regulatory elements that control the expression of those genes. Each of these cis-regulatory elements receives multiple inputs from other genes in the network; these inputs are the transcription factors for which the element contains the specific target site sequences. The functional linkages of which the network is composed are those between the outputs of regulatory genes and the sets of genomic target sites to which their products bind. Therefore, these linkages can be tested and verified by cis-regulatory analysis. This means identifying the control elements and their key target sites, and determining their functional significance. The view taken here is that "understanding" why a given developmental process occurs as it does requires learning the key inputs and outputs throughout the genomic regulatory system that controls the process as it unfolds.

In mechanistic terms, development proceeds as a progression of states of spatially defined regulatory gene expression. Through this progresssion specification occurs which is the process by which cells in each region of the developing animal come to express a given set of genes. The spatial cues that trigger specification in development are generally signaling ligands produced by other cells, in consequence of their own prior states of specification. In addition to intercellular signals, maternal molecules of regulatory significance are distributed to particular cells with the egg cytoplasm and partitioned spatially during cleavage. Ultimately, either inter- or intracellular spatial cues affect the course of events in development by causing the activation (or repression) of particular genes encoding transcription factors. But although it is these genes that do the transcriptional regulatory work of spatial specification, the locus of programmatic control for each developmental event is the sequence of the particular cis-regulatory elements that respond to the inputs presented.

Genes encoding transcription factors are typically used at many times and places in the life cycle, and so the uniqueness of any given developmental regulatory network lies in its operative cis-regulatory modules. Such cis-regulatory systems produce new and often more refined spatial patterns than those described by their inputs in that they add regulatory or informational value. For example, cis-regulatory elements active in spatial specification often use "and" logic, in that two different transcription factors, each present in a given spatial domain, must be bound to the cis-regulatory DNA at once in order for transcription to be activated (Davidson, supra, 2001). The gene is expressed only where the input patterns overlap, and this defines a new spatial regulatory state. By determining the succession of DNA sequence-based cis-regulatory transactions that govern spatial gene expression, closure can be brought to the question of why any particular piece of development actually happens.

One closely examined example of a cis-regulatory information processing system is that which controls developmental expression of the endo16 gene of the sea urchin embryo. Endo16 encodes a large polyfunctional protein that is secreted into the lumen of the embryonic and larval midgut. Endo16 is expressed in the early embryo in the progenitors of the endomesoderm, then throughout the gut, and finally only in the midgut (McGrath et al., *Dev. Biol.* 136:264 (1989); Ransick et al., *Mech. Dev.* 42:117 (1993) and Soltysik-Espanola et al., *Dev. Biol.* 165:73 (1994)), a not very elaborate spatial sequence. But its control system turns out to be an elegantly organized and complex information processing device that responds to both positive and negative inputs to set the boundaries of expression.

Early and late expression phases are controlled by two different subregions of the regulatory sequence, or modules, each several hundred base pairs long. Together these are serviced by nine different DNA sequence -specific transcription factors. The functional role(s) of each interaction were determined (Yuh et al., *Science* 279:1896 (1998) and Yuh et al., *Development* 128:617-629 (2001)), and a computational model was derived to describe how this system responds to its time-varying regulatory inputs and to mutations and combinations of its target sites. The functions that the endo16 regulatory system performs are conditional on the inputs, and they include linear amplification of these inputs, but also many nonlinear operations such as an intermodule switch that transfers control from the early to the late module, detection of input thresholds, and various logic operations (Yuh, supra, 1998, and Yuh, supra, 2001). The model affords precise predictions of the responses of this cis-regulatory system under all conditions.

Uses of a First-Stage Regulatory Network Model

A cis-regulatory network model portrays both the overall intergenic architecture of the network and the information processing functions of each node. The model can then handle the kinetic flow of regulatory inputs around the whole system. Because of the nonlinear processing functions at each node, inputs into the network are unlikely to be propagated through it in a linear fashion. But the primary goal is to discover the logic map of the intergenic regulatory interactions, and to represent this map as a first-stage regulatory network model. Its function is just to define precisely those inputs and outputs to each cis-regulatory element that derive from other genes in the network. Such a model was derived for endomesoderm specification in the sea urchin embryo. Although in absolute terms there is a large number of genes in the endomesoderm network (almost 50 at present), they are only a tiny fraction of the total being expressed in the embryo, which is estimated at about 8500 (Davidson, supra, 2001).

There are two ways to consider such network models, which are roughly equivalent to the functional genomics point of view and the developmental biology point of view (see, for example, U.S. Ser. No. 60/384,962 and subsequent publication Bolouri and Davidson *Dev. Biol.* 246:2-13 (2002) and also Arnone and Davidson, *Development* 124:1851

(1997)). In the "view from the genome," all relevant inputs into each cis-regulatory element that occur in all cells at all times in the developmental process are shown at once. This view gives the genetically determined architecture of the network and predicts the target site sequences that is functional in the genomic cis-regulatory DNA. The second, the "view from the nucleus," highlights only those interactions occurring in given nuclei in the particular time frame of that view. It explains why given genes are or are not being expressed at given times and in given cells.

Endomesoderm Specification in the Sea Urchin Embryo

The biology of the sea urchin embryo offers natural advantages for a regulatory network analysis of development. Not many regulatory steps separate the initial zygotic gene expressions that first distinguish a given patch of embryonic cells from the activation of terminal differentiation genes in the progeny of these cells (Davidson, supra, 2001; Davidson, *Development* 113:1 (1991) and Davidson et al., *Development* 125:3269 (1998)). Furthermore, the sea urchin embryo gives rise only to a very simply constructed larva that consists of single-cell-thick structures and only 10 to 12 cell types (Davidson and Cameron, supra, 1998), rather than to a morphologically complex juvenile version of the adult body plan, as in the development of insects and vertebrates.

Not only is the molecular and developmental biology of the sea urchin embryo well known (Davidson, supra, 2001; Davidson and Cameron, supra, 1998; Angerer and Angerer *Dev. Biol.* 218:1 (2000) and Horstadius, *Biol. Re. Camb. Phiols. Soc.* 14:132 (1939)), but dozens of developmentally regulated genes have been cloned, the overall embryonic expression patterns are well described, and the genome has been at least somewhat characterized (Cameron et al., *Proc. Natl. Acad. Sci. USA* 97:9514-9518 (2000); Zhu et al., *Development* 128:2615 (2001) and Poustka et al., *Genomics* 59:122 (1999)). A large collection of arrayed cDNA and bacterial artificial chromosome (BAC) libraries is available (Cameron et al., supra, 2000). Furthermore, the sea urchin embryo provides a high-throughput test bed for cis-regulatory analysis by gene transfer (Yuh et al., supra, 2001; Kirchhamer and Davidson, *Development* 122:333 (1996); McMahon et al., *Dev. Biol.* 108:420 (1985) and Flytzanis et al., *Proc. Natl. Acad. Sci. USA* 84:151 (1987)).

The endomesoderm of the sea urchin embryo forms from cell lineages at the south pole (the "vegetal" pole) of the early embryo. The endomesodermal constituents of the embryo ultimately consist of the skeletogenic mesenchyme, which arises from the micromere lineage; several other mesodermal cell types; and the gut endoderm. Most of the gut endoderm and all but the skeletogenic mesodermal cell types derive from the progeny of a ring of eight sixth cleavage cells, called "$veg_2$"; the remainder of the gut endoderm derives from their eight sister cells, "$veg_1$", which also give rise to some ectoderm. What happens in the specification of the lineages is well understood (see, for example, U.S. Ser. No. 60/384,962 and subsequent publication Davidson et al. *Dev. Biol.* 246:162-190 (2002) and also Davidson and Cameron, supra, 1998). A compressed summary of major steps is shown in Table 1.

TABLE 1

Phenomenological aspects of endomesoderm specification in sea urchin embryos: developmental process 1. Autonomous cues of material origin
   Nuclearization of β-catenin (Logan et al., supra, 1999) in micromeres (by fourth cleavage) and $veg_2$ cells TABLE 1-continued Phenomenological aspects of endomesoderm specification in sea urchin embryos: developmental process (from sixth cleavage on)
   Exclusion of ectodermal transcription factors from vegetal-most cell nuclei (Angerer and Angerer, supra, 2000)
   Nuclearization of Otx factor in micromeres at fourth cleavage (Chuang et al., Dev. Genet., 19: 231 (1996))
2. Early micromere signal
   Micromere signal to $veg_2$ (fourth through sixth cleavage) required for normal endomesodermal specification (Ransick and Davidson, supra, 1993, and Ransick and Davidson, supra, (1995)
3. Wnt8/Tcf loop
   Wnt8 ligand expressed throughout endomesodermal domain maintains and stregthens β-catenin/Tcf input in these nuclei (Davidson et al., supra, 2002)
   β-catenin/Tcf input required for endomesoderm specification (Logan et al., supra, 1999); reviewed in (Davidson, supra, 2001; Davidson, supra, 1998 and Davidson et al., supra, (2002)
4. Late micromere signal
   Expression of Delta ligand in micromeres (Sweet et al., supra, in press; United States Ser. No. 60/384,962 and subsequent publication Oliveri et al., Dev. Biol., 246: 209-228 (2002))
   Activation of Notch signal transduction in $veg_2$ descendants adjacent to micromeres that receive Delta signal (Sherwood and McClay, supra, 1997; Sherwood and McClay, supra, 1999; Sherwood and McClay, supra, 2001 and Sweet et al., Development 126: 5255 (1999))
5. Skeletogenesis
   Skeletogenic functions expressed after ingression of skeletogenic cells in late blastula
6. Specification of $veg_2$ mesoderm and endoderm
   Segregation of cell type precursors within vegetal plate complete by late blastula (Ruffins and Ettensohn, Dev. Biol., 160: 285 (1993) and Ruffins and Ettensohn, Development 122: 253 (1996))
   Mesoderm cells turn off endoderm genes, leaving endoderm genes expressed in peripheral $veg_2$ cells (Davidson et al., supra, 2001 and Ruffins and Ettensohn, supra, 1993)
7. Specification of $veg_1$ endoderm
   Wnt8 signal from $veg_2$ to $veg_1$ and activation of β-catenin nuclearization in abutting $veg_1$ cells (Davidson et al., supra, 2001 and Logan et al., supra, 1999)
8. Invagination of archenteron
   $Veg_2$ mesoderm carried inward at tip of archenteron on gastrulation
   Followed by roll-in of $veg_1$ endoderm, contributing mainly hindgut (Ransick and Davidson, Dev. Biol. 195: 38 (1998) and Logan and McClay, Development 124: 2213 (1997))

Briefly, this description relates to indirectly developing euechinoid species, such as *S. Purpuratus, L. variegatus, Hemicentrotus pulcherrimus*, and *Paracentrotus lividus*.

The specification of the micromere lineages occurs as soon as these cells are formed at fourth cleavage, because if isolated then and cultured, their progeny will express skeletogenic functions just as they do in their natural situation (Davidson and Cameron, supra, 1998). Their specification depends initially on localized maternal cues.

Specification of the $veg_2$ lineage in endomesodermal progenitor cells begins immediately as well. There are two inputs required: one a signal passed from the micromeres to the immediate ancestors of the $veg_2$ ring, at fourth to sixth cleavage (Ransick and Davidson, *Science* 259:1134 (1993) and Ransick and Davidson, *Development* 121:321-322 (1995)), and the other the nuclearization of β-catenin, which consists in its accumulation in the nuclei of all prospective endomesodermal cells (Logan et al., *Development* 126:345 (1999)). β-catenin is a cofactor of the Tcf transcription factor, and its initial nuclearization is autonomous rather than signal dependent. However, the endomesodermal cells soon activate a gene encoding the signaling ligand Wnt8 which, when bound by the adjacent cells, stimulates a signal transduction pathway that results in further nuclearization of β-catenin/Tcf. Endomesodermal functions downstream of the Tcf transcription input are thereby reinforced by an intra-endomesodermal signaling loop (Davidson et al., supra, 2002).

At seventh through ninth cleavage, the descendants of the micromeres, now located in the center of the disc of $veg_2$ cells, emit the ligand Delta (Sweet et al., *Development*, in press and Oliveri et al., supra, 2002), which activates the Notch (N) signal transduction system in the adjacent $veg_2$ cells and is required to specify them as mesoderm (Sherwood and McClay, supra, 1997; Sherwood and McClay, *Development* 126:1703 (1999) and Sherwood and McClay, *Development* 128:2221 (2001)). If the specification map is imagined from the bottom, the pattern of cell fates and by now of gene expression would display a concentric arrangement (Davidson and Cameron, supra, 1998). In the center are the "small micromeres," which are the fifth-cleavage sister lineage of the skeletogenic micromeres and which are surrounded by the skeletogenic precursors and by the $veg_2$ mesoderm precursors and finally by the $veg_2$ endoderm precursors. The embryo is still an indifferent-looking hollow ball of cells, but the specification map is well on its way to completion. At 20 to 24 hours, the skeletogenic cells move inside the blastocoel leaving behind a now fully specified central disc of prospective mesodermal cell types, and peripheral to them, the endoderm precursors. After this, a late Wnt8 signal from the $veg_2$ endoderm causes the adjacent $veg_1$ progeny to become specified as endoderm as well, and gastrular invagination ensues. The methods described herein are able to discover the network of regulatory interactions underlying the events of endomesoderm specification during the first 24 hours, by which point some mesodermal and endodermal differentiation genes are already being expressed in a cell type-specific manner.

Analyzing a Cis-Regulatory Network

The cis-regulatory network for endomesoderm specification was derived, in part, from a large-scale perturbation analysis in which the expression of many different regulatory genes and the operation of several signaling processes were altered artificially. The effects on many other genes were then measured with quantitative real-time fluorescence polymerase chain reaction (QPCR).

Briefly, for perturbation measurements by QPCR, RNA was extracted from embryos grown from eggs injected with the respective perturbation reagents and converted to cDNA. This was used in multiplexed QPCR experiments to assess the quantitative effects of each perturbation on the other genes indicated in FIG. 1, usually at several different stages. The effects for data included in the model ranged from threefold increases or decreases in the amount of transcript as a result of the perturbation up to several hundred fold increases or decreases. Results were obtained on at least two different independent batches of cDNA for each perturbation, sometimes more, and often several repeats were performed on each batch. Numerical data are available at the URL in Sherwood and McClay (supra, 1997).

In one set of perturbations, the effect of a morpholino antisense oligonucleotide (MASO), described in Oliveri et al., supra, (2002), to prevent translation of mRNA was studied. Briefly, eggs giving rise to control embryos were injected with an mRNA encoding a fusion between the 5' leader plus the initial part of the coding sequence of a gene encoding the Pmar1 transcription factor (Oliveri at al., supra, 2002), fused to the GFP coding sequence, plus an irrelevant morpholino oligonucleotide. Eggs giving rise to the perturbed embryos were injected with the same GFP fusion plus a MASO targeted to the leader sequence of the pmar1 mRNA. The control embryos displayed normal morphology at 24 hours and all the cells in the embryos expressed GFP as shown by fluorescence. In the perturbed embryos, while the abnormality of the resulting morphological phenotype was not yet evident at 24 hours, the expression of GFP was totally abolished. The observations for the perturbed embryos were made with a gain about 100 times that used for the control embryos, to allow for the outline of the embryos to be seen.

In a second set of perturbations, the effects of the introduction of a form of Krox1 that acts as an obligate repressor of its target genes were studied. The morphology of the control embryos was studied at 72 hours, as well as that of the embryos of the same age expressing an injected mRNA that encodes a fusion between the DNA binding domain of the Krox1 transcription facto (Want et al., *Mech. Dev.* 60:185 (1996)) and the *Drosophila* Engrailed repressor domain). It was observed that gut formation had not occurred, while other severe abnormalities affecting the ectoderm and skeleton formation had occurred. Finally, an excess of pigment cells as well as other mesodermal cell types was observed.

In a third set of perturbations, the effect of blocking β-catenin nuclearization via blocking of activation of Wnt/Tcf signaling pathway was studied by injection of cadherin mRNA. The morphology of the control embryos was studied at 48 hours, as well as that of the embryos of the same age expressing an injected mRNA that encodes the intracellular domain of cadherin. It was shown that the cadherin embryos consisted of a hollow ball of ectoderm, indicating that endomesodermal specification was completely wiped out.

In a fourth set of perturbations, the effect of blocking Notch signaling pathway was studied by the introduction of a negatively acting derivative of the N receptor. A control 37-hour late gastrula was analyzed as well as an embryo of the same age expressing an injected mRNA encoding the extracellular domain of the N receptor. This embryo showed a normal complement of skeletogenic mesenchyme cells and a well-formed gut but only a very few mesodermal cells of $veg_2$ origin as compared with the control. QPCR data cited here are available at URL its.caltech.edu/~mirsky/qpcr.htm.)

For an input to be considered significant, the effect of the perturbation had to be greater than threefold with respect to the control. For example, the level of the target gene transcript must be, <30% or >300% of normal as a result of the perturbation. Numerical QPCR data are available online at URL's its.caltech.edu/~mirsky/endomes.htm and its.caltech.edu/~mirsky/qpcr.htm.

Many of the network linkages described in this study were based on perturbations that remove functions such as morpholino-substituted antisense oligonucleotides, or blockade of all endomesoderm specification, or blockade of mesoderm specification (Davidson et al., supra, 2002). One mRNA encoding a transcription factor and mRNAs encoding four different Engrailed domain fusions to transcription factors were used as well (Li et al., *Dev. Biol.* 212:425 (1999). The introduction of mRNA encoding sequence-specific transcription factors at levels grossly beyond those naturally present per cell can lead to non-specific results, by engendering interactions with weak target sites.

The mRNA encoding a natural transcription factor used in this work was pmar1 mRNA, which produces a repressor. The level injected into the egg was only two to three times the normal level per cell (discounting mRNA decay), although after injection it was globally distributed. The identical phenotypes (shown in FIG. 2) were obtained after injection of mRNA encoding a Pmar1-Engrailed domain fusion. This result is consistent with both studies (Oliveri et al., supra, 2002).

Three other mRNAs encoding Engrailed fusions were used. The specificity of the first, Otx-Engrailed has been described by Li et al., supra, 1999. The specificity of the effects of the second, encoding Krox-Engrailed, is attested to by the minor fraction of tested genes on which it had an effect (Davison et al., supra, 2001) and the fact that the only genes that were affected are required where krox is expressed, even though the exogenous mRNA is present globally. The last, encoding an Elk-Engrailed construct, affects only three other genes out of all those tested (Davidson et al., supra, 2001) (FIG. 1). Elk plays a peripheral role in the network up to 24 hours, and its main importance involves later events in development. These mRNAs were all introduced into the egg in amounts that would produce levels within an order of magnitude of the natural mRNA concentrations per cell, sometimes within a few fold of these concentrations or less because of continuing decay of the exogenous mRNA.

Perturbation analysis can be combined or substituted with other approaches to distinguish between direct and indirect effects. For example, blockade of the expression of a gene that encodes a transcriptional activator can decrease expression of both immediately and secondarily downstream target genes; and if it encodes a repressor, blockade of its expression can increase expression of both. Direct effects are those in which a perturbation in the expression or function of a transcription factor causes changes in the expression of another gene because target sites for that factor are included in a cis-regulatory element of the gene. Cis-regulatory analysis can therefore be used to resolve whether effects on a given control element are indeed direct.

Another approach used at several nodes of the network is the attempted rescue of a perturbation effect by introduction of appropriate amounts of mRNA encoding a different factor, which might be mediating an indirect effect of the perturbation. In such rescue studies, if the effect is indirect via a second gene, then the introduction of mRNA generated from the second gene will suffice to correct the perturbation effect. If the effect is direct, little rescue can be obtained by this route. For example, if gene A activates gene B, which in turn activates gene C, then the effect of a knockout of gene A expression is direct for gene B but indirect for gene C, and the effect of the gene A knockout on gene C would be rescued by the introduction of B mRNA. If, on the other hand, there are necessary target sites for the gene A product in the cis-regulatory elements of both genes B and C, then the effect on gene C of a gene A knockout is unlikely to be rescued by the introduction of B mRNA. Where a rescue experiment indicates an indirect effect, or where the effect must be indirect because the affected and the perturbed genes are expressed in different cells or at different times, the implied relationships were omitted from the network models. This choice was because only direct effects imply specific genomic target site sequences in the cis-regulatory systems of the affected genes, and an object of the network model is to make explicit a map of cis-regulatory interrelations.

In an iterative process, the indications from the perturbation results were checked against the network model, further studies were designed, and the model was altered according to their results. The model was constructed with the program Netbuilder (see, for example, U.S. Ser. No. 60/384,962 and subsequent publication Brown et al., *Dev. Biol.*, 246:86-102 (2002)), a software tool for the construction of computational models that allows simulations to be performed, so as to test whether its relationships generate the appropriate outputs.

However, the initial model had to conform to the facts as they are known in the field of embryology (Table 1).

Gene discovery was also used in order to clothe with real genes the armature of interactions derived from the embryology, and to add to the collection of genes already known to be involved in endomesoderm specification. Several screens were carried out and are summarized in (Table 2).

TABLE 2

Differential gene discovery screens.

| Driver from | Selectate from | Ref. |
|---|---|---|
| 1. Embryos expressing intracellular Cad | LiCl-treated embryos | Ranskick and Rast, supra, 2002. |
| 2. Embryos expressing extracellular N | LiCl-treated embryos | Davidson et al., supra, 2001 and Calestani and Davidson, supra, unpublished data. |
| 3. Control embryos too young to express bra | Embryonic cells ectopically expressing bra|| | Rast et al., supra, in preparation. |
| 4. Embryos bearing α-bra MASO | Embryonic cells ectopically expressing bra | Rast et al., supra, in preparation. |

Briefly, macroarray filter screens were carried out with probes prepared by high-$C_0T$ subtractive hybridization, using single-stranded driver and selectate, as described (Rast et al., *Dev. Biol.* 228:270 (2000)). "Selectate" denotes the cDNA preparation that contains the sequences of interest, in contrast to the nucleic acid present in excess in the hybridization reaction: The "Driver," which lacks these sequences. In the subtractive hybridizations, the reactions were carried out to near termination with respect to driver, and nonhybridized selectate sequences were recovered by hydroxyapatite chromatography (Rast et al., supra, 2000).

Briefly, Cad, an intracellular domain of cadherin, is known to sequester β-catenin, which is thereby localized at the inner surface of the cell membrane. An excess of the cadherin intracellular domain severely decreases the availability of β-catenin for transit into the nucleus. LiCl-treated embryos produce excess endomesoderm (Horstadius, supra, 1939 and Cameron and Davidson, supra, 1997).

Furthermore, it is known that the extracellular domain of N acts as a repressor of N function in mesoderm specification (Sherwood and McClay, supra, 1999) and that the brachyury (bra) gene is active by about 18 hours and thus driver mRNA was extracted from normal 15-hour embryos. Finally, ectopic bra-expressing cells were obtained by disaggregating 18-hour embryos expressing genetic constructs that produce bra mRNA under the control of a ubiquitously active cis-regulatory element. The transgenic cells were tagged with green fluorescent protein (GFP) and isolated by fluorescence-activated cell sorting (FACS) (see, for example, U.S. Ser. No. 60/384,962 and in subsequent publication Rast et al., *Dev. Biol.*, 246:191-208 (2002)). MASO embryos were collected at 24 to 27 hours (late blastula stage), and cells expressing bra were obtained by FACS as above, but at 24 to 27 hours (Rast et al., supra, (2002)).

In these screens endomesoderm specification was perturbed so as to generate material for use with a very sensitive subtractive hybridization technology applicable for use with large-scale arrays of $\sim 10^5$ clone cDNA libraries (macroarrays) (Rast et al., supra, 2000). The purpose was to create probes in which sequences differentially expressed in the endomesoderm are greatly enriched by 20- to 30-fold. This approach affords the possibility of isolating very rare transcripts.

The probes were used for high Cot (concentration×time) hybridization to the macroarrays, and the results were digitized and analyzed with a new image analysis program, BioArray, which was designed for analysis of differential macroarray screens (Brown et al., supra, 2002). New regulatory genes were recovered, as well as genes encoding differentiation proteins of the endoderm and mesoderm (see, for example, U.S. Ser. No. 60/384,962 and in subsequent publication Davidson et al., supra, 2002; Ransick et al., *Dev. Biol.* 246:132-147 (2002); Rast et al., supra, (2002)). Supplementary material, including the expression of the pks gene, is available at URL sciencemag.org/cgi/content/full/295/5560/1669/DC1. All QPCR measurements cited are available at URL's its.caltech.edu/~mirsky/qpcr.htm.

The phenotype of the negatively acting N embryos has previously been described. Most of the transcriptional regulatory genes that are specifically involved in endomesoderm specification up to 24 hours are known (Ransick et al., supra, 2002). On the other hand, only a small sample of endomesodermal differentiation genes have so far been recovered because most of the screens were directed at the earlier stages of the specification process as summarized in Table 2.

Direct cis-regulatory analysis is useful to test the predicted network linkages. However, the task of finding these elements on the scale of the network was modified from the traditional methods, which involve searching over all the genomic DNA surrounding a gene of interest. For example, the average intergenic distance in *Strongylocentrotus purpuratus* is about 30 kb (Cameron et al., supra, 2000). The modification involved computational interspecific sequence analysis.

Briefly, BAC recombinants containing the genes of interest in a more or less central position were recovered from two sea urchin species. These were *S. purpuratus*, on which all the studies were carried out, and *Lytechinus variegatus*, which develops in a very similar manner. The last common ancestor of these species lived about 50 million years ago (Gonzales and Lessios, *Mol. Biol. Evol.* 16:938 (1999) and Paul and Smith, *Biol. Rev.* 59:443 (1984)). The sequences of BACs representing most of the genes in the network at present were obtained and annotated (Davidson et al., supra, 2002). A software program, termed FamilyRelations, was built for the purpose of recognizing short patches of conserved sequence in long stretches of genomic DNA (Brown et al., supra, 2002). Applied to the *Strongylocentrotus-Lytechinus* species pair, this approach efficiently served to identify cis-regulatory elements that score positively in gene transfer tests (see, for example, U.S. Ser. No. 60/384,962 and in subsequent publication Yuh et al., *Dev. Biol.* 246:148-161 (2002)).

In summary, three software packages were developed and used for construction of a cis regulatory network: Netbuilder, FamilyRelations, and BioArray (Brown et al., supra, 2002). These programs are all available at the URL sea-urchin.caltech.edu/software.

Provisional Endomesoderm Cis-Regulatory Network

The overall network combines all significant perturbation (Davidson et al., supra, 2002 and Gene Network at its.caltech.edu/~mirsky/endomes.htm) and time and place of gene expression data, as determined by whole mount in situ hybridization (WMISH) and QPCR measurements (Davidson et al., supra, 2002). Furthermore, it comprehends computational and experimental cis-regulatory and rescue experiments data and all the underlying information from experimental embryology. The view from the genome of the regulatory gene network for endomesoderm specification is shown in FIG. 1. The network in this figure and the perturbation data on which it is based are available online at the URL's its.caltech.edu/~mirsky/qpcr.htm. Additional details and discussion are provided in Davidson et al., supra, (2002).

The top of FIG. 1, above the triple line, shows the earliest interactions. In the middle tier of the figure are shown the color-coded spatial domains, and the genes, which are placed according to their final loci of expression. The lavender areas at the left indicated by the black background label Mic represents the skeletogenic micromere domain before ingression. The light green area indicates the $veg_2$ endomesoderm domain with genes eventually expressed in endoderm on yellow backgrounds and genes eventually expressed in mesoderm on blue backgrounds. The tan box at right represents the $veg_1$ endoderm domain.

Many genes are initially expressed over broader ranges, and their expression later resolves to the definitive domains. The rectangles in the lower tier of the diagram show downstream differentiation genes (PMC, "primary" or skeletogenic mesenchyme). Short horizontal lines from which bent arrows extend represent cis-regulatory elements responsible for expression of the genes named beneath the line. Embryonic gene expression was perturbed in specific ways as described previously. The arrows and barred lines indicate the inferred normal function of the input (activation or repression), as deduced from changes in transcript levels due to the perturbations. Each input arrow constitutes a prediction of specific transcription factor target site sequence(s) in the cis-regulatory control element. In some cases, the predicted target sites have been identified in empirically defined cis-regulatory elements that generate the correct spatial pattern of expression (solid triangles). At the upper left, the light blue arrow represents the maternal β-catenin (cβ) nuclearization system (X). This transcriptional system (nβ-TCF) is soon accelerated and then taken over by zygotic Wnt8 (dark blue lines); its initial activation, of mixed zygotic and maternal origins, is shown in light blue. Data for the roles of SoxB1 and Kruppel-like (Krl) are from Howard et al., (supra, 2001) and Kenny et al., (supra, 1999). Data for the role of Ets are from Akasaki, and Kurokawa et al., *Mech. Dev.* 80:41 (1999)).

"Micr/Nuc Mat Otx" refers to the early localization of maternal Otx in micromere nuclei at fourth cleavage (Chuang et al., supra, 1996). Genes labeled "Repressor" are deduced; all other genes shown were studied at the DNA sequence level and by multiplexed QPCR. "Ub" indicates a ubiquitously active positive input deduced on the basis of ubiquitous expression seen by whole-mount in situ hybridization, under conditions in which a spatial repression system that normally confines expression has been disarmed. Dotted lines in the diagram indicate deduced but indirect relationships. Arrows inserted in arrow tails indicate intercellular signaling interactions. Small open or closed circles indicate perturbation effects that resist rescue by the introduction of mRNA where there is a possibility that the effect seen is actually an indirect result of an upstream interaction; that is, this possibility of such an indirect effect has been empirically excluded, and both sites are shown as probable direct inputs (Davidson et al., supra, 2001). Large open ovals represent cytoplasmic biochemical interactions at the protein level, such as those responsible for nuclearization of β-catenin, for the effect of Delta on N (Jacobsen et al., supra, 1998); or for the effect of Neuralized, an E3 ubiquitin ligase with specificity for Delta (Yeh et al., *EMBO J.* 19:4827 (2000) and Yeh et al., *Curr. Biol.* 11:1675 (2001)).

The outputs from each gene in the diagram are color-coded: for instance, that from the gatae gene (GenBank accession number, AF077675), shown in dark green, provides inputs to the rim, otxb, foxa, foxb, not, bra, elk, pks, and nrl genes. These particular relations were derived from studies (Davidson et al., supra, 2002) of the effects of an a-gatae morpholino antisense oligonucleotide (MASO). All QPCR data cited here are available at URL its.caltech.edu/~mirsky/qpcr.htm. An image of the α-GataE MASO phenotype is available at URL sciencemag.or/cgi/content/full/295/5560/1669/DC1. Other genes were entirely unaffected by this MASO treatment (Gene Network Update web site, supra).

The early cleavage stage events in endomesoderm specification take place in the $veg_2$ endomesoderm lineage, indicated in light green above the triple line at the top, and in the micromere lineage shown in lavender at the left. The central light green endomesodermal domain of the diagram in FIG. 1 portrays genes that ultimately (that is, by 24 hours) function in either endoderm or mesoderm; however, many of these genes are initially expressed throughout the $veg_2$ domain. As indicated above at the bottom, in three boxes, are shown several differentiation genes: skeletogenic genes on the left, mesodermal genes (mainly pigment cell genes) in the center, and endodermal genes on the right. The results shown in FIG. 1 indicate that, except for these differentiation genes, almost every gene in the network encodes a DNA sequence-specific transcription factor and that most of the linkages in the network consist of cis-regulatory interactions amongst these genes. There were also three genes encoding signaling ligands: the wnt8 gene, the delta gene, and the unknown gene responsible for the micromere-to-$veg_2$ signal (M3V2L). However, much of the regulatory work of specification is done by the cis-regulatory elements of genes encoding transcription factors. This is a general fact that can be extrapolated to all major developmental programs (Davidson, supra, 2001).

The model provides explanations of specific developmental processes. One example is spatial control by negative transcriptional interactions, illustrated here by the functions of the foxa gene. The foxa gene is expressed in the endoderm, as gastrulation proceeds, primarily in the foregut and midgut. Perturbations with α-foxa MASO resulted in a sharp increase in target gene transcript levels (Gene Network Update web site, supra), indicating that foxa encodes a repressor as indicated by the black barred lines emanating from this gene in FIG. 1. Two target genes are foxb and bra: foxb is expressed in the hindgut and blastopore (Davidson et al., supra, 2001 and Luke et al., *Dev. Growth Differ.* 39:285 (1997)) and bra in the blastopore (Rast et al., supra, in preparation, and McClay and Gross, *Dev. Biol.* 239:132 (2001)).

The network diagram indicates that the repression is spatial restriction due to foxa. Hence, study was carried out in which a reporter gene controlled by a cis-regulatory element of bra introduced into embryos bearing an α-foxa MASO. The result was that expression spread forward into the anterior gut. The expanded expression of bra in sea urchin embryos bearing α-foxa MASO is illustrated at URL sciencemag.org/cgi/content/full/295/5560/1669/DC1. Comparative observations have also been made on the embryo of a starfish, a distantly related echinoderm. Here too, foxa is used in endomesoderm specification as a repressor, servicing the same target genes as in the *S. purpuratus* network. The expanded expression of bra in a starfish embryo bearing α-foxa MASO is illustrated at URL sciencemag.org/cgi/content/full/295/5560/1669/DC1. Therefore, the network provides an explanation of why those target genes are expressed where they are: partly as a result of spatial transcriptional repression. In addition, the network indicates a temporal aspect of foxa expression. The foxa gene is seen to repress itself as well; combined with continuing positive inputs (from GataE and other factors), the result is an oscillation. For example, QPCR measurements of foxa mRNA showed that its level rises, falls, and then rises again late in gastrulation (Davidson et al., supra, 2002). All foxa QPCR data cited here are available at URL its.caltech.edu/~mirsky/qpcr.htm.

The network explains some of the phenotypes observed when given processes are perturbed, in terms of its consequential regulatory logic. For example, as previously shown, if β-catenin nuclearization is prevented by introduction of mRNA encoding the intracellular domain of cadherin, neither endodermal nor mesodermal cell types and structures appear. In default of β-catenin/Tcf inputs, the embryo becomes a hollow ball of ectoderm. It is noteworthy, however, that all the perturbation data underlying the network in FIG. 1 were obtained between 6 and 24 hours, long before any gastrulation phenotypes can be seen (Gene Network Update web site, supra).

Initiation of β-catenin nuclearization produces such a catastrophic result because multiple endodermal and mesodermal regulatory genes depend on a β-catenin/Tcf input. For these genes, only a few percent of control transcript levels survive cadherin mRNA injection (Davidson et al., supra, 2002, and Gene Network Update web site, supra). Another phenotype can be obtained when embryos were treated with a-gcm MASO. The result is albino larvae. An image of the albino phenotype produced by α-gcm MASO is posted on the Science Web site at the URL sciencemag.org/cgi/content/full/295/5560/1669/DC1.

Evidence for gcm autoregulation comes from QPCR data available at URL its.caltech.edu/~mirsky/qpcr.htm. The gene gcm is ultimately expressed in pigment cells (Ransick et al., supra, 2002), and a downstream target of gcm is the pks (polyketide synthase) gene, which is also expressed in pigment cells (see, for example, U.S. Ser. No. 60/384,962 and in subsequent publication Davidson et al., *Science* 295:1669-1678 (2002)). This product and other pigment cell genes under gcm control is required for synthesis of the red quinone pigment these cells produce. Upstream, the network shows gcm to be a target of the N signaling system because its expression is severely depressed by the introduction of a negatively acting N derivative (Davidson et al., supra, 2002) as previously described. Moreover, gcm expression begins in the single ring of mesoderm progenitor cells that directly receives the Delta micromere signal (Ransick et al., supra, 2002). Therefore, a sequence of DNA-based interactions exists that leads from the initial specification to the terminal differentiation of pigment cells and that explains the albino phenotype. Similarly, the network explains the α-gatae MASO phenotype. This treatment produces a severe interference with endoderm specification and gut development which is consistent with the branching regulatory effects of gatae expression indicated in the network.

The network explains the role of the signaling interactions required in endomesodermal specification in terms of their inputs into cis-regulatory systems. An exception is the early micromere-to-$veg_2$ signal. The gene encoding Wnt8 is itself a target of a β-catenin/Tcf input and it is, in addition, under the control of the early endomesoderm regulator krox. These inputs show how the autonomous nuclearization of β-catenin soon causes the Wnt8 loop to start up in all endomesoderm cells, strengthening the set of regulatory relationships indicated by the blue lines in FIG. 1.

The view from the genome provides a qualitative DNA-level explanation for the spatial domains of expression of many endomesodermal regulatory genes. No two of these genes have identical inputs: each cis-regulatory information processing system has its own job to do. The network shows that the downstream targets of a few of these regulatory genes, such as bra (Rast et. al., supra, in preparation), include differentiation proteins that were discovered in differential screens.

System-Level Insights into the Developmental Process

Physiological transcriptional responses flicker on after the advent of stimuli, then return to their ground state as for example, after changes in the level of nutrients or the advent of toxins in the bloodstream, or after the appearance of pathogens. In contrast, a feature of developmental transcriptional systems in higher (bilaterian) animals is that it moves forward, rarely reversing direction. This property is described in the developmental process exemplified herein and the network provides a mechanistic explanation. To illustrate this feature, views from the nuclei at successive stages were considered (FIGS. 2 and 3).

The initial events in endomesoderm specification occur in the micromeres and in the $veg_2$ lineage about fourth to seventh cleavage as described above. The maternal inputs provide the initial state, with respect to regulatory transactions. Maternal inputs are shown in blue boxes (see FIG. 1 for abbreviations) and blue lines, except for the autonomous nuclearization of β-catenin, shown in a hatched blue line. Four early zygotic transcriptional activations are indicated in red: Krox, Krl, Wnt8 in the endomesodermal domain (all of which require the β-catenin/Tcf input), and pmar1 in the micromere (mic) domain which Pmar1 requires also a material Otx input as suggested by cis-regulatory as well as perturbation evidence (Davidson et al., supra, 2001). Furthermore, directly or indirectly, pmra1 is also required for expression of the ligand conveying the early micromere to $veg_2$ signal (M→V2L). All other gene expressions and interactions in the network are indicated in gray.

There are two consequences of the initial zygotic transcriptional responses. The first was to begin the activation of the endomesodermal zygotic control apparatus by turning on the krox (Rast et al., supra, 2000) and krl [krüppel-like (Howard et al., *Development* 128:365 (2001))] genes in the $veg_2$ endomesoderm and the pmar1 gene in the micromeres. The 'second was as an immediate sequel, in both domains, was the unexpected engagement of repressive subnetworks (shown in green) of interactions that had the effect of stabilizing the initial definition of the endomesodermal and mesomere territories by cutting off the possibility of similar transcriptional activations elsewhere. The krl gene encodes a repressor that prevented expression of soxb1 in the endomesoderm, though it is expressed everywhere else (Howard et al., supra, 2001, and Kenny et al., *Development* 126:5473 (1999)). The SoxB1 protein antagonized nuclearization of β-catenin. The krl/soxb1 loop was an early lock-down device to keep the endomesodermal cells endomesodermal because they have elevated nuclear β-catenin from the start and to prevent other cells from going the same way. The pmar1 gene active in the micromeres also encodes a repressor. Its target was an unknown gene that produced another repressor of regulators of micromere-specific function. Like soxb1, it too is potentially active everywhere, except where it itself is repressed, which is the role accomplished by pmar1 in the micromeres.

Micromere regulators that were micromere-specific because of the pmar1 repression system included the gene that produces the Delta signal to the surrounding $veg_2$ cells and the regulatory genes that are responsible for installing the skeletogenic state of differentiation in the micromere progeny. These genes are the t-brain (tbr) gene, the ets gene, and the deadringer (dri) gene (Davidson et al., supra, 2002; Oliveri et al., supra, (2002).

The pmar1 repression system is shown in FIG. 2, B through G. These panels show whole-mount in situ hybridization displays, (Oliveri et al., supra, 2002). The gene, expression of which is being displayed, is shown at the upper right, and the mRNA injected into the egg is shown at the lower right, while the age of the embryo is shown at lower left. Panels B and C show expression specifically in micromeres of pmar1 and delta, respectively. Panel D shows expression of delta in all embryonic cells when pmra1 mRNA is translated everywhere, after injection into the egg. Exactly the same result is obtained if an Engrailed domain fusion is instead expressed (Oliveri et al., supra, 2002). Because the Engrailed fusion acts as an oligate repressor of pmar1 target genes, pmra1 normally act as a repressor. Expression of sm50, a skeletogenic differentiation gene, is shown exclusively in skeletogenic mesenchyme cells (Sucov et al., *Genes Dev.* 2:1238 (1988)) in panel E, and globally in embryos expressing pmra1 globally in panel F. Panel G shows expression of the skeletogenic regulator tbr in embryos expressing pmra1 mRNA globally. Panels F and G show that the whole embryo has been converted to a state of skeletogenic mesenchyme differentiation. Rounded cells form at 24 hours (shown in panel F), as compared to the control cells (shown in panel E), due to their tendency to behave mesenchymally. Thus, expression of the delta gene, the tbr skeletogenic control gene, and sm50, a skeletogenic differentiation gene, all occurred globally if pmar1 mRNA was expressed globally (Oliveri et al., supra, 2002). Almost the first thing accomplished by zygotic genes activated in both the $veg_2$ endomesoderm and the micromeres was to activate local negative control of otherwise global repressors of the respective states of specification. The network reveals active repression of these endomesodermal regulatory states in all the cells of the embryo except those where krl and pmar1 were respectively activated.

The system next proceeds to stabilize positively, and to expand, the endomesodermal regulatory state. The result was essentially to lock the process into forward drive of "commitment," and hardwired into the regulatory circuitry. Diagrams of these lock-down functions and expression of the complete regulatory state are shown in FIGS. 3A and 3B. The view from the endomesoderm nuclei extending from about sixth cleavage to mid blastula stage, about 7-12 hours of age, is shown in FIG. 3A. The Wnt8/Tcf loop shown in hatched blue interactions discussed above is a piece of this process, which consisted mainly of positive cis-regulatory feedbacks or auto- and cross-regulations which are shown in red interactions.

In the future mesodermal domain, the gcm gene autoregulated after its initial activation though the N pathway shown in hatched orange interactions. Similarly, the krox gene positively autoregulated, in addition to stimulating expression of the wnt8 gene, which locks wnt8 and krox in a positive regulatory embrace. The krox gene product also activated one of the transcription units of the otx gene (Davidson et al., supra, 2002; Gene Network Update webs site, supra, and Yuh et al., supra, 2002). In turn, Otx stimulated the krox gene. The otx gene this provided an input into the gatae gene, the importance of which was described above. The β-otx cis-regulatory system in turn responded positively to GataE input (Gene Network Update web site, supra. This result is a further positive feedback that links the gatae gene, a dedicated endomesodermal activator, into the stabilization circuitry.

As illustrated by the color coding in FIG. 3B, the regulatory state illustrated in FIG. 3A suffices to provide inputs to every one of the known transcriptional regulatory genes in the endomesodermal domain. The complete activation of the endomesodermal regulatory system viewed from the nuclei from midblastula to after mesenchyme blastula, essentially up to 20-24 hours of age, is shown in FIG. 3B. By this point, both endoderm and mesoderm specifications have become final, and all genes shown are being expressed. All results can be accounted for in terms of the set of inputs included in the color key at the bottom. Except for the Delta and Wnt8 signal-mediated inputs, which are transient, these regulatory inputs were achieved stabilization by the interactions shown in FIG. 3A. The drivers are Krox, Otx, GataE, Tcf, and the enhancer of Split-like factor that operates in this embryo downstream of N signal transduction.

After the above phase, the expression of the wnt8 gene falls off since the gene is repressed by one of the Otx isoforms (Davidson et al., supra, 2002; Gene Network Update web site, supra; Yuh et al., supra, 2002, and Li et al., *Dev. Biol.* 187:253 (1997)). During the late blastula stage, β-catenin disappears from the veg$_2$ endomesoderm nuclei (Logan et al., supra, 1999). By this phase, the regulatory system is locked in and has no further need of this input, which was important in the initial phases of the specification process.

The results described above show how an active cis-regulatory network produces the developmental phenomenon of progressivity and cell fate determination. Subsequently, epigenetic processes such as changes in chromatin structure, methylation, and the like can contribute to further stabilization of the differentiated state. However, the processes described in FIGS. 2 and 3 are sufficient to explain the progression from the initial maternal inputs, to early zygotic responses and stabilization of the state of specification, and thence to the full-fledged program of regulatory gene expression.

Developmental regulatory network analysis can be preformed in any organism where, for example, the genomics, gene transfer, and ancillary molecular methods are available. The cis-regulatory systems at the nodes of the network each process kinetic input information such as the rise and fall of the activities of the transcription factors to which they respond. Even from the first-stage model, which states the interactions that occur at each node, there emerge system properties that can be perceived at the network level. Examples are the features of the system described in FIGS. 2 and 3. These features explain the means by which maternal spatial cues are used to activate the zygotic transcriptional network, the progressivity of the developmental process, and its lock-down mechanisms. The network model relates these and other developmental features of the process of endomesoderm specification directly to the genome because it is couched in terms of cis-regulatory interactions at the DNA level. The model thus describes and represents the heritable developmental program. The DNA regulatory network coexists with other multicomponent systems that constitute the cell or organism. These systems execute biochemical functions, produce signal transduction pathways, and cause cell biological changes to occur. They sum to the majority of the working parts of the cell. Their mobilization is controlled by the transcriptional switches that hook them into the genomic regulatory control system.

The development of complex body plans is a definitive property of higher organisms and encoding the developmental process is a regulatory function of the genome. The evolution of body plans has occurred by change in the genomic programs for the development of these body plans (Britten and Davidson, *Quart. Rev. Biol.* 46:111 (1971)), and it can now be considered in terms of change in regulatory networks. Higher organisms such as bilaterians have about the same genetic toolkit, and in particular rely on substantially the same repertoire of regulatory genes to control the developmental organization of their body plans (Davidson, supra, 2001). Network analysis affords the means to focus on the exact consequences of differences in the use of these genes.

EXAMPLE II

Computational Methods for Constructing Cis-Regulatory Networks

The construction and design of gene regulatory networks can utilize computational tools to increase efficiency of the task. Several software tools are described that have been used in the study of embryogenesis and cell fate determination. These tools are suited to the iterative refinement of cis regulatory networks. They include: BioArray, a macroarray spot processing program; SUGAR, a system to display and correlate large-BAC sequence analyses; SeqComp and FamilyRelations, programs for comparative sequence analysis; and NetBuilder, an environment for creating and analyzing models of cis regulatory network or gene networks. Also described is the process used to build the model of the *Strongylocentrotus purpuratus* endomesoderm cis regulatory network or gene network.

The study of gene regulatory networks that underlie embryogenesis requires a synthesis of multiple approaches. Abstract model building, gene discovery, genomic sequence annotation, and sequence comparisons are all parts of the overall investigation. Computational tools can considerably aid in the process in several specific ways. In the course of describing the endomesoderm gene regulatory network of the sea urchin embryo (Davidson et al., supra, 2002) five such tools were developed. They can be used in conjunction with various related tools well known to those skilled in the art. These tools support, for example, each step of the network analysis strategy shown in FIG. 4 and are indicated in red in FIG. 4. As shown, FIG. 4 specifies more than a simple linear procedure. Network modeling can be used at every stage of the process to check the consistency of some or all experimental observations against observed behaviors of the network. The gray arrows show the forward path whereas the blue arrows indicate apparent inconsistent observations which allow looping back one or more steps to reconsider and reformulate the putative network architecture.

Figure 4:
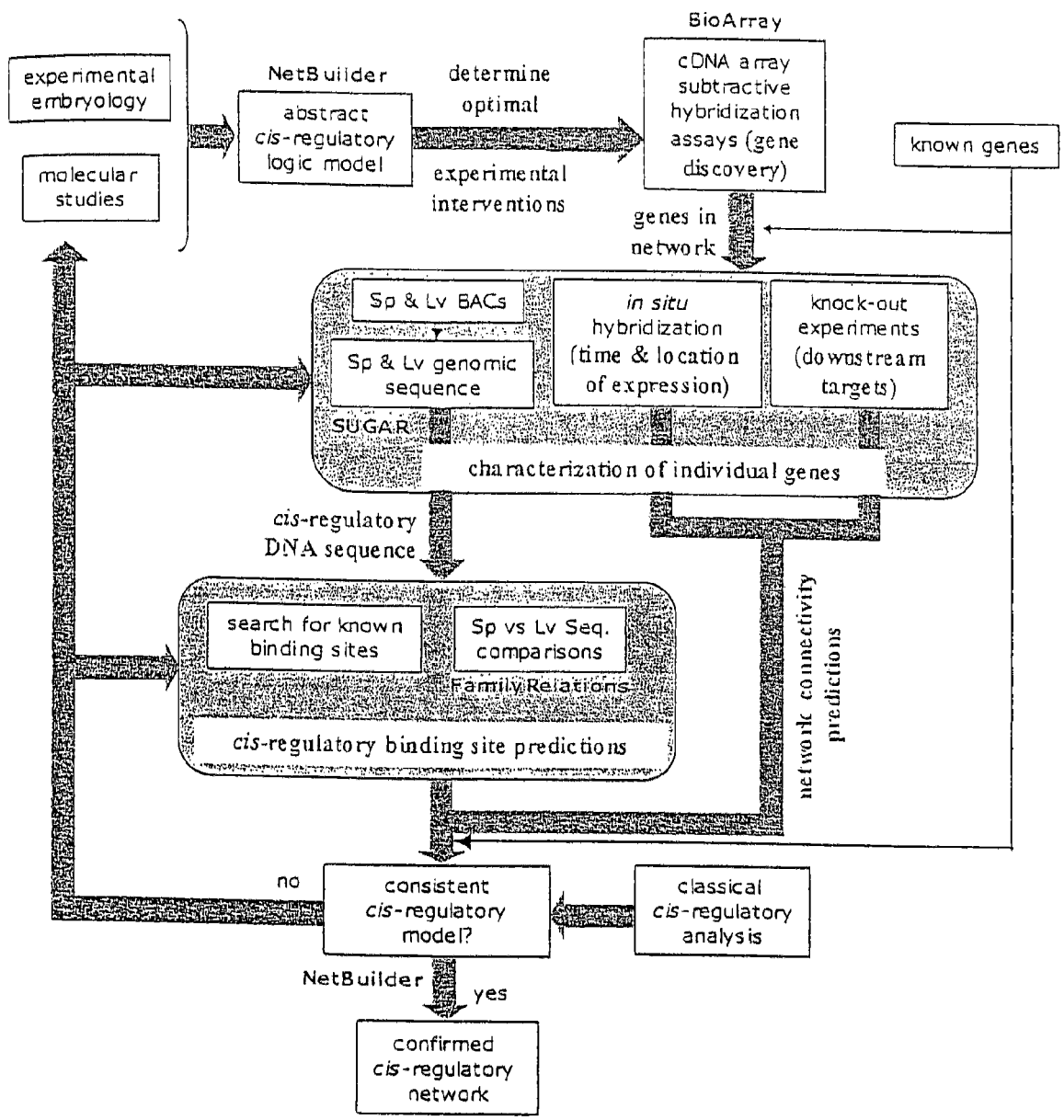
FIG. 4 shows a diagram of the strategy used to reveal DNA-based cis-regulatory networks.

FIG. 4 presents an overview of the approach to revealing DNA-based cis-regulatory networks and accompanying tools. The flow of FIG. 4 starts at the top left corner with information based on embryological studies. Molecular studies of sea urchins and other species over the last two decades provide a rich source of data.

By a process of iterative refinement, first an abstract explanatory model of all pertinent observations about the network of interest was constructed. The purpose of this early model is twofold. Firstly, the model serves to integrate disparate reported data and assists in developing a cohesive picture of the state of the art. Since relevant experimental results are usually of a mixed, qualitative and quantitative nature, the initial abstract models use a mixture of discrete (qualitative) and continuous (quantitative) logic. For example, in some cases the output of the system determines whether or not a gene is on in a given spatial domain, while in others its function is to control the amount of expression over time. These processes utilize distinct computational approaches. Additionally, a highly intuitive tool for building and testing such models termed, NetBuilder also can be employed, which is beneficial for analysis the of complex genetic regulatory systems.

The logical model description approach used allows one to incrementally increase the level of detail in the model as the network proceeds. Thus, the model becomes a progressive description of the network connections of a system. Simulation of the model provides a means of insuring against insufficient, inconsistent, or contradictory hypotheses.

In the sea urchin gene network, a subtractive hybridization on cDNA was used to discover genes that participate in a particular developmental process. This step is indicated at the top right of FIG. 4. To increase the evaluation accuracy of the radioactively-labeled, post-hybridization images, a software package, termed BioArray, was used. BioArray allows one to look beyond heavily expressed, ubiquitous, and house-keeping genes, to identify genes whose wild-type expression levels can be as low as ten or fewer mRNA molecules per cell (Rast et al., supra, 2000; Ransick et al., supra, 2002).

Three complementary approaches were used to characterize the genes isolated by the above procedure and in some instances, genes that were already known to be involved. These approaches are indicated in the green box in FIG. 4. The "knock out" experiments referred to in the green "individual gene characterization" box were conducted by using morpholino oligonucleotides and engrailed domain fusion proteins, both of which have the effect of "disconnecting" genes from their downstream targets. In situ hybridization and functional knock-out experiments were used to establish the time and location of expression of each gene, and to obtain direct or indirect linkages between given genes and those that operate downstream of them. This information allowed modification of the initial abstract cis regulatory network model with more detailed sets of identified genes and their connections. Additional cis regulatory analysis was needed to identify the putative binding site(s) of each input incident on a gene, and establish the logical relationships between multiple inputs that control a gene's transcriptional activity.

Genetic regulatory networks are based in the genomic DNA sequence (Bolouri and Davidson, supra, 2002), and in the context of cis regulatory networks, the relevant sequence is that which contains the genes in networks and their cis regulatory control elements. Since the total genomic sequence of the sea urchin is not completed, the construction of this network proceeded by isolating BACs (generally 120-150 kb) which contained the genes in the network. The BACs used to provide the DNA sequence surrounding genes of interest were known and publically available (Cameron et al., supra, 2000). Their sequence was then obtained to the point where it could be ordered completely, with only a few short gaps per BAC (Davidson et al., supra (2002). The gene network analysis has been carried out in *Strongylocentrotus purpuratus*, but in order to facilitate identification of cis-regulatory elements BACs were also isolated containing orthologous genes from another species, *Lytechinus variegatus*, for example, and the sequence of these BACs were obtained as well.

The cis regulatory analysis started with the annotation of the sequenced BACs. As described below, a well known annotation platform for this purpose was adapted. The Sea Urchin Genome AnnotatoR, termed SUGAR, allows one to search the BAC sequences with a large number of databases and DNA motif identification algorithms. Combining the results of all these searches, the gene of interest was identified within each BAC, the position of all other genes or possible genes was determined, and thereby the DNA sequences surrounding the genes of interest, within which the regulatory sequences should lie was found. As indicated in the blue box in FIG. 4, this regulatory genomic sequence was then compared in orthologous BACs from *S. purpuratus* and *L. variegatus*, for narrowing the sequence down to conserved non-coding regions, and the identified sequences considered to be potential cis regulatory modules.

The FamilyRelations program allows one to combine pairwise BLAST comparisons with more fine-grained analyses than done with SeqComp, a program designed for this purpose. Ultimately, a further cis-regulatory analysis was carried out using reporter constructs (Yuh et al., supra, 2002). This further analysis unambiguously confirms the regions indicated by FamilyRelations for function. Finally, novel or altered predictions are re-examined within NetBuilder and a new set of interventions can be designed for iterative refinement.

Each of the above-described software programs is described further below in greater detail.

Characterizing cDNA Macroarrays with BioArray

Figure 5A:
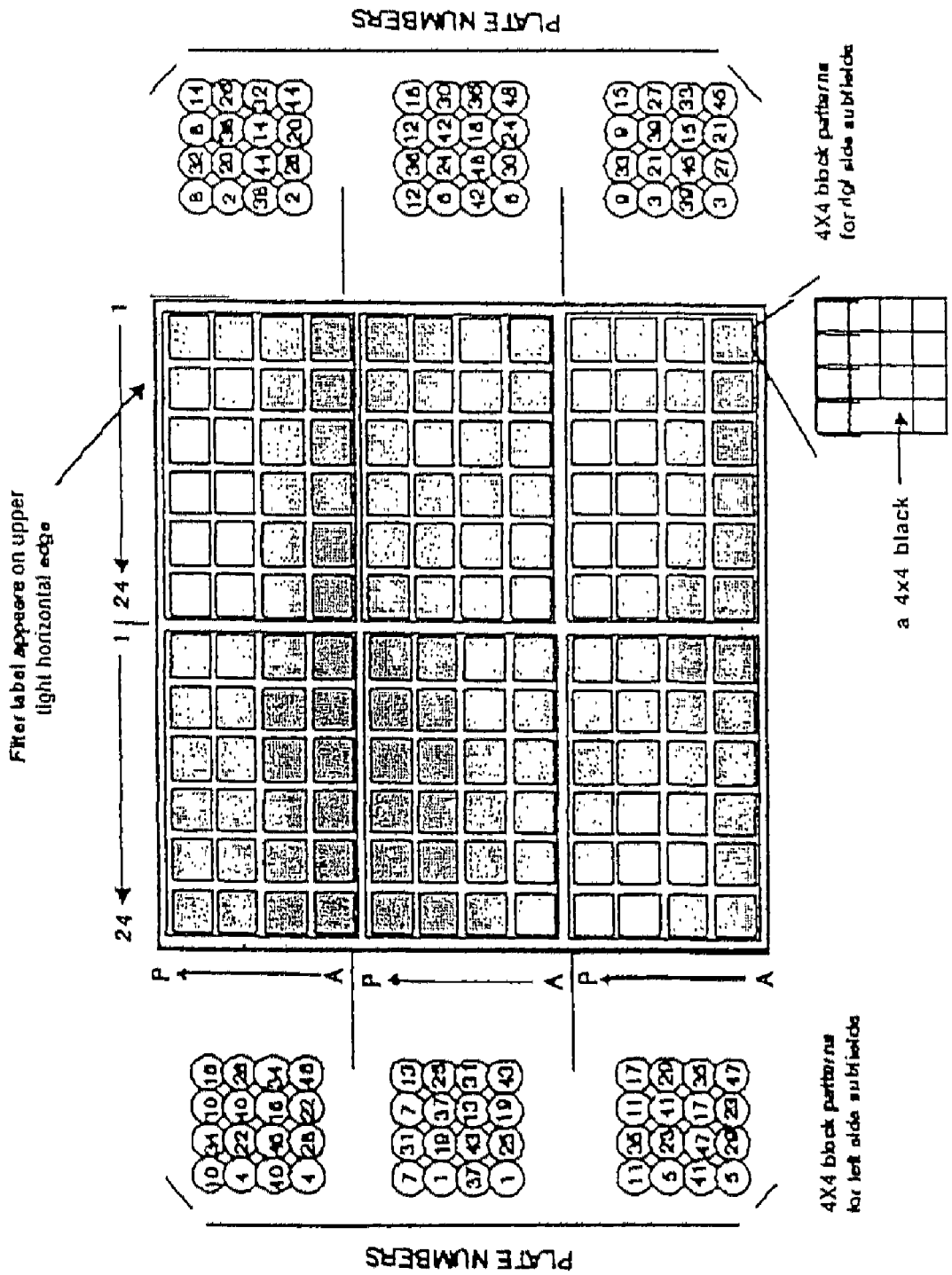
FIG. 5A shows the geometric layout of the microarray filters used and FIG. 5B shows the performance of BioArray, VisulaGRid and ArrayVision.

The gene discovery procedure involved the use of subtractive hybridization on nylon macroarrays spotted with bacterially amplified cDNA (.Rast et al., supra, 2000). The filters were approximately 22×22 cm. Bacterially amplified cDNA clones were spotted onto the filter in groups of 8 duplicates arranged in 4×4 blocks. Each gray box in FIG. 5A corresponds to a 4×4 arrangement of 16 blocks. These arrangements were in turn grouped into 6 individually labeled zones for indexing purposes. The block index numbers and characters are shown along the filter periphery (top and left). The total number of spot pairs per filter was 18,432. The pattern of duplicate arrangements within a block was such that each pair of spots had a unique geometrical relationship. This pattern was repeated throughout the filter. The spot indexing schemes used in the 6 zones of a filter are shown at the sides of the filter. The unique relations between spot pairs was used by the BioArray software package to resolve spot pair indexing ambiguities when hybridized filter images were assessed (Maier et al., *J. Biotechnol.* 35:191-203 (1994)). An schematic of the predefined duplicate patterns is shown in FIG. 5A. Further details of the filters, the sea urchin genome and DNA libraries, the hybridization procedure used, and related links can be found at the URL's sugp.caltech.edu; sea-urchin-.caltech.edu/genome and www.its.caltech.edu/~acameron/manual.html.

Figure 5B:
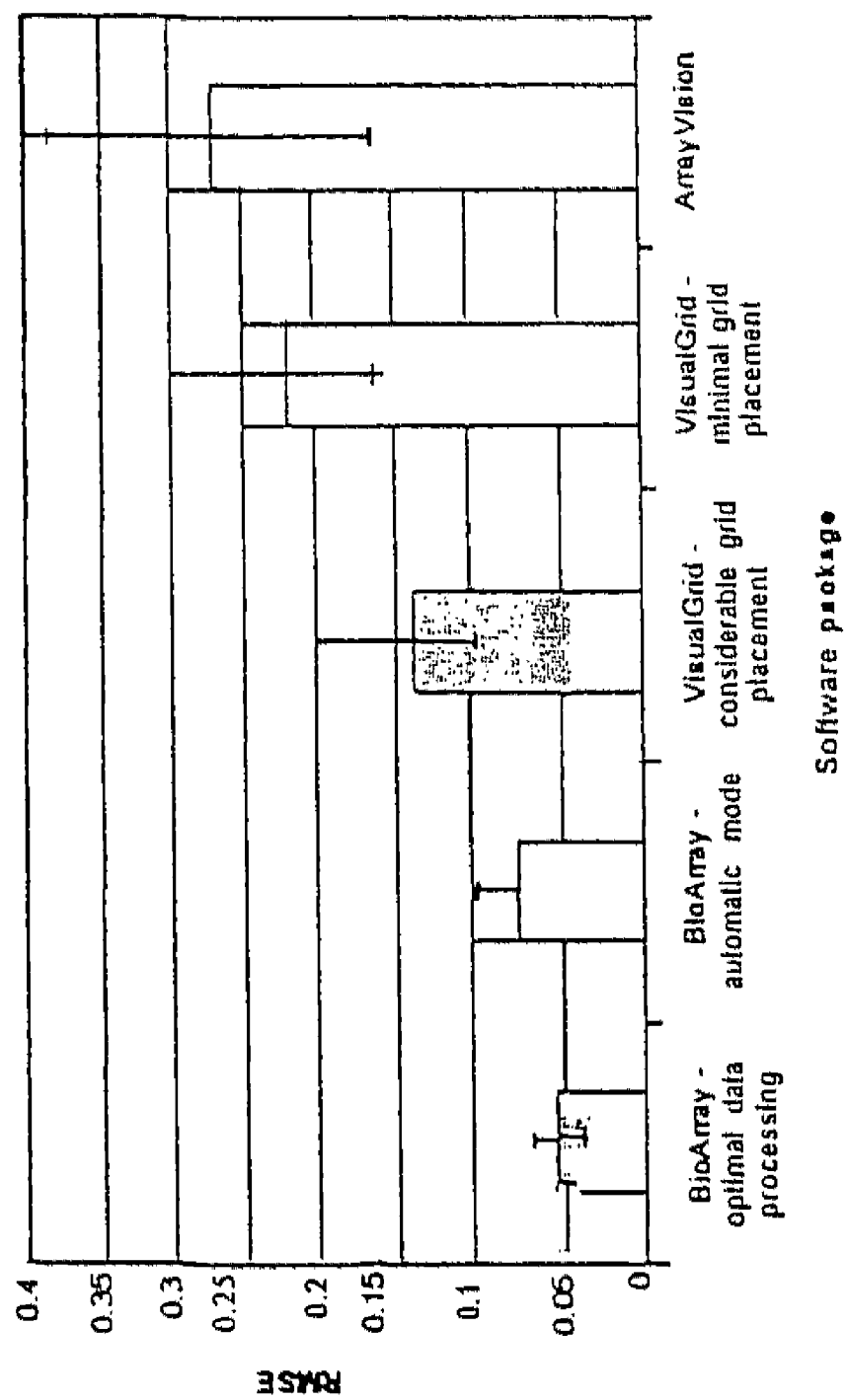

FIG. 5B compares the performance of BioArray for evaluating spot hybridization intensity images to two additional well known tools, Visual Grid and Array Vision, which can be found at the URLs gpc-biotech.de/technologie/int_genexpress.html and imagingresearch.com/products/ARV_dtls.htm. respectively. All three packages were used to analyze the same images produced by a phosphorimaging scanner.

Briefly, all spots on fifty randomly selected filter images were used. Distributed along the horizontal axis of FIG. 5B are the different software packages. The vertical axis shows the Root Mean Square Error (RMSE). Error was calculated as the difference in the measured intensities of a pair of spots in the same 4×4 block on a filter. All 18,432 spot pairs in 50 randomly selected filter images were used in the calculation. Using VisualGrid, it was possible to mark manually only the corners of a filter image ("minimal grid placement") or identify any number of corresponding spot pairs between two filters by hand. It was calculated as the difference in the measured intensities of a pair of spots in the same 4×4 block on a filter. All 18,432 spot pairs in 50 randomly selected filter images were used in the calculations. For the data shown as VisualGrid with "Considerable grid placement," as many corresponding spot pairs as was visually possible for each filter were identified.

BioArray offers similar choices: "BioArray automatic mode" refers to fully automated (single mouse button click)

filter evaluation by BioArray. "BioArray optimal data processing" refers to the case where users employed scatter plots of spot pair intensities (see FIG. 10) to identify "noisy" spot readings and then manually corrected any mask alignment errors using BioArray's fine-tuning mask editor (see FIG. 6). Comparison of the two left-most bars in FIG. 5B shows that the fully automatic procedure in BioArray produced results very close to the best that could be achieved through extensive tuning (referred to as BioArray with optimal data processing in FIG. 5B). It is noteworthy that, for the other packages, even extensive manual intervention, as illustrated by the example of manual grid placement in Visual Grid, results in much higher error than can be achieved using BioArray's fully automated filter evaluation function. Overall, BioArray evaluations are around two to five times more accurate than corresponding assessments with other packages. This greater accuracy is achieved through two measures: (a) greater accuracy in locating spots, and (b) a wider range of alternative measures of spot and background intensity. These are discussed in more detail below.

A range of factors such as filter warping, asymmetric growth of colonies, and imprecise robotic placement can cause spot locations to vary from a precise geometric grid. BioArray uses the predefined unique geometric relationships between spot pairs to identify unambiguous landmark features in the image, and applies nonlinear interpolation between these landmarks to correct for positional variations. The entire spot location and evaluation procedure can be performed with a single mouse button click, or the user can intervene to mark the four corners of the filter, if the image is overly warped, rotated, or otherwise distorted, or manually place a circular evaluation mask on top of any spot (illustrated in FIG. 6). After any such manual intervention, the user can optionally run a nonlinear interpolation algorithm to adjust the location of all other spot masks within the block, and the location of all other blocks, with respect to the manually placed masks.

By default, BioArray evaluates the intensity of each spot by evaluating pixel intensities within a circular mask placed on the spot by the above procedure. The size of the circular mask was adjusted by the user as shown in more detail in FIG. 6. The Editor allowed the user to move masks individually or in groups via options menu in the top right of the figure, and via the move arrows directly underneath. Red circles indicate masks which have been removed by the user. Using this approach, the user can overcome problems such as "overflow" from neighboring heavily hybridized spots, and geometric distortions in locations of spots. Unedited spot masks can be aligned to those which have been hand-tuned within the block, and the newly tuned block can be marked as an "anchor" via the "Align" and "Set as anchor" buttons on the bottom right of the figure. If this option is selected, BioArray will then adjust the locations of all other block masks on the filter by adding the new block's location to the list of definitive landmarks and recomputing the interpolations for difficulty to locate blocks. Furthermore, BioArray automatically adjusts the default mask size to account for different scanner resolutions.

FIG. 7 shows a typical evaluation mask superimposed on a filter image. For comparison, the raw image is shown in the window on the left. For the sake of legibility, only the top left corner of the filter is shown. The small blue circles are the evaluation masks placed in 4×4 blocks on the image. It is noteworthy the extent to which each circular mask coincides with a (dark) spot. The dark blue blocks are those where BioArray was able to unambiguously allocate a spot-pair identity to detected spots. The masks in the light blue blocks were also placed automatically by BioArray, but their location was determined by an iterative process of nonlinear interpolation and error minimization using the dark blue blocks as anchors.

The input to BioArray is the raw image file produced by the hybridization intensity scanner. Well known file formats such as GEL and TIFF are supported. The user interface of BioArray is similar to most Microsoft Windows applications and therefore has the same look and feel as Microsoft Word, Powerpoint, and Excel. The user interacts with BioArray by clicking the mouse on the filter image or on pull-down menus. For example, to configure the BioArray intensity evaluation procedure, the user can select from among the following options from pull-down menus. The user can choose to export data out of BioArray into a text file or a Microsoft Excel spreadsheet. The amount and type of data to be exported can be specified by selecting the appropriate menu items. The first two items in the menu provide short cut means of outputting commonly sought data (raw intensities, or intensities normalized by whatever measure was chosen in the normalization properties menu). The third menu item gives the user the option to specify a number of statistical measures of spot and background intensity. In the spot intensity field, Mean, Median, Quantile 80/90, Max and Min all refer to the histogram of pixel intensities for the pixels within the evaluation of mask of each spot. There are two options for calculating background. In the global background field, A1 refers to a reserved location which is left blank on all filters. The "periphery" option outputs the average pixel intensity for all pixels falling outside the rectangle containing all spots on the filter. In the local background field, the median and quantile measures are calculated for the histogram of all pixel values of all the spots in the block.

Spot Hybridization Intensity Metric

To allow the user to tune the intensity measure to particular conditions, and to facilitate comparison or mixing with data from other packages, BioArray offers five primary measures of spot intensity. Mean, median, sum and average of all pixel intensities within the spot can be measured. In addition, 80 or $90^{th}$ quantile of sorted pixel intensities within the spot can also be measured.

The sum and the average measures use an algorithm to locate the boundary of a spot, then sum and average all pixel values within the boundary. They are particularly useful for identifying very large spots automatically, because their total intensity will be disproportionately larger than the mean, median and quantile measures.

Background Metric

Background hybridization levels can vary from filter to filter and also within filters. Global background measures fail to account for variations within filters, while local background measures, because they are based on limited local information, can be noisy. The optimum measure of background will vary according to the degree of variation of background activity within a filter, and the choice of spot intensity measure. For this reason, BioArray allows the user to measure background levels either locally (per block) or globally (for the whole filter). The options for local background measurement are the median, $10^{th}$, or $20^{th}$ quantile of the spot intensity histogram for the block of interest. The global measures are either the average intensity of the filter periphery, or the intensity of a predefined pair of spot locations on the filter which are usually left blank for this purpose. The background value can be automatically subtracted from spot intensities, or the user can elect to view/analyze only subsets of spots with intensities above some multiple of background.

Normalization Metric

To make the spot intensity measure comparable across filters, the user can choose to normalize measured intensities by measuring local or global background as defined above or by averaging activity of control spots on the filter, selected by clicking on the pertinent spots in the image, or by measuring the total spot activity in the filter. The user can specify any subset of spots to be excluded from this last measure, for example if a portion of the filter is smudged.

Additional pull down menus allow the user to carry out other tasks described below.

Image Viewing

While BioArray data-processing operations are performed on raw images to maximize information extraction, the image presented to the human eye can be enhanced for ease of viewing. The user can sharpen edges in the viewed image, introduce false coloring by changing the levels of red, blue and green in the image, invert the image, zoom in/out, or use a magnifying glass to inspect the image in detail.

Exclude Subsets of Spots from the Data Set

The user can exclude subsets of spots from the data set in case, for example, of duplicate spot pairs whose intensity difference is greater than a user-defined threshold or of duplicate spot pairs whose activity is less than a user-specified multiple of the background intensity and in case of manually selected blocks of spots.

Produce a Scatter Plot of Selected Duplicate Spot-Pair Intensities

Duplicate spots should ideally exhibit the same level of hybridization and hence image intensity. Plotting the intensities of duplicate spot pairs against each other produces a scatter plot around the 45 degree line representing the ideal case. In BioArray the user can draw such a scatter plot with a single mouse click and inspect outliers (i.e., duplicate spot pairs whose intensities are dissimilar) by double clicking the mouse on any point in the scatter plot.

Figure 8:
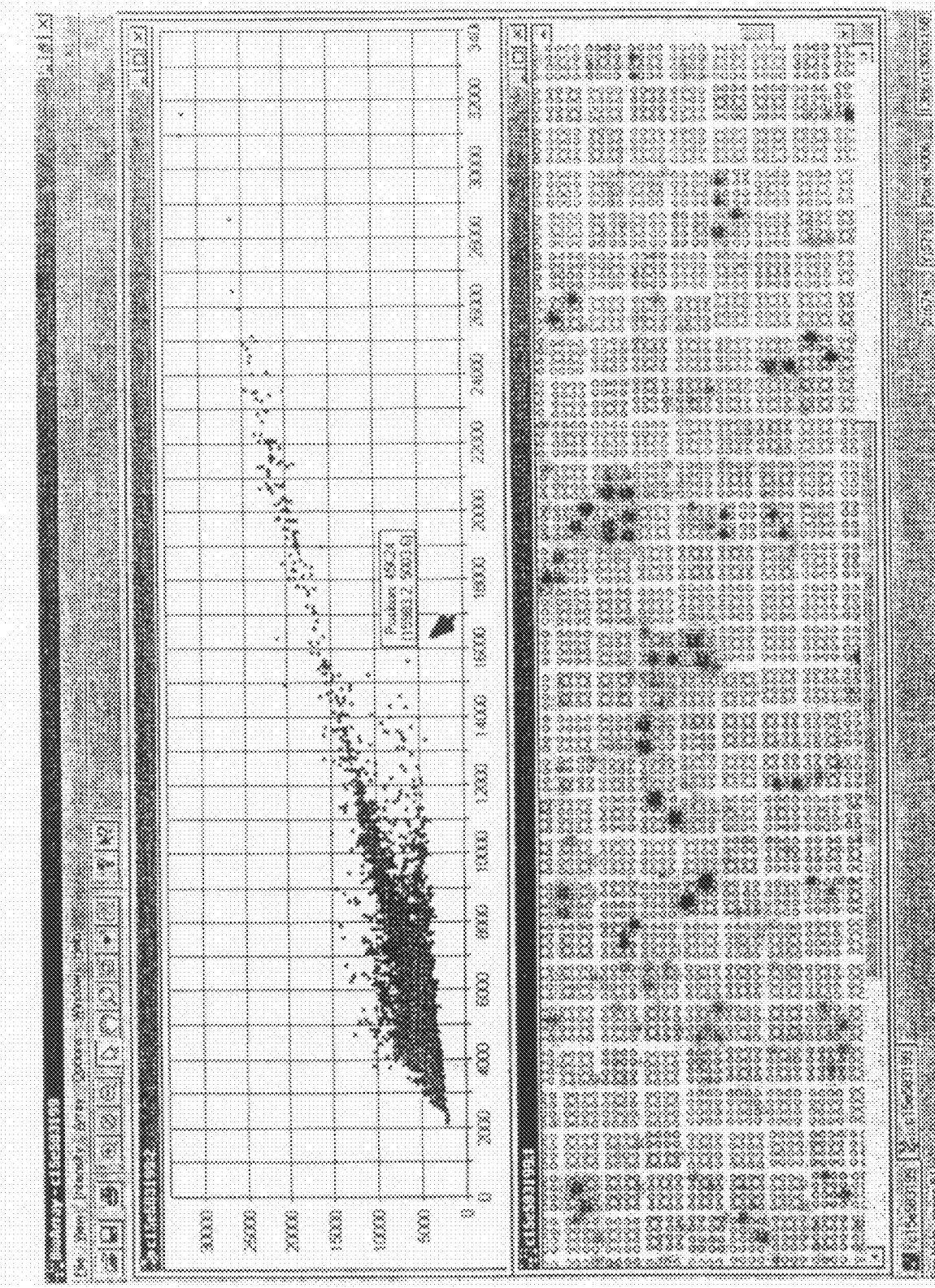
FIG. 8 shows a scatter plot of spot pair intensities generated by BioArray for the filter shown in FIG. 8.

FIG. 8 shows the scatter plot for the filter shown in FIG. 7. The plot was generated by double clicking the mouse on a point in the scatter plot indicated by the black arrowhead. In the BioArray filter image window below the scatter plot (here zoomed in for legibility), BioArray has automatically highlighted the block containing the spot pair by placing a dotted red square around the block. It is noteworthy that the unique filter coordinates of the block are also given in the scatter plot window. In this example, one of the two circular spot evaluation masks appeared to partially overlap the corresponding spot. If these spots are of sufficient interest, the user can manually edit the location of the errant spot mask in this block to improve the readings and reduce the error for this particular spot pair. In this manner, it is possible to iteratively refine the spot evaluation procedure for best results.

BioArray also allows automatic comparison of two individually assessed filters. To perform this task, filters were normalized in the same manner. The user can select the differential display colors for each filter. Generally, green is used for control (e.g., presubtraction image) and red for "treatment" (e.g., postsubtraction image) to produce results similar to microarray fluorescence images. It is also possible to select subsets of spot pairs by level of activity above background and other intensity measures. Double clicking the mouse on a spot in the differential activity display highlights the location of the two spots in the original filter images (dotted red squares in the filter images). Using this facility, the user can iterate through the filter assessment and comparison process to optimize readings for spots of interest.

Figure 9:
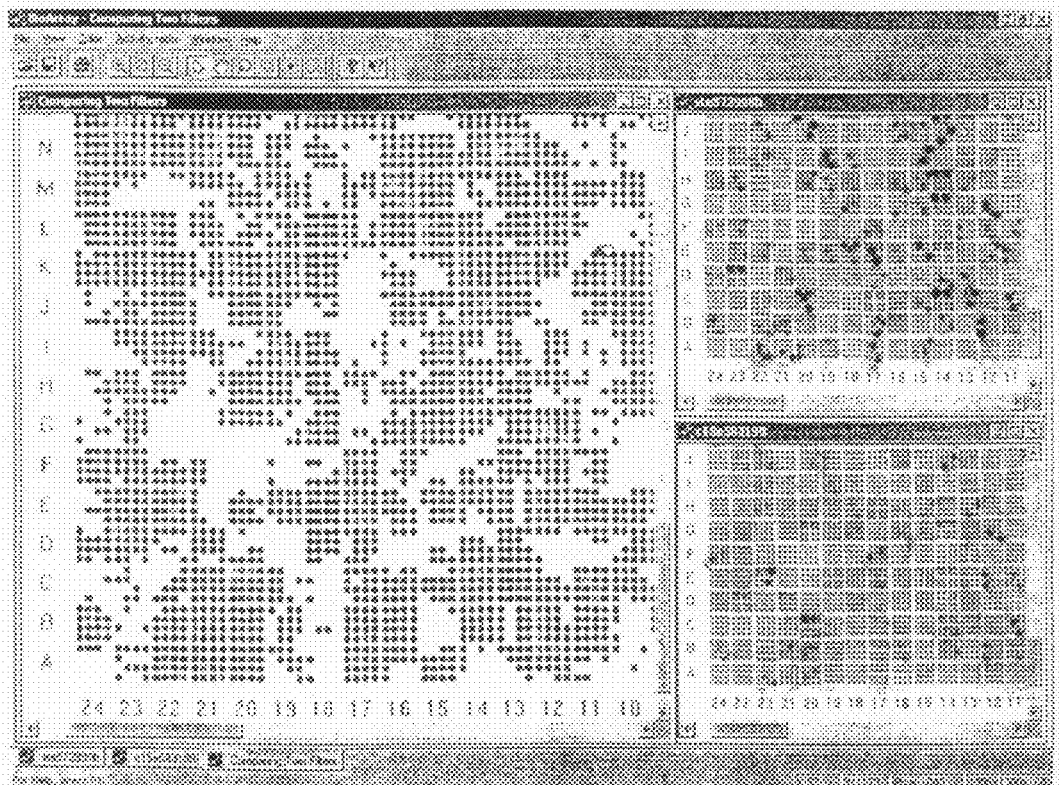
FIG. 9 shows comparison of two filters using BioArray. The bottom left-hand corners of two filters are shown in the windows on the right. The window on the left shows the visual comparison of the evaluated spot intensities in the two filters.

An example of comparison of two filters using BioArray is shown in FIG. 9. The bottom left-hand corners of two filters are shown in the windows on the right. The window on the left shows the visual comparison of the evaluated spot intensities in the two filters. Clicking the mouse on any block in the comparison window highlights the corresponding blocks in the individual filter images (dotted red rectangles). For this example, activity in the top filter is shown in red and activity in the bottom filter is shown in green. Using filter block 20C as an example, it can be noted that spots which were more active in the top filter have a red hue (e.g., second from right on the bottom row of the block), while spots which were more active in the bottom filter have a green hue (e.g., top left spot in the block). The brightness of the colors was proportional to the level of hybridization intensity in the contributing spots. Many spots have a dark brown color resulting from superposition of low intensity spots in both filters. Various menu options allow the user to tailor and configure the filter comparison process. For example, the user has elected to remove all spots whose activity was less than a threshold value (blank areas in the figure, see text for details).

Finally, all data generated by BioArray can be output automatically to Microsoft Excel, for example, should the user wish to perform further analysis. BioArray was developed with Genetssix Q-Bot robotic technology (see URL genetix.co.uk) comparability.

Annotation of BAC Sequences with SUGAR

The Sea Urchin Gene AnnotatoR, SUGAR is built on top of the publicly available Genotator annotation workbench, available at URL fruitfly.org/~nomi/genotator/ (Harris, supra, 1997), which in turn was built on the bioTkPerl widget library originally developed by Gregg Helt at UC Berkeley. Apart from some minor differences (for example, in SUGAR reverse strand features are mapped onto the forward strand and displayed in a different color) most of the look and feel of Genotator is retained. One difference with Genotator is that SUGAR includes several additional analyses. By summarizing all related search results in a single graphical window, SUGAR provides a convenient overview which can be interactively interrogated for more detail.

Figure 10:
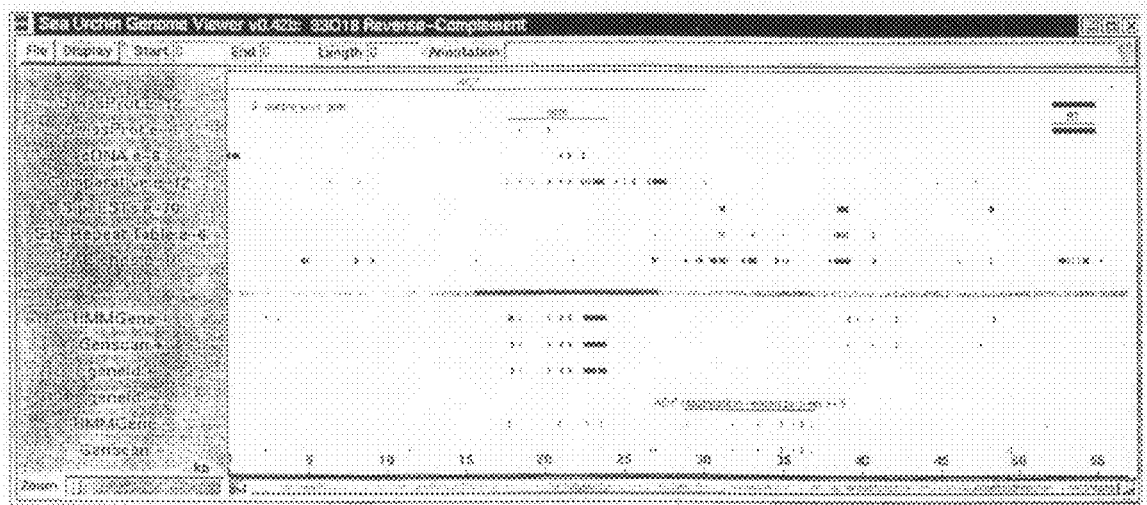
FIG. 10 shows an annotation of the S. purpuratus BAC sequence containing gcm displayed in SUGAR.

SUGAR generally displays one BAC at a time, generally 120 kb-150 kb of concatenated contigs of different lengths. Individual contigs are shown in alternating colors in the main SUGAR window. In FIG. 10, an annotation of the *S. purpuratus* BAC sequence containing glial cells missing gene (gcm) (Ransick et al., supra, 2002) is displayed in SUGAR. The gcm coding sequence is at the center of the 56-kb BAC, oriented so that the 5' end of the coding sequence is to the left. The SUGAR display is divided in two by the line indicating the orientation and location of the contigs. For example, above this line the matches to experimentally obtained sequence data are displayed, including (from top to bottom) matches to Swiss-Prot, the location of the cDNA sequence, matches to the *Lytechinus variegatus* sequence, and the locations of ESTs, BAC ends, and repeats from the Sea Urchin Genome Project. The stringencies at which the matches were selected are displayed next to the database resource used. Data are stored in two formats: ACEdb available at URL acedb.org and GFF (General Feature Format), available at URL sanger.ac.uk/Software/formats/GFF, which is a generic format useful for data exchange. The generic format can be used, for example, with the FamilyRelations program described below.

SUGAR presents the user with a variety of useful information simultaneously FIG. 10. BLAST search results against a number of databases are displayed in graphical form aligned against the BAC sequence. These include SwissProt, GenBank, known cDNAs, sea urchin ESTs, *S. purpuratus* repeat sequences and BAC ends. All of the sea urchin databases are accessible from the Sea Urchin Genome Project, available at URL sea-urchin.caltech.edu/genome.

SwissProt hits were displayed at two different levels of significance for ease of visual analysis. Forward strand hits were colored red, while reverse strand hits were shown in green. Clicking the mouse on a colored bar representing a SwissProt hit opens up another browser window which displays details of the sequence alignment and other information. In addition, the top 25 hits were listed in descending order of significance. Clicking on an item in this table takes the browser to the more detailed alignment view.

The protein matches and exon detection markers were color-coded to distinguish between forward and reverse strand hits. The BAC-end database contains 76,000 BAC end sequences (Cameron et al., supra, 2000). The "unique" matches which are matches to three or fewer BAC-ends are colored orange, and the "repeats" matches which were sequences matching larger numbers of BACs were colored black. Clicking on a block opens a new browser display which shows the results in more detail. At the top of this display is a more a detailed graphic of the BAC-end alignments. This display is followed by a table of unique back end accession names, the individual alignment information, and histograms of the number of BAC-ends in a repeat block.

It is noteworthy that in the main SUGAR display window (e.g., FIG. 10), below the line representing the BAC sequence, SUGAR displays hits by a number of gene/exon identification programs. These are MMM gene available at URL cbs.dtu.dk/services/HMMgene; Genscan available at URL genes.mit.edu/GENSCAN.html, and Geneid available at imim.es/software/geneid/index.html. These are also of use in predicting genes for which there is no extant sequences in either the SwissProt or the Sea Urchin genome project database. Forward-strand hits were displayed in blue and reverse strand hits in green. Slider controls allowed the user to zoom in and out and pan right and left as desired.

Identification of putative coding or regulatory regions using SUGAR was reviewed and weighed on a case by case basis. For example, a region marked with many "SU repeat table" hits and displaying black (repeat) BAC-end markings was more often not considered a significant regulatory or coding segment, even if other searches such as SwissProt or any of the exon finders also showed hits in that exact region (as might occur in the case of a recently inactivated pseudogene). Similarly, a region in which multiple results concur was assumed to be more likely to be a true positive.

SUGAR is available at sea-urchin.caltech.edu/software/SUGAR.

Selection of Putative Regulatory Sequences with Family Relations

Comparison of BAC sequences containing homologous genes from L. variegatus and S. purpuratus provides a powerful evolutionary means for identifying cis regulatory domains of genes. The sequence comparison algorithm Seq-Comp compares two BACs using small sliding windows of programmable length which are usually from 20 to 50 base pairs. It is similar in function to the Dotter algorithm by Sonnhammer and Durbin, *Gene* 176:GC1-GC10 (1995). For each "word," or contiguous sequence of bases in a window, in a reference sequence a list of the ten best matches is identified and marked with a similarity index. Differences between the evolutionary comparison described above and other approaches to phylogenetic footprinting (Wasserman et al., *Nat. Genet.*, 26:225-228 (2000) are that the above search is performed exhaustively using the small sliding window on very large sequences (10-50 kb per run) excised from BACs after annotation. Matches are allowed between any two windows irrespective of their relative locations on the BACs and reverse complement matches are detected. A separate program, FamilyRelations, presents a graphical user interface to SeqComp and also offers a number of additional features.

The main view of FamilyRelations is shown in FIG. 11. In this view, the analysis compared BAC sequences surrounding the glial cells missing gene (gcm) in *S. purpuratus* and *L. variegatos*, two sea urchin species that are approximately 50 My diverged (Gonzales and Lessios, supra, 1999). The display is divided into three windows. To the right are the user controls. These include menus for selecting the sequences to be compared, and a slider with which the user specifies the threshold for displaying SeqComp matches. Any number of pairwise comparisons can be loaded, including BLAST comparisons. The BLASTN comparison was turned off in FIG. 11, to avoid confusion in the display.

On the lines representing the BAC sequences, TBLASTX matches to the cDNA sequence of Spgcm were graphed in red. The regions of high similarity extended well beyond the red exons. In addition to the matches displayed "in register," that is, as parallel lines, there were a number of matches that fell out of register, including several that correspond to more than one region on the other BAC. These matches showed elements duplicated within and between the BACs and represent, for example, simple sequence repeats. The top left window displays the SeqComp similarity histogram. The similarity matched the entire *S. purpuratus* BAC (57 Kb) and the corresponding region of probable orthology in the *L. variegatus* BAC (100 Kb of which 62 Kb is shown). The horizontal axis represents one of the two compared sequences (the "reference" sequence). The vertical axis, which displays the match quality, was automatically truncated to show matches above a preselected analysis threshold, calculated from the background expectation level for random sequences. The dotted blue line shown in the histogram window marked the user-specified display threshold.

The histogram peaks correspond to regions of highest similarity between the two sequences. The regions corresponding to peaks that exceed the user-specified threshold are displayed in more detail in the bottom left window. The horizontal black lines at the top and bottom of this window represent the total length of each of the two compared sequences. The bundles of blue lines connecting the two sequences link corresponding matches in the two DNA strands. Selecting any region in this window opens up a more detailed view of the relationship between the two sequences.

An example of a detailed view, matching the region selected by the blue boxes in FIG. 11, is shown in FIG. 12. The top window was minimized to show only the sequence line and contains a flattened representation of the matches and is used for selecting and manipulating them. The middle window is a zoomed-in version of the bottom left window in FIG. 11 and the red rectangles on the sequence line show the cDNA matches from FIG. 11 in more detail. The actual sequences of the regions inside the blue rectangles in this window were displayed in the bottom window. Matching regions were displayed with red text, and lines connect the matching base pairs.

In addition to the above, FamilyRelations can also be used to simply display annotation data, or generate a "dot plot" of similarity regions between two sequences. Again, the user can zoom in, zoom out, or pan sideways, as required.

Because FamilyRelations is written in the machine-independent Java language, the software can run in Windows, Unix, and Mac OS X environments. SeqComp and FamilyRelations, and an accompanying tutorial, are available at URL family.caltech.edu.

Building Logical Models of Regulatory Networks with NetBuilder

NetBuilder is an environment for constructing mixed, qualitative and quantitative logical models of Cis Regulatory Network, also known as Genetic Regulatory Networks (GRNs). It is based on principles commonly used in electronic engineering to model mixed, analog-digital integrated circuits. The user interface is graphical and does not require any specialist knowledge or training. NetBuilder allows modelers to build graphical representations of GRNs by placing predefined network components on a canvas, and drawing connections between components to represent interactions. NetBuilder is useful for analysis of complex gene regulatory systems.

Figure 13:
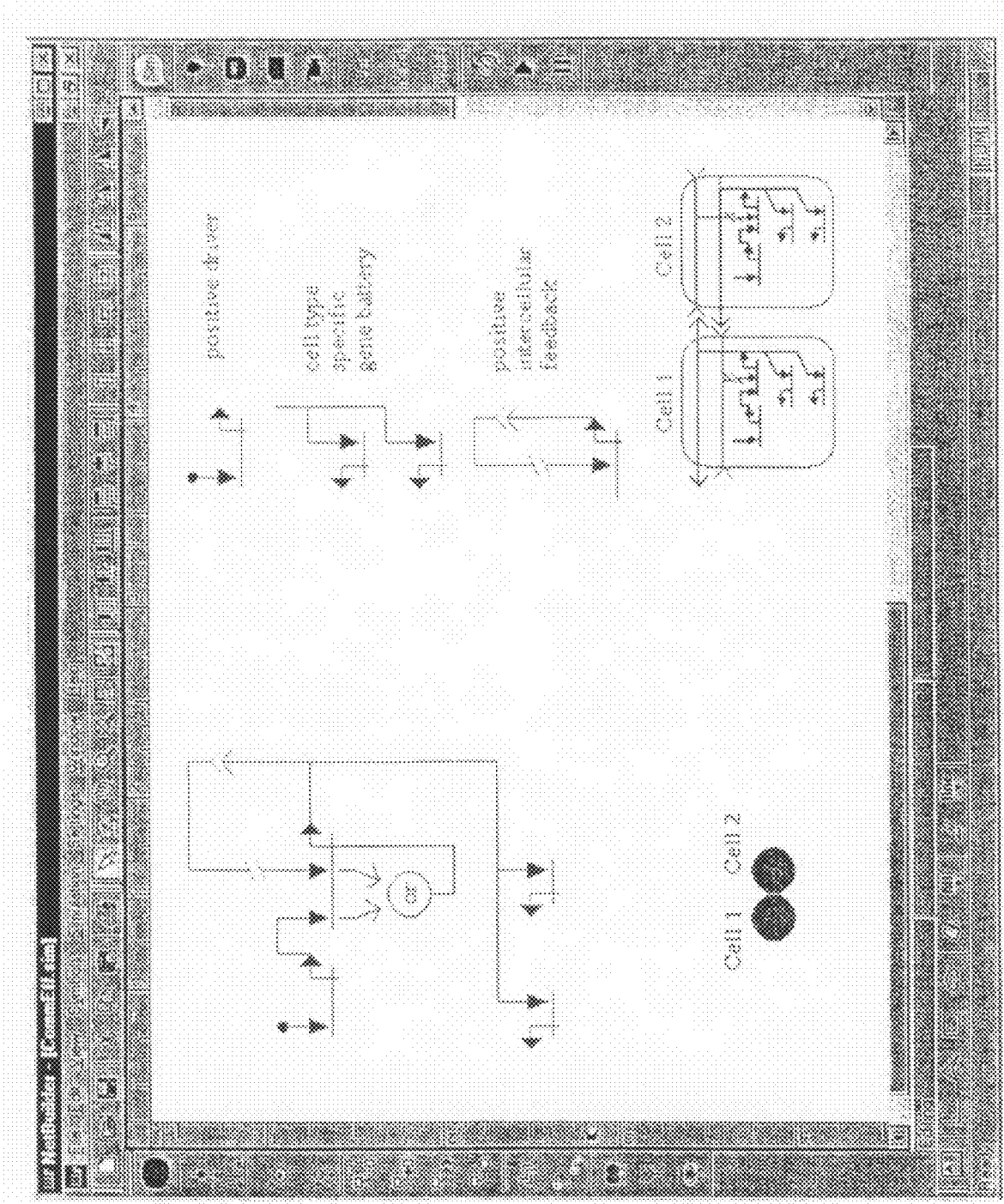
FIG. 13 shows the NetBuilder network editor view.

As shown in FIG. 13, the main NetBuilder screen, called the network editor, has the look and feel of common Microsoft Windows applications and offers many of the same menus and tools. In the center is the user work-space or canvas. There is a line of pull-down menus at the top-left of the screen. Below it are a set of common, general-purpose action icon buttons (e.g., save, print, zoom, and select). A set of general-purpose drawing and annotation tools was provided in the tool bar below the canvas window. The tools in these bars are substantially the same as those found in Microsoft PowerPoint, Word and other compatible packages. The column of icons to the left of the user workspace provides shortcuts to the NetBuilder network symbol library which can also be accessed through the pull-down menus. To draw a new network, the user places the appropriate symbols on the canvas by pressing the symbol buttons. The buttons are grouped into four categories. Starting from the top on the left margin in FIG. 13 and taking each category in turn a description of each of these features is provided below.

The top category defines four types of symbols for cis regulatory network elements. From top to bottom these are:

Scalars. Scalars were used to model effects such as the amplification of the effect of one transcription factor by another, or the existence of a maternally inherited factor. The user can specify a linear amplification coefficient, and a "Hill coefficient" to specify the degree of nonlinearity of the effect of the scalar factor as appropriate.

Genes. The symbol for a gene comprises a ninety degree bent arrow symbolic of the transcriptional apparatus, and a horizontal line in two parts: the portion behind the bent arrow symbolizes the regulatory region, while the portion forward of the bent arrow symbolizes the coding region.

The convention used in NetBuilder is to describe interactions outside of the nucleus above genes and to describe cis regulatory interactions on DNA as arrows or bars which impinge on the line representing the cis-regulatory DNA. This convention usually leads to a convenient arrangement of genes in a horizontal line, with the space above this line representing interactions between gene products, and the space directly below each gene representing the consequences of the cis-regulatory interactions governing the transcriptional activation of that gene.

Interaction symbols. Interactions were modeled as logical And, logical Or, or algebraic addition or multiplication. The logical operators can be Boolean or continuous-valued. For a Boolean logical Or, if any one of the inputs is active, the output will be active. For a Boolean logical And, unless all inputs are active, the output will be inactive.

Switch elements. These elements were constructed from the interaction elements above. The following commonly encountered elements are available as NetBuilder library elements to speed up network capture:

(a) A bistable switch was used to indicate processes which, once they are activated, remain active until overridden by another event. An example would be a conformational change in some proteins.

(b) Threshold and comparison symbols were used to describe the relative significance of an interaction effect or a gene product. They include symbols for comparing two interaction effects or concentrations, and for determining whether an effect or concentration is above some threshold.

The second group of symbols provides a variety of connectors with which to link up the components of a network. The connectors transmit the outcome of interactions or states of genes from one point to another. Different symbols were provided for the sake of diagrammatic clarity. The last of the four connectors provides a generic shorthand symbol for negation. Depending on the functionality of the receiving component, this can mean a logical Not, a change in the sign of input, or the reciprocal of the input.

The two buttons that make up the third category of NetBuilder icons offer drawing features useful for editing GRNs. When the top button is pressed, lines are automatically drawn with horizontal and vertical segments only. The button underneath this automatically updates the connector colors; i.e., when the button is pressed, the connectors assume the same color as the symbol whose output they transmit.

The fourth category of symbols is constituted by "cells," "receptors," and "define contacts." NetBuilder has been produced to allow the modeling of GRNs in multi-cellular embryos. Clicking in the cell button (red filled circles) places a symbolic cell on the canvas (a red circle). The user can place a collection of such "cells" together to draw cartoons of a growing embryo at different stages of development. An example of this is the cartoon underneath the network drawing in FIG. 13. Different groups of cells in time and space can be grouped together and specified to have different initial or inherited conditions. The receptor library element is used as a generic intercellular signaling symbol. The user can edit the attributes of receptors (e.g., location, delay, degree of activation nonlinearity) using a menu that pops up when the "Define contacts" button is clicked.

As shown in the right hand side of the canvas in FIG. 13, the user can place any number of additional comments and annotations on the canvas without interfering with the simulation model represented by the network and cells drawn on the left hand side of the canvas. All of the NetBuilder symbols described can be enlarged, shrunk, or elongated by the user as necessary.

As described by Bolouri and Davidson, (supra, (2002)), and in reference to the network diagram described therein in which all interactions between genes and their products are illustrated as the View From the Genome (VFG). The circuit in FIG. 13 represents an example of a VFG. Briefly, the figures on the left-hand side of the canvas represent the NetBuilder model. The two red circles below the network model represent the cells modeled. The modeled network element in each cell is shown at the top left of the canvas. The figures on the right-hand side of the canvas are annotations the user has added optionally to facilitate understanding, and to document the model.

The example of the network displayed implements an intercellular positive feedback loop between two cells. The green gene was assumed to be activated by a maternal or other localized factor. The blue genes were engaged in self-reinforcing intercellular signaling and are modeled as driving downstream gene batteries (pink genes). The network has the characteristic that arbitrarily small levels of activity driving the green gene in either cell will cause the gene batteries in both cells to become activated and remain locked on. The two horizontal tool bars just above and below the editor canvas provide general purpose file management and figure annotation facilities. The two vertical tool bars to the left and right of the editor canvas provide NetBuilder editing and simulation facilities as described in the text. The user need only define such a "View from the Genome" and start the simulation. NetBuilder will automatically track the different states of the GRN in different cells. The simulation outcome can be viewed in two ways.

First, the "View from the Nucleus" (VFN) for any particular cell type can be viewed by simply clicking on the cell of interest and then selecting the probe symbol located at the top of simulation toolbar to the right of the canvas. The outputs of those genes which are active in the cells of interest are given user-defined colors, while inactive outputs are shown in gray. An example of the set of VFNs generated by the intercellular circuit of FIG. 13 is shown in FIG. 14.

Briefly, the state of each of the two cells (defined in FIG. 13) is shown at two points in time. Top left, cell 1 just after activation of the green gene. The blue gene has become active, but has not yet received a signal from cell 2. Top right, cell 2 at the same amount in time. The receptor on the cell has become active due to signal from blue gene in cell 1, but nothing else is yet activated as gray lines indicate inactivity. Looking at the cartoon cells at the bottom of these images, a thick black border indicates which cell is being viewed. The color of the "cell" is red if the gene being monitored is active, gray otherwise. The two bottom views show the same two cells some time later, when all components of the intercellular feedback network have become active in both cells. In all these views, the simulation icons are colored since active and the editor icons are gray since inactive. The opposite is true when NetBuilder is in edit mode (see FIG. 13). Presentations using those VFG and VFN conventions can be seen for the real regulatory model in Davidson et al., supra, 2002.

Second, the simulation can be viewed as a time-course plot of the level of expression of any gene in any cell. An example is shown in FIG. 14B which represents a simulated outcome for the circuit illustrated in FIGS. 13 and 14A. Briefly, time-course activities for the green gene in cell 2, and the blue genes in both cells are shown. The activity of the green gene was low and short lived, but was nonetheless sufficient to activate the blue genes in both cells to saturation.

As with the network editor, the simulation facilities provided by NetBuilder use graphical icons to provide the user with a simple means of controlling the simulation. The simulation icons are listed in a column to the right of the editor canvas. The simulation icons allow the user to set the start and end time of simulations, set or reset the state of any gene or switch in the network, plot the time course activity of any gene, and save the simulation result.

During the course of construction of the *S. purpuratus* endomesoderm network, the complete network, and individual subcircuits of interest were modeled in NetBuilder at various points. Some example files and a current version of NetBuilder are available at URL strc.herts.ac.uk/bio/Maria/Tool.htm.

Described above is a set of software tools which facilitate the construction of cis regulatory networks. Although the description is necessarily linear, the process can be both non-linear and iterative. These software tools aid in the process of building and testing cis regulatory networks and can be used, for example, in conjunction with or in substitution with other methods, software tools or systems well known to those skilled in the art. Current versions of the software algorithms described herein are available freely via the Internet (see individual listings above).

Throughout this application various publications have been referenced within parentheses. The disclosures of these publications in their entireties are hereby incorporated by reference in this application in order to more fully describe the state of the art to which this invention pertains.

Although the invention has been described with reference to the disclosed embodiments, those skilled in the art will readily appreciate that the specific experiments detailed are only illustrative of the invention. It should be understood that various modifications can be made without departing from the spirit of the invention. Accordingly, the invention is limited only by the following claims.

What is claimed is:

1. A method of promoting skeletogenic mesenchyme differentiation of a progenitor cell, comprising exogenously activating, in the progenitor cell, a transcription repressor for a global inhibitor of a skeletogenic differentiation gene, thereby activating the skeletogenic differentiation gene and promoting skeletogenic mesenchyme differentiation resulting therefrom, wherein the transcription repressor is pmar1.

2. The method of claim 1, wherein said progenitor cell is a zygote, a pluripotent stem cell, a pluripotent lineage specific progenitor, a non-committed embryonic cell, or a terminally differentiated cell.

3. The method of claim 1, wherein the transcription repressor is exogenously introduced into the progenitor cell.

4. The method of claim 1, wherein the skeletogenic differentiation gene comprises Dri, TBr, Ets, Cyclophilin, EpHx, Ficolin, Sm37, Sm27, MSP130L, Sm30, Sm50, or MSP130.

* * * * *